United States Patent
Cheng et al.

(10) Patent No.: US 10,780,104 B2
(45) Date of Patent: *Sep. 22, 2020

(54) COMPOSITIONS INCLUDING TRICIRIBINE AND EPIDERMAL GROWTH FACTOR RECEPTOR INHIBITOR COMPOUNDS OR SALTS THEREOF AND METHODS OF USE THEREOF

(71) Applicant: University of South Florida, Tampa, FL (US)

(72) Inventors: Jin Q. Cheng, Tampa, FL (US); Said M. Sebti, Tampa, FL (US)

(*) Notice: Subject to any disclaimer, the term of this patent is extended or adjusted under 35 U.S.C. 154(b) by 58 days.

This patent is subject to a terminal disclaimer.

(21) Appl. No.: 15/487,843

(22) Filed: Apr. 14, 2017

(65) Prior Publication Data

US 2017/0216337 A1 Aug. 3, 2017

Related U.S. Application Data

(63) Continuation of application No. 14/998,352, filed on Dec. 28, 2015, now Pat. No. 9,655,914, which is a continuation of application No. 14/092,323, filed on Nov. 27, 2013, now Pat. No. 9,265,783, which is a continuation of application No. 13/453,789, filed on Apr. 23, 2012, now Pat. No. 8,673,867, which is a continuation of application No. 12/118,861, filed on May 12, 2008, now abandoned, which is a continuation-in-part of application No. 11/096,082, filed on Mar. 29, 2005, now Pat. No. 8,435,959.

(60) Provisional application No. 60/557,599, filed on Mar. 29, 2004.

(51) Int. Cl.
| | |
|---|---|
| *A61K 31/7064* | (2006.01) |
| *A61K 31/7076* | (2006.01) |
| *A61K 45/06* | (2006.01) |
| *A61K 9/00* | (2006.01) |
| *A61K 31/517* | (2006.01) |
| *A61K 31/5377* | (2006.01) |
| *A61K 31/7068* | (2006.01) |
| *C12Q 1/6886* | (2018.01) |
| *G01N 33/574* | (2006.01) |

(52) U.S. Cl.
CPC ........ *A61K 31/7064* (2013.01); *A61K 9/0019* (2013.01); *A61K 9/0053* (2013.01); *A61K 31/517* (2013.01); *A61K 31/5377* (2013.01); *A61K 31/7068* (2013.01); *A61K 31/7076* (2013.01); *A61K 45/06* (2013.01); *C12Q 1/6886* (2013.01); *G01N 33/57426* (2013.01); *C12Q 2600/106* (2013.01); *C12Q 2600/158* (2013.01); *G01N 2333/912* (2013.01)

(58) Field of Classification Search
CPC .............. A61K 31/7064; A61K 9/0019; A61K 9/0053; A61K 31/517; A61K 31/5377; A61K 31/7076; A61K 45/06
USPC ........................................................... 514/43
See application file for complete search history.

(56) References Cited

PUBLICATIONS

Schilcher et al. (Journal of Chromatography (1985), 337 (1), 55-62).*
Feldman (Leukemia Research 24 (2000) 189-191).*
Cappellini et al. (Leukemia (2003) 17, 2157-2167).*
Wotring et al. (Cancer treatment reports, (Apr. 1986) vol. 70, No. 4, pp. 491-497).*

* cited by examiner

*Primary Examiner* — Shaojia A Jiang
*Assistant Examiner* — Michael C Henry
(74) *Attorney, Agent, or Firm* — Seyfarth Shaw LLP; Dean Fanelli

(57) ABSTRACT

This application relates to combination therapies including triciribine compounds and epidermal growth factor receptor inhibitor compounds, particularly erlotinib-like compounds and compositions with reduced toxicity for the treatment and prevention of tumors, cancer, and other disorders associated with abnormal cell proliferation.

22 Claims, 28 Drawing Sheets

Specification includes a Sequence Listing.

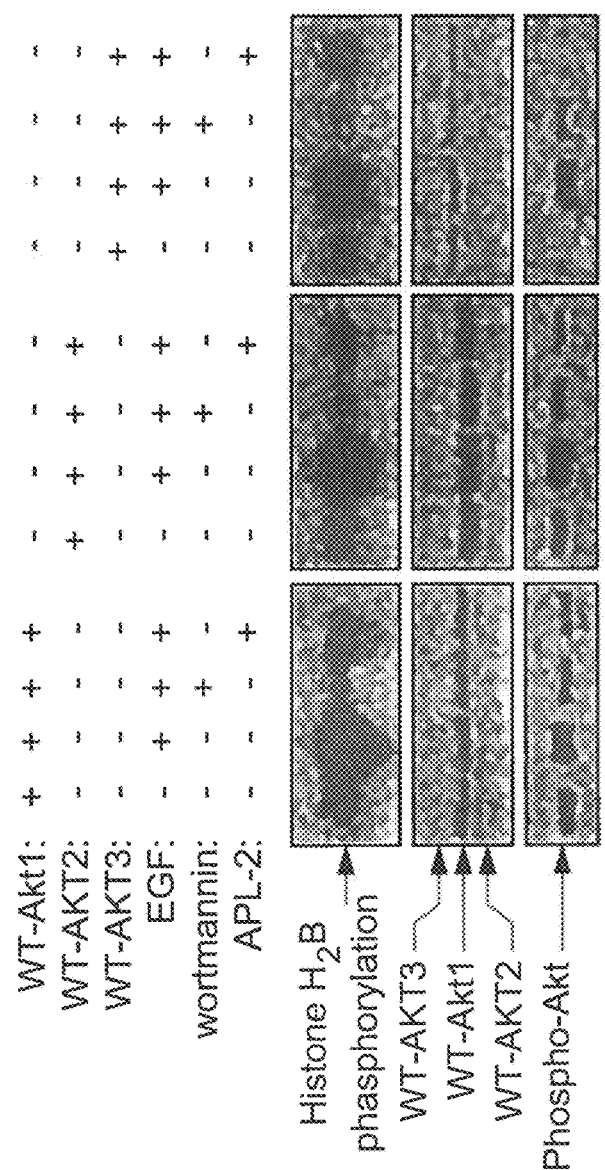
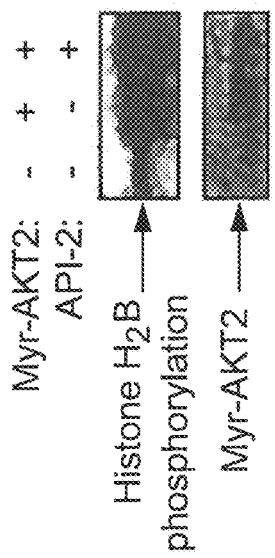
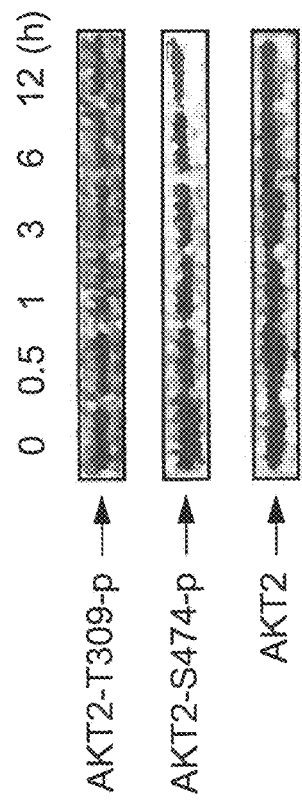
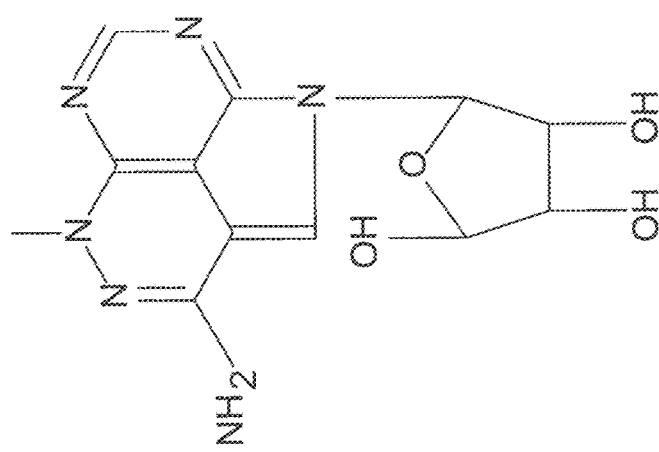
FIG. 1A
FIG. 1B
FIG. 1C
FIG. 1D

FIG. 3A

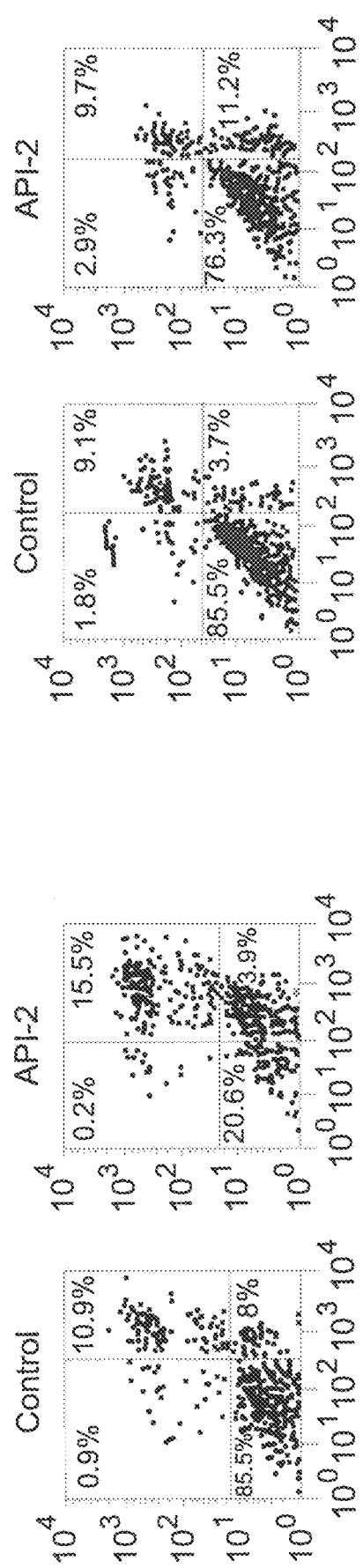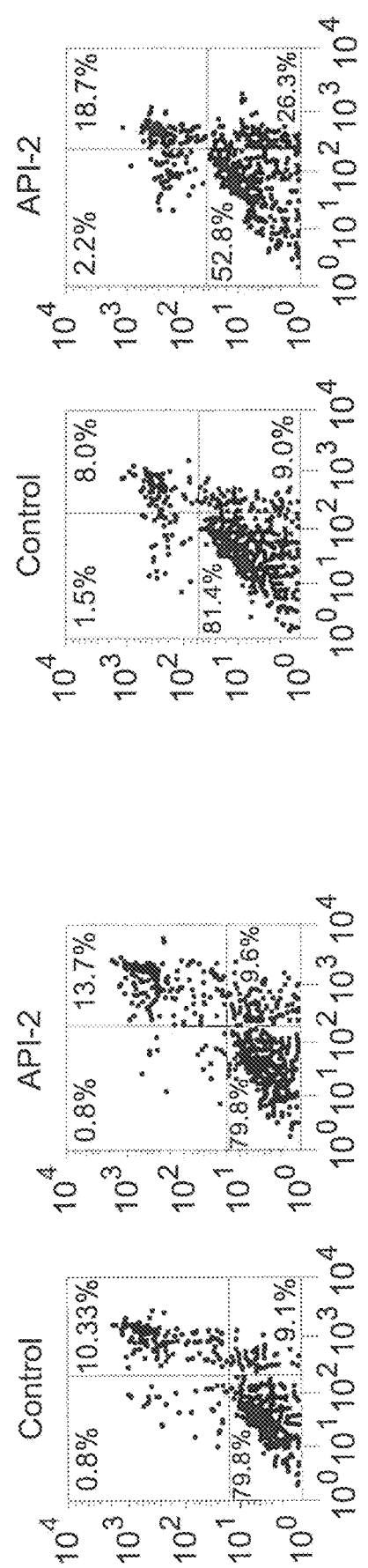
FIG. 3C-4
FIG. 3C-5
FIG. 3C-6
FIG. 3C-7

Figures 1, 3B:
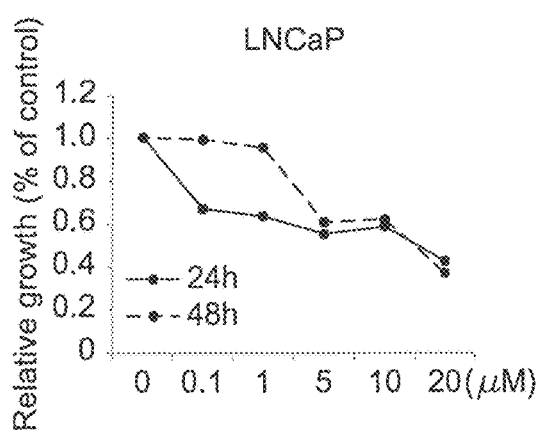
Figures 3, 3B, 4:
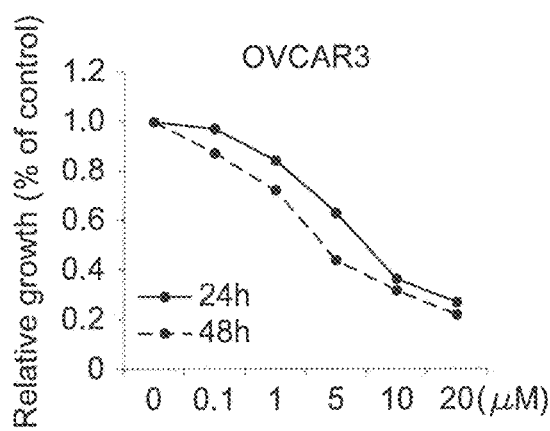
Figures 2, 3B:
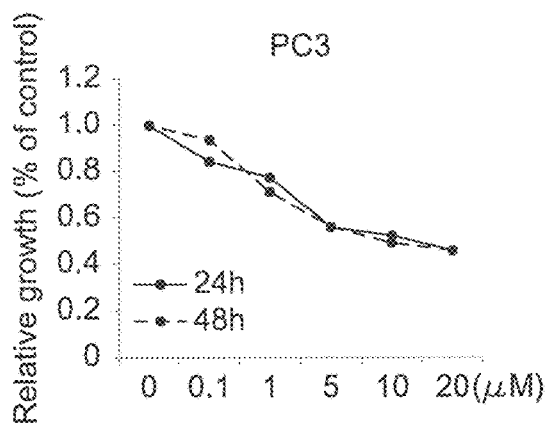

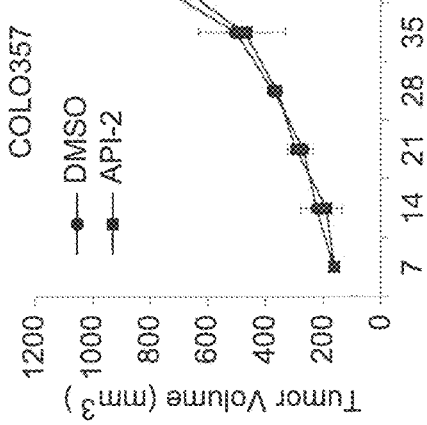
FIG. 4B-2
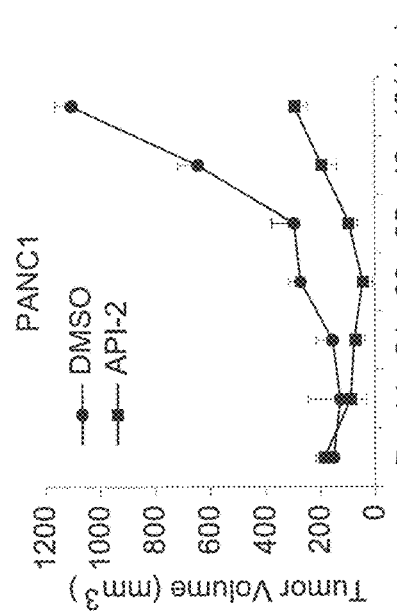
FIG. 4B-1
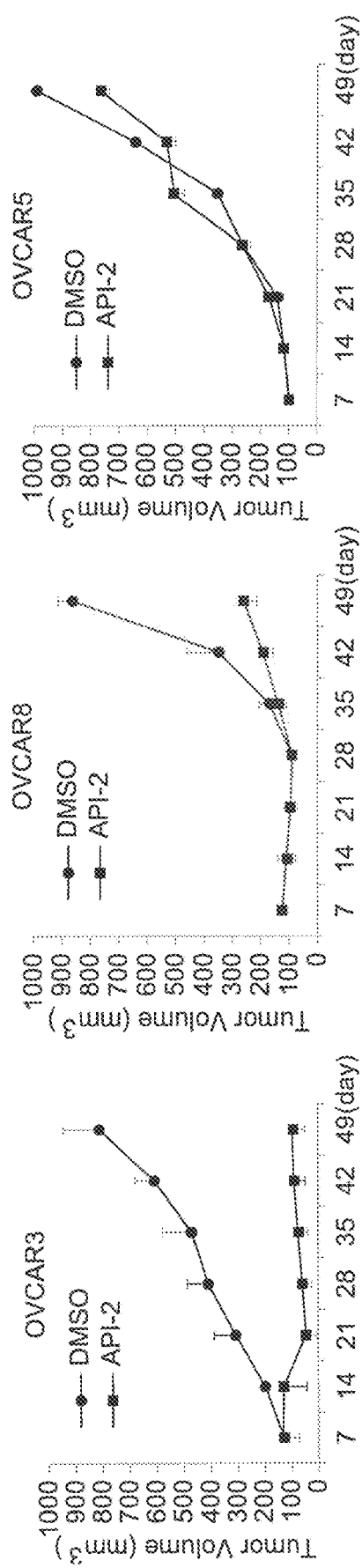
FIG. 4B-5
FIG. 4B-4
FIG. 4B-3

```
    atgaacgacgtagccattgtgaaggagggctggctgcacaaacgaggggaatatattaaa
1   ------------+------------+------------+------------+------------+------------+ 60
    tacttgctgcatcggtaacacttcctcccgaccgacgtgtttgctcccttatataattt
``` a    M   N   D   V   A   I   V   K   E   G   W   L   H   K   R   G   E   Y   F   K    -

```
    acctggcggccacgctacttcctcctcaagaacgatggcacctttattggctacaaggaa
61  ------------+------------+------------+------------+------------+------------+ 120
    tggaccgccggtgcgatgaaggaggagttcttgctaccgtggaaataaccgatgttcctt
``` a    T   W   R   P   R   Y   F   L   L   K   N   D   G   T   F   I   G   Y   K   E    -

```
    cggcctcaggatgtggatcagcgagagtccccactcaacaacttctcagtggcacaatgc
121 ------------+------------+------------+------------+------------+------------+ 180
    gccggagtcctacacctagtcgctctcaggggtgagttgttgaagagtcaccgtgttacg
``` a    R   P   Q   D   V   D   Q   R   E   S   P   L   N   N   F   S   V   A   Q   C    -

PstI
                                                             |

```
    cagctgatgaagacagagcggccaaggcccaacacctttatcatccgctgcctgcagtgg
181 ------------+------------+------------+------------+------------+------------+ 240
    gtcgactacttctgtctcgccggttccgggttgtggaaatagtaggcgacggacgtcacc
``` a    Q   L   M   K   T   E   R   P   R   P   N   T   F   I   I   R   C   L   Q   W    -

```
    accacagtcattgagcgcaccttccatgtagaaacgcctgaggagcgggaagaatgggcc
241 ------------+------------+------------+------------+------------+------------+ 300
    tggtgtcagtaactcgcgtggaaggtacatctttgcggactcctcgcccttcttacccgg
``` a    T   T   V   I   E   R   T   F   H   V   E   T   P   E   E   R   E   E   W   A    -

```
    accgccattcagactgtggccgatggactcaagaggcaggaagaagagacgatggacttc
301 ------------+------------+------------+------------+------------+------------+ 360
    tggcggtaagtctgacaccggctacctgagttctccgtccttcttctctgctacctgaag
``` a    T   A   I   Q   T   V   A   D   G   L   K   R   Q   E   E   E   T   M   D   F    -

```
    cgatcaggctcacccagtgacaactcaggggctgaagagatggaggtgtccctggccaag
361 ------------+------------+------------+------------+------------+------------+ 420
    gctagtccgagtgggtcactgttgagtccccgacttctctacctccagggaccggttc
``` a    R   S   G   S   P   S   D   N   S   G   A   E   E   M   E   V   S   L   A   K    -

FIG. 6A

```
              cccaagcaccgtgtgaccatgaacgagtttgagtacctgaaactactgggcaagggcacc
       421    ------------+------------+------------+------------+------------+------------+  480
              gggttcgtggcacactggtacttgctcaaactcatggactttgatgacccgttcccgtgg a      P  K  H  R  V  T  M  N  E  F  E  Y  L  K  L  L  G  K  G  T   - tttgggaaagtgattctggtaaaagagaaggccacaggccgctactatgccatgaagatc
       481    ------------+------------+------------+------------+------------+------------+  540
              aaacccttttcactaagaccattttctcttccggtgtccggcgatgatacggtacttctag a      F  G  K  V  I  L  V  K  E  K  A  T  G  R  Y  Y  A  M  K  I   - ctcaagaaggaggtcatcgtcgccaaggatgaggttgcccacacgcttactgaaaaccgt
       541    ------------+------------+------------+------------+------------+------------+  600
              gagttcttcctccagtagcagcggttcctactccaacgggtgtgcgaatgacttttggca a      L  K  K  E  V  I  V  A  K  D  E  V  A  H  T  L  T  E  N  R   -
                     PstI
                      |
              gtcctgcagaactctaggcatcccttccttacggccctcaagtactcattccagacccac
       601    ------------+------------+------------+------------+------------+------------+  660
              caggacgtcttgagatccgtagggaaggaatgccgggagttcatgagtaaggtctgggtg a      V  L  Q  N  S  R  H  P  F  L  T  A  L  K  Y  S  F  Q  T  H   -
                                                                      XhoI
                                                                       |
              gaccgcctctgctttgtcatggagtatgccaacgggggcgagctcttcttccacctgtct
       661    ------------+------------+------------+------------+------------+------------+  720
              ctggcggagacgaaacagtacctcatacggttgccccgctcgagaagaaggtggacaga a      D  R  L  C  F  V  M  E  Y  A  N  G  G  E  L  F  F  H  L  S   - cgagagcgcgtgttctccgaggaccgggccgcttctatggtgcggagattgtgtctgcc
       721    ------------+------------+------------+------------+------------+------------+  780
              gctctcgcgcacaagaggctcctggcccgggcgaagataccacgcctctaacacagacgg a      R  E  R  V  F  S  E  D  R  A  R  F  Y  G  A  E  I  V  S  A   - ctggactacttgcactccgagaagaacgtggtgtaccgggacctgaagctagagaacctc
       781    ------------+------------+------------+------------+------------+------------+  840
              gacctgatgaacgtgaggctcttcttgcaccacatggccctggacttcgatctcttggag a      L  D  Y  L  H  S  E  K  N  V  V  Y  R  D  L  K  L  E  N  L   -
```

FIG. 6B

```
       atgctggacaaggacgggcacatcaagataacggacttcgggctgtgcaaggagggatc
   841 ------------+---------+---------+---------+---------+---------+ 900
       tacgacctgttcctgcccgtgtagttctattgcctgaagcccgacacgttcctccctag a      M  L  D  K  D  G  H  I  K  I  T  D  F  G  L  C  K  E  G  I   - aaggatggtgccactatgaagacattctgcggaacgccggagtacctggcccctgaggtg
   901 ------------+---------+---------+---------+---------+---------+ 960
       ttcctaccacggtgatacttctgtaagacgccttgcggcctcatggaccggggactccac a      K  D  G  A  T  M  K  T  F  C  G  T  P  E  Y  L  A  P  E  V   - ctggaagacaacgactacggccgtgcagtggactggtggggctgggcgtggtcatgtat
   961 ------------+---------+---------+---------+---------+---------+ 1020
       gaccttctgttgctgatgccggcacgtcacctgaccaccccgacccgcaccagtacata a      L  E  D  N  D  Y  G  R  A  V  D  W  W  G  L  G  V  V  M  Y   - gagatgatgtgtggccgcctgcccttctacaaccaggaccacgagaagctgttcgagctg
  1021 ------------+---------+---------+---------+---------+---------+ 1080
       ctctactacacaccggcggacgggaagatgttggtcctggtgctcttcgacaagctcgac a      E  M  M  C  G  R  L  P  F  Y  N  Q  D  H  E  K  L  F  E  L   - atcctcatggaggagatccgcttcccgcgcacactcggccctgaggccaagtccctgctc
  1081 ------------+---------+---------+---------+---------+---------+ 1140
       taggagtacctcctctaggcgaagggcgcgtgtgagccgggactccggttcagggacgag a      I  L  M  E  E  I  R  F  P  R  T  L  G  P  E  A  K  S  L  L   - tccggctgctcaagaaggaccctacacagaggctcggtgggggctctgaggatgccaag
  1141 ------------+---------+---------+---------+---------+---------+ 1200
       aggcccgacgagttcttcctgggatgtgtctccgagccaccccgagactcctacggttc a      S  G  L  L  K  K  D  P  T  Q  R  L  G  G  S  E  D  A  K     - gagatcatgcagcaccggttctttgccaacatcgtgtggcaggatgtgtatgagaagaag
  1201 ------------+---------+---------+---------+---------+---------+ 1260
       ctctagtacgtcgtggccaagaaacggttgtagcacaccgtcctacacatactcttcttc a      E  I  M  Q  H  R  F  F  A  N  I  V  W  Q  D  V  Y  E  K  K   -
```

FIG. 6C

```
        ctgagcccacctttcaagccccaggtcacctctgagactgacaccaggtatttcgatgag
   1261 ------------+----------+----------+----------+----------+---------+ 1320
        gactcgggtggaaagttcggggtccagtggagactctgactgtggtccataaagctactc a      L  S  P  P  F  K  P  Q  V  T  S  E  T  D  T  R  Y  F  D  E  - gagttcacagctcagatgatcaccatcacgccgcctgatcaagatgacagcatggagtgt
   1321 ------------+----------+----------+----------+----------+---------+ 1380
        ctcaagtgtcgagtctactagtggtagtgcggcggactagttctactgtcgtacctcaca a      E  F  T  Q  Q  M  I  T  I  T  P  P  D  Q  D  D  S  M  E  C  - gtggacagtgagcggaggccgcacttcccccagttctcctactgacccagtggcacagcc
   1381 ------------+----------+----------+----------+----------+---------+ 1440
        cacctgtcactcgcctccggcgtgaaggggtcaagaggatgagtcggtcaccgtgtcgg a      V  D  S  E  R  R  P  H  F  P  Q  F  S  Y  S  A  S  G  T  A  - tga
   1441 --- 1443
        act a      *  -
```

FIG. 6D

```
     ATGAATGAGGTGTCTGTCATCAAAGAAGGCTGGCTCCACAAGCGTGGTGAATACATCAAG
328  --+---------+---------+---------+---------+---------+------ 387
     TACTTACTCCACAGACAGTAGTTTCTTCCGACCGAGGTGTTCGCACCACTTATGTAGTTC a    M  N  E  V  S  V  I  K  E  G  W  L  H  K  R  G  E  Y  I  K  -

ACCTGGAGGCCACGGTACTTCCTGCTGAAGAGCGACGGCTCCTTCATTGGGTACAAGGAG
388  --+---------+---------+---------+---------+---------+------ 447
     TGGACCTCCGGTGCCATGAAGGACGACTTCTCGCTGCCGAGGAAGTAACCCATGTTCCTC a    T  W  R  P  R  Y  F  L  L  K  S  D  G  S  F  I  G  Y  K  E  -

AGGCCCGAGGCCCCTGATCAGACTCTACCCCCCTTAAACAACTTCTCCGTAGCAGAATGC
448  --+---------+---------+---------+---------+---------+------ 507
     TCCGGGCTCCGGGGACTAGTCTGAGATGGGGGGAATTTGTTGAAGAGGCATCGTCTTACG a    R  P  E  A  P  D  Q  T  L  P  P  L  N  N  F  S  V  A  E  C  -

PstI
                                                         |
     CAGCTGATGAAGACCGAGAGGCCGCGACCCAACACCTTTGTCATACGCTGCCTGCAGTGG
508  --+---------+---------+---------+---------+---------+------ 567
     GTCGACTACTTCTGGCTCTCCGGCGCTGGGTTGTGGAAACAGTATGCGACGGACGTCACC a    Q  L  M  K  T  E  R  P  R  P  N  T  F  V  I  R  C  L  Q  W  -

ACCACAGTCATCGAGAGGACCTTCCACGTGGATTCTCCAGACGAGAGGGAGGAGTGGATG
568  --+---------+---------+---------+---------+---------+------ 627
     TGGTGTCAGTAGCTCTCCTGGAAGGTGCACCTAAGAGGTCTGCTCTCCCTCCTCACCTAC a    T  T  V  I  E  R  T  F  H  V  D  S  P  D  E  R  E  E  W  M  -

ApaI
                                     |
     CGGGCCATCCAGATGGTCGCCAACAGCCTCAAGCAGCGGGCCCCAGGCGAGGACCCCATG
628  --+---------+---------+---------+---------+---------+------ 687
     GCCCGGTAGGTCTACCAGCGGTTGTCGGAGTTCGTCGCCCGGGGTCCGCTCCTGGGGTAC a    R  A  I  Q  M  V  A  N  S  L  K  Q  R  A  P  G  E  D  P  M  -

GACTACAAGTGTGGCTCCCCCAGTGACTCCTCCACGACTGAGGAGATGGAAGTGGCGGTC
688  --+---------+---------+---------+---------+---------+------ 747
     CTGATGTTCACACCGAGGGGGTCACTGAGGAGGTGCTGACTCCTCTACCTTCACCGCCAG a    D  Y  K  C  G  S  P  S  D  S  S  T  T  E  E  M  E  V  A  V  -
```

FIG. 7A

```
     AGCAAGGCACGGGCTAAAGTGACCATGAATGACTTCGACTATCTCAAACTCCTTGGCAAG
748  ---+---------+---------+---------+---------+---------+------ 807
     TCGTTCCGTGCCCGATTTCACTGGTACTTACTGAAGCTGATAGAGTTTGAGGAACCGTTC a     S  K  A  R  A  K  V  T  M  N  D  F  D  Y  L  K  L  L  G  K  -

GGAACCTTTGGCAAAGTCATCCTGGTGCGGGAGAAGGCCACTGGCCGCTACTACGCCATG
808  ---+---------+---------+---------+---------+---------+------ 867
     CCTTGGAAACCGTTTCAGTAGGACCACGCCCTCTTCCGGTGACCGGCGATGATGCGGTAC a     G  T  F  G  K  V  I  L  V  R  E  K  A  T  G  R  Y  Y  A  M  -

AAGATCCTGCGAAAGGAAGTCATCATTGCCAAGGATGAAGTCGCTCACACAGTCACCGAG
868  ---+---------+---------+---------+---------+---------+------ 927
     TTCTAGGACGCTTTCCTTCAGTAGTAACGGTTCCTACTTCAGCGAGTGTGTCAGTGGCTC a     K  I  L  R  K  E  V  I  I  A  K  D  E  V  A  H  T  V  T  E  -

AGCCGGGTCCTCCAGAACACCAGGCACCCGTTCCTCACTGCGCTGAAGTATGCCTTCCAG
928  ---+---------+---------+---------+---------+---------+------ 987
     TCGGCCCAGGAGGTCTTGTGGTCCGTGGGCAAGGAGTGACGCGACTTCATACGGAAGGTC a     S  R  V  L  Q  N  T  R  H  P  F  L  T  A  L  K  Y  A  F  Q  -

ACCCACGACCGCCTGTGCTTTGTGATGGAGTATGCCAACGGGGGTGAGCTGTTCTTCCAC
988  ---+---------+---------+---------+---------+---------+------ 1047
     TGGGTGCTGGCGGACACGAAACACTACCTCATACGGTTGCCCCACTCGACAAGAAGGTG a     T  H  D  R  L  C  F  V  M  E  Y  A  N  G  G  E  L  F  F  H  -

SmaI
        XmaI |                           ApaI
         |  |                              |
     CTGTCCCGGGAGCGTGTCTTCACAGAGGAGCGGGCCCGGTTTTATGGTGCAGAGATTGTC
1048 ---+---------+---------+---------+---------+---------+------ 1107
     GACAGGGCCCTCGCACAGAAGTGTCTCCTCGCCCGGGCCAAAATACCACGTCTCTAACAG a     L  S  R  E  R  V  F  T  E  E  R  A  R  F  Y  G  A  E  I  V  -

TCGGCTCTTGAGTACTTGCACTCGCGGGACGTGGTATACCGCGACATCAAGCTGGAAAAC
1108 ---+---------+---------+---------+---------+---------+------ 1167
     AGCCGAGAACTCATGAACGTGAGCGCCCTGCACCATATGGCGCTGTAGTTCGACCTTTTG a     S  A  L  E  Y  L  H  S  R  D  V  V  Y  R  D  I  K  L  E  N  -
```

FIG. 7B

```
         CTCATGCTGGACAAAGATGGCCACATCAAGATCACTGACTTTGGCCTCTGCAAAGAGGGC
   1168  --+---------+---------+---------+---------+---------+------  1227
         GAGTACGACCTGTTTCTACCGGTGTAGTTCTAGTGACTGAAACCGGAGACGTTTCTCCCG a    L   M   L   D   K   D   G   H   I   K   I   T   D   F   G   L   C   K   E   G  -

ATCAGTGACGGGGCCACCATGAAAACCTTCTGTGGGACCCCGGAGTACCTGGCGCCTGAG
   1228  --+---------+---------+---------+---------+---------+------  1287
         TAGTCACTGCCCCGGTGGTACTTTTGGAAGACACCCTGGGGCCTCATGGACCGCGGACTC a    I   S   D   G   A   T   M   K   T   F   C   G   T   P   E   Y   L   A   P   E  -

GTGCTGGAGGACAATGACTATGGCCGGGCCGTGGACTGGTGGGGGCTGGGTGTGGTCATG
   1288  --+---------+---------+---------+---------+---------+------  1347
         CACGACCTCCTGTTACTGATACCGGCCCGGCACCTGACCACCCCGACCCACACCAGTAC a    V   L   E   D   N   D   Y   G   R   A   V   D   W   W   G   L   G   V   V   M  -

TACGAGATGATGTGCGGCCGCCTGCCCTTCTACAACCAGGACCACGAGCGCCTCTTCGAG
   1348  --+---------+---------+---------+---------+---------+------  1407
         ATGCTCTACTACACGCCGGCGGACGGGAAGATGTTGGTCCTGGTGCTCGCGGAGAAGCTC a    Y   E   M   M   C   G   R   L   P   F   Y   N   Q   D   H   E   R   L   F   E  -
           SacI
             |
         CTCATCCTCATGGAAGAGATCCGCTTCCCGCGCACGCTCAGCCCCGAGGCCAAGTCCCTG
   1408  --+---------+---------+---------+---------+---------+------  1467
         GAGTAGGAGTACCTTCTCTAGGCGAAGGGCGCGTGCGAGTCGGGGCTCCGGTTCAGGGAC a    L   I   L   M   E   E   I   R   F   P   R   T   L   S   P   E   A   K   S   L  -
                                                          ApaI
                                                            |
         CTTGCTGGGCTGCTTAAGAAGGACCCCAAGCAGAGGCTTGGTGGGGGGCCCAGCGATGCC
   1468  --+---------+---------+---------+---------+---------+------  1527
         GAACGACCCGACGAATTCTTCCTGGGGTTCGTCTCCGAACCACCCCCGGGTCGCTACGG a    L   A   G   L   L   K   K   D   P   K   Q   R   L   G   G   G   P   S   D   A  -

AAGGAGGTCATGGAGCACAGGTTCTTCCTCAGCATCAACTGGCAGGACGTGGTCCAGAAG
   1528  --+---------+---------+---------+---------+---------+------  1587
         TTCCTCCAGTACCTCGTGTCCAAGAAGGAGTCGTAGTTGACCGTCCTGCACCAGGTCTTC a    K   E   V   M   E   H   R   F   F   L   S   I   N   W   Q   D   V   V   Q   K  -
```

FIG. 7C

```
                                          SalI
                                           |
       AAGCTCCTGCCACCCTTCAAACCTCAGGTCACGTCCGAGGTCGACACAAGGTACTTCGAT
1588   --+---------+---------+---------+---------+---------+------ 1647
       TTCGAGGACGGTGGGAAGTTTGGAGTCCAGTGCAGGCTCCAGCTGTGTTCCATGAAGCTA a      K  L  L  P  P  F  K  P  Q  V  T  S  E  V  D  T  R  Y  F  D  -

GATGAATTTACCGCCCAGTCCATCACAATCACACCCCCTGACCGCTATGACAGCCTGGGC
1648   --+---------+---------+---------+---------+---------+------ 1707
       CTACTTAAATGGCGGGTCAGGTAGTGTTAGTGTGGGGGACTGGCGATACTGTCGGACCCG a      D  E  F  T  A  Q  S  I  T  I  T  P  P  D  R  Y  D  S  L  G  -

TTACTGGAGCTGGACCAGCGGACCCACTTCCCCCAGTTCTCCTACTCGGCCAGCATCCGC
1708   --+---------+---------+---------+---------+---------+------ 1767
       AATGACCTCGACCTGGTCGCCTGGGTGAAGGGGGTCAAGAGGATGAGCCGGTCGTAGGCG a      L  L  E  L  D  Q  R  T  H  F  P  Q  F  S  Y  S  A  S  I  R  -

GAGTGAGCAGTCTGCCCACGCAGAGGACGCACGCTCGCTGCCATCACCGCTGGGTGGTTT
1768   --+---------+---------+---------+---------+---------+------ 1827
       CTCACTCGTCAGACGGGTGCGTCTCCTGCGTGCGAGCGACGGTAGTGGCGACCCACCAAA a      E  *  A  V  C  P  R  R  G  R  T  L  A  A  I  T  A  G  W  F  -

TTTACCCCTGCCCGG
1828   --+---------+-- 1842
       AAATGGGGACGGGCC a      F  T  P  A  R  -
```

FIG. 7D

```
       gggctcagaggggagtcatcatgagcgatgttaccattgtgaaagaaggttgggttcaga
   1   ------------+------------+------------+------------+------------+------------+  60
       cccgagtctccctcagtagtactcgctacaatggtaacactttcttccaacccaagtct a        A  Q  R  G  V  I  M  S  D  V  T  I  V  K  E  G  W  V  Q  K - agaggggagaatatataaaaaactggaggccaagatacttccttttgaagacagatggct
  61   ------------+------------+------------+------------+------------+------------+ 120
       tctcccctcttatatattttttgacctccggttctatgaaggaaaacttctgtctaccga a        R  G  E  Y  I  K  N  W  R  P  R  Y  F  L  L  K  T  D  G  S - cattcataggatataaagagaaacctcaagatgtggatttaccttatcccctcaacaact
 121   ------------+------------+------------+------------+------------+------------+ 180
       gtaagtatcctatatttctctttggagttctacacctaaatggaataggggagttgttga a        F  I  G  Y  K  E  K  P  Q  D  V  D  L  P  Y  P  L  N  N  F - tttcagtggcaaaatgccagttaatgaaaacagaacgaccaaagccaaacacatttataa
 181   ------------+------------+------------+------------+------------+------------+ 240
       aaagtcaccgttttacggtcaattacttttgtcttgctggtttcggtttgtgtaaatatt a        S  V  A  K  C  Q  L  M  K  T  E  R  P  K  P  N  T  F  I  I - tcagatgtctccagtggactactgttatagagagaacatttcatgtagatactccagagg
 241   ------------+------------+------------+------------+------------+------------+ 300
       agtctacagaggtcacctgatgacaatatctctcttgtaaagtacatctatgaggtctcc a        R  C  L  Q  W  T  T  V  I  E  R  T  F  H  V  D  T  P  E  E -
                                                         PstI
                                                           |
       aaagggaagaatggacagaagctatccaggctgtagcagacagactgcagaggcaagaag
 301   ------------+------------+------------+------------+------------+------------+ 360
       tttcccttcttacctgtcttcgataggtccgacatcgtctgtctgacgtctccgttcttc a        R  E  E  W  T  E  A  I  Q  A  V  A  D  R  L  Q  R  Q  E  E - aggagagaatgaattgtagtccaacttcacaaattgataatataggagaggaagagatgg
 361   ------------+------------+------------+------------+------------+------------+ 420
       tcctctcttacttaacatcaggttgaagtgtttaactattatatcctctccttctctacc a        E  R  M  N  C  S  P  T  S  Q  I  D  N  I  G  E  E  E  M  D -
```

FIG. 8A

```
           atgcctctacaacccatcataaaagaaagacaatgaatgattttgactatttgaaactac
      421  ------------+------------+------------+------------+------------+------------+ 480
           tacggagatgttgggtagtattttctttctgttacttactaaaactgataaactttgatg a       A  S  T  T  H  H  K  R  *  T  M  N  D  F  D  Y  L  K  L  L  - taggtaaaggcacttttgggaaagttattttggttcgagagaaggcaagtggaaaatact
      481  ------------+------------+------------+------------+------------+------------+ 540
           atccatttccgtgaaaaccctttcaataaaaccaagctctcttccgttcacctttatga a       G  K  G  T  F  G  K  V  I  L  V  R  E  K  A  S  G  K  Y  Y  - atgctatgaagattctgaagaaagaagtcattattgcaaaggatgaagtggcacacactc
      541  ------------+------------+------------+------------+------------+------------+ 600
           tacgatacttctaagacttctttcttcagtaataacgtttcctacttcaccgtgtgtgag a       A  M  K  I  L  K  K  E  V  I  I  A  K  D  E  V  A  H  T  L  - taactgaaagcagagtattaaagaacactagacatcccttttaacatccttgaaatatt
      601  ------------+------------+------------+------------+------------+------------+ 660
           attgactttcgtctcataattcttgtgatctgtagggaaaaattgtaggaactttataa a       T  E  S  R  V  L  K  N  T  R  H  P  F  L  T  S  L  K  Y  S  - ccttccagacaaaagaccgtttgtgttttgtgatggaatatgttaatgggggcgagctgt
      661  ------------+------------+------------+------------+------------+------------+ 720
           ggaaggtctgttttctggcaaacacaaaacactaccttatacaattaccccgctcgaca a       F  Q  T  K  D  R  L  C  F  V  M  E  Y  V  N  G  G  E  L  F  - ttttccatttgtcgagagagcgggtgttctctgaggaccgcacacgtttctatggtgcag
      721  ------------+------------+------------+------------+------------+------------+ 780
           aaaaggtaaacagctctctcgcccacaagagactcctggcgtgtgcaaagataccacgtc a       F  H  L  S  R  E  R  V  F  S  E  D  R  T  R  F  Y  G  A  E  - aaattgtctctgccttggactatctacattccggaagattgtgtaccgtgatctcaagt
      781  ------------+------------+------------+------------+------------+------------+ 840
           tttaacagagacggaacctgatagatgtaaggcctttctaacacatggcactagagttca a       I  V  S  A  L  D  Y  L  H  S  G  K  I  V  Y  R  D  L  K  L  -
```

FIG. 8B

```
     tggagaatctaatgctggacaaagatggccacataaaaattacagattttggactttgca
841  ------------+-----------+-----------+-----------+-----------+-----------+ 900
     acctcttagattacgacctgtttctaccggtgtattttaatgtctaaaacctgaaacgt
``` a       E   N   L   M   D   K   D   G   H   I   K   I   T   D   F   G   L   C   K -

```
     aagaagggatcacagatgcagccaccatgaagacattctgtggcactccagaatatctgg
901  ------------+-----------+-----------+-----------+-----------+-----------+ 960
     ttcttccctagtgtctacgtcggtggtacttctgtaagacaccgtgaggtcttatagacc
``` a       E   G   I   T   D   A   A   T   M   K   T   F   C   G   T   P   E   Y   L   A -

```
     caccagaggtgttagaagataatgactatggccgagcagtagactggtggggcctagggg
961  ------------+-----------+-----------+-----------+-----------+-----------+ 1020
     gtggtctccacaatcttctattactgataccggctcgtcatctgaccaccccggatcccc
``` a       P   E   V   L   E   D   N   D   Y   G   R   A   V   D   W   W   G   L   G   V -

```
     ttgtcatgtatgaaatgatgtgtgggaggttacctttctacaaccaggaccatgagaac
1021 ------------+-----------+-----------+-----------+-----------+-----------+ 1080
     aacagtacatactttactacacaccctccaatggaaagatgttggtcctggtactctttg
``` a       V   M   Y   E   M   M   C   G   R   L   P   F   Y   N   Q   D   H   E   K   L -

```
     ttttgaattaatattaatggaagacattaaatttcctcgaacactctcttcagatgcaa
1081 ------------+-----------+-----------+-----------+-----------+-----------+ 1140
     aaaacttaattataattaccttctgtaatttaaaggagcttgtgagagaagtctacgtt
``` a       F   E   L   I   L   M   E   D   I   K   F   P   R   T   L   S   S   D   A   K -

BamHI
|

```
     aatcattgctttcagggctcttgataaaggatccaaataaacgccttggtggaggaccag
1141 ------------+-----------+-----------+-----------+-----------+-----------+ 1200
     ttagtaacgaaagtcccgagaactatttcctaggtttatttgcggaaccacctcctggtc
``` a       S   L   L   S   G   L   L   I   K   D   P   N   K   R   L   G   G   P   D -

```
     atgatgcaaaagaaattatgagacacagtttcttctctggagtaaactggcaagatgtat
1201 ------------+-----------+-----------+-----------+-----------+-----------+ 1260
     tactacgttttctttaatactctgtgtcaaagaagagacctcatttgaccgttctacata
``` a       D   A   K   E   I   M   R   H   S   F   F   S   G   V   N   W   Q   D   V   Y -

FIG. 8C

```
        HindIII
           |
        atgataaaaagcttgtacctccttttaaacctcaagtaacatctgagacagatactagat
   1261 ------------+----------+----------+----------+----------+----------+ 1320
        tactattttcgaacatggaggaaaatttggagttcattgtagactctgtctatgatcta a     D  K  K  L  V  P  P  F  K  P  Q  V  T  S  E  T  D  T  R  Y - attttgatgaagaatttacagctcagactattacaataacaccacctgaaaaatatgatg
   1321 ------------+----------+----------+----------+----------+----------+ 1380
        taaaactacttcttaaatgtcgagtctgataatgttattgtggtgacttttatactac a     F  D  E  E  F  T  A  Q  T  I  T  I  T  P  P  E  K  Y  D  E -
                                      NotI
                                       |
        aggatggtatggactgcatggacaatgagaggcggccgcatttccctcaatttcctact
   1381 ------------+----------+----------+----------+----------+----------+ 1440
        tcctaccataccgacgtacctgttactctccgccggcgtaaagggagttaaaaggatga a     D  G  M  D  C  M  D  N  E  R  R  P  H  F  P  Q  F  S  Y  S - ctgcaagtggacgagaataagtctctttcattctgctacttcactgtcatcttcaattta
   1441 ------------+----------+----------+----------+----------+----------+ 1500
        gacgttcacctgctcttattcagagaaagtaagacgatgaagtgacagtagaagttaaat a     A  S  G  R  E  *  V  S  F  I  L  L  H  C  H  L  Q  F  I - ttactgaaaa
   1501 ----------+ 1510
        aatgactttt a     T  E   -
```

FIG. 8D

| Drug | target | % growth inhibition in PTEN AS BT474.m1 cells ||||| Ttzm + drug significantly better than either alone? |
|---|---|---|---|---|---|---|---|
| | | Ttzm only | | drug only | | Ttzm + drug | |
| Triciribine | Akt | 9.5 | +/-4.2 | 19.2 | +/-9.2 | 36.6 | +/-3.3 | yes (P<0.001) |
| KP 372-1 | Akt | 0 | +/-4.1 | 36 | +/-2.1 | 38.8 | +/-3.2 | no |
| 4ADPIB | Akt | 0.9 | +/-9.7 | 23.7 | +/-2.4 | 32.2 | +/-3.4 | no |
| Edelfosine | Akt | 2.2 | +/-9.6 | 41.8 | +/-1.2 | 51.9 | +/-2.3 | no |
| RAD001 | mTOR | 10.9 | +/-4.9 | 19.3 | +/-2.5 | 33.7 | +/-1.4 | yes (P<0.05) |
| QLT 0267 | ILK | 20 | +/-6.8 | 30.3 | +/-8.4 | 44.8 | +/-6.9 | yes (P<0.05) |

FIG. 9A

Figures 3, 3B, 4, 5:
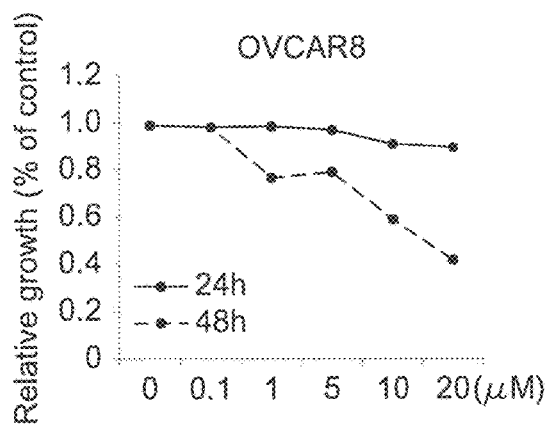
Figures 3, 3B:
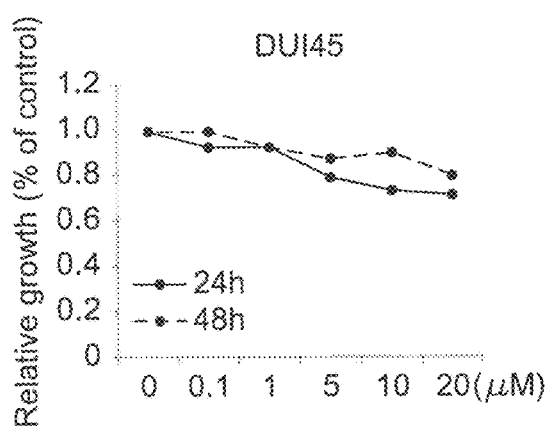
Figures 3, 3B, 4, 5, 6:
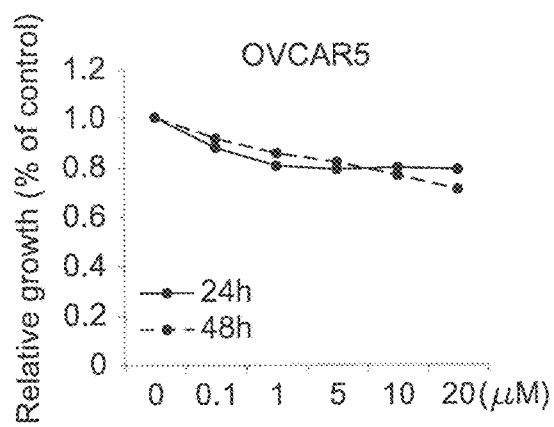
Figures 3, 3B, 4, 5, 6, 7:
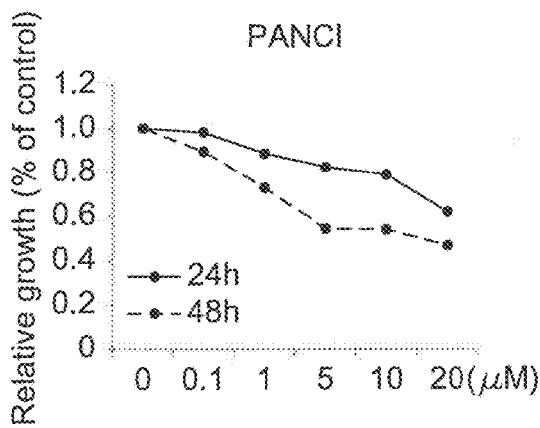
Figures 3, 3B, 4, 5, 6, 7, 8, 9:
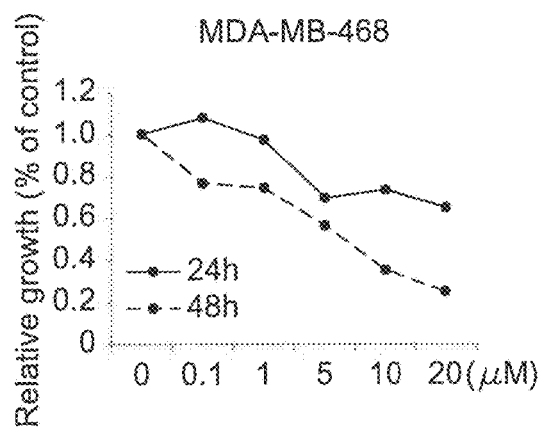
Figures 3, 3B, 4, 5, 6, 7, 8:
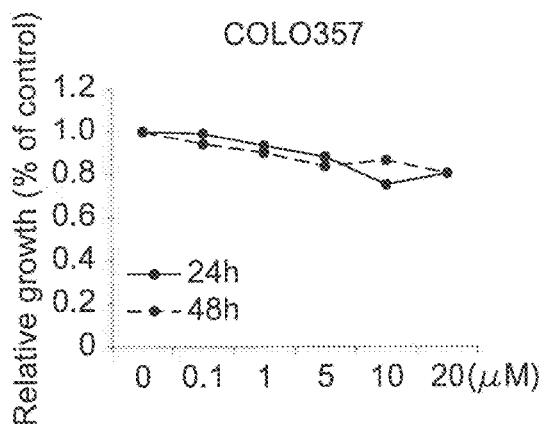

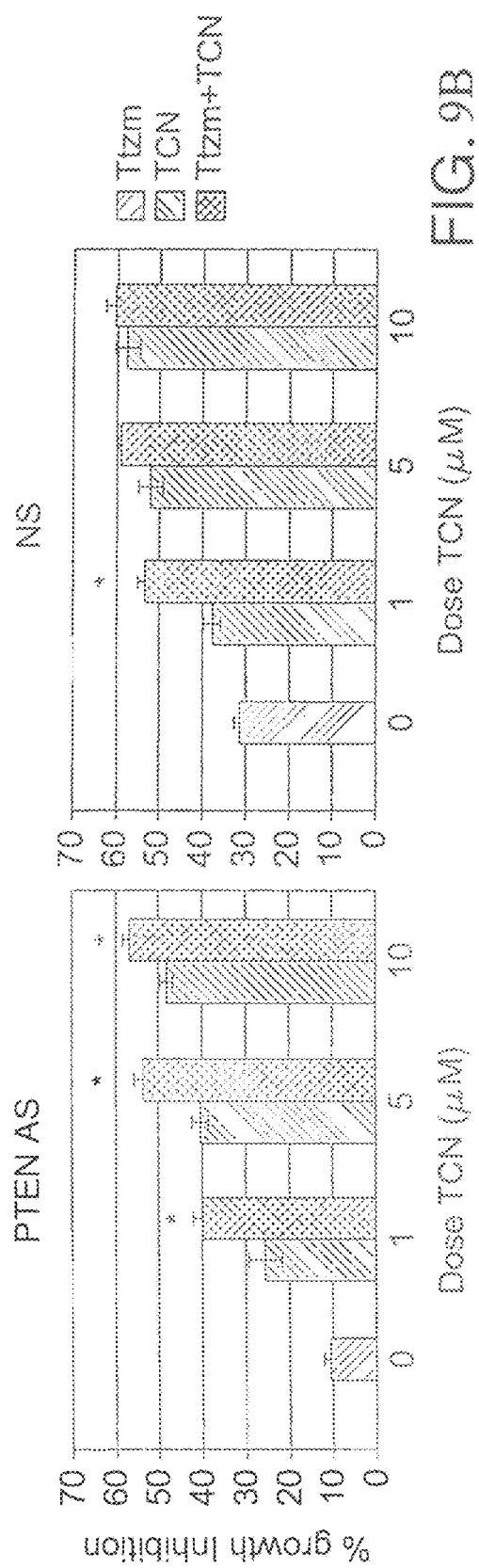
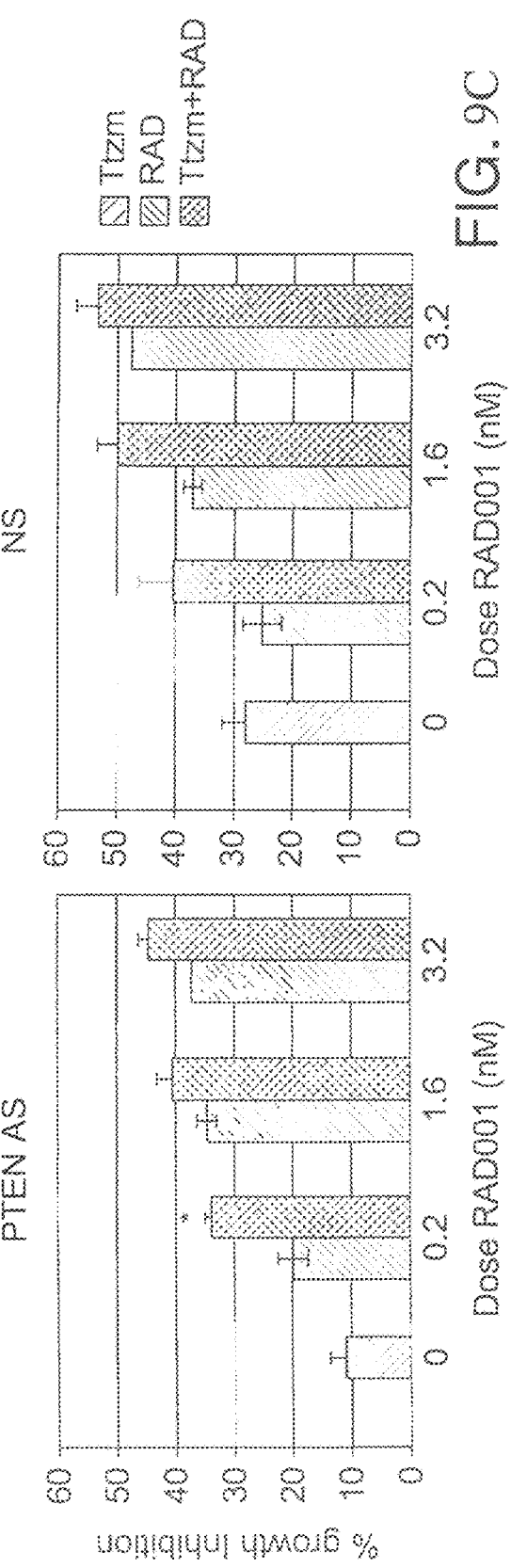
FIG. 9B
FIG. 9C

COMPOSITIONS INCLUDING TRICIRIBINE AND EPIDERMAL GROWTH FACTOR RECEPTOR INHIBITOR COMPOUNDS OR SALTS THEREOF AND METHODS OF USE THEREOF

This application is a continuation of U.S. application Ser. No. 14/998,352, which was filed Dec. 28, 2015, and is allowed, which is a continuation of U.S. application Ser. No. 14/092,323, which was filed Nov. 27, 2013, which issued as U.S. Pat. No. 9,265,783, which is a continuation of U.S. application Ser. No. 13/453,789, which was filed on Apr. 23, 2012, which issued as U.S. Pat. No. 8,673,867, which is a continuation of U.S. patent application Ser. No. 12/118,868, which was filed May 12, 2008, and was abandoned, which is a continuation-in-part of U.S. application Ser. No. 11/096,082, which was filed Mar. 29, 2005, which issued as U.S. Pat. No. 8,435,959, which claims the benefit of U.S. provisional patent application No. 60/557,599, which was filed Mar. 29, 2004, the disclosures of each of which is incorporated herein by reference in their entireties.

STATEMENT REGARDING FEDERALLY SPONSORED RESEARCH

This invention was made with government support CA077935 and CA089242 awarded by the National Institutes of Health. The government has certain rights to the invention.

1. FIELD OF THE INVENTION

This application relates to combination therapies including triciribine compounds and epidermal growth factor receptor inhibitor compounds, particularly erlotinib-like compounds and compositions with reduced toxicity for the treatment and prevention of tumors, cancer, and other disorders associated with abnormal cell proliferation.

2. BACKGROUND OF THE INVENTION

Cancer is an abnormal growth of cells. Cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumors, are clusters of cells that are capable of growing and dividing uncontrollably. Tumors can be benign (noncancerous) or malignant (cancerous). Benign tumors tend to grow slowly and do not spread. Malignant tumors can grow rapidly, invade and destroy nearby normal tissues, and spread throughout the body.

Cancers are classified according to the kind of fluid or tissue from which they originate, or according to the location in the body where they first developed. In addition, some cancers are of mixed types. Cancers can be grouped into five broad categories, carcinomas, sarcomas, lymphomas, leukemias, and myelomas, which indicate the tissue and blood classifications of the cancer. Carcinomas are cancers found in body tissue known as epithelial tissue that covers or lines surfaces of organs, glands, or body structures. For example, a cancer of the lining of the stomach is called a carcinoma. Many carcinomas affect organs or glands that are involved with secretion, such as breasts that produce milk. Carcinomas account for approximately eighty to ninety percent of all cancer cases. Sarcomas are malignant tumors growing from connective tissues, such as cartilage, fat, muscle, tendons, and bones. The most common sarcoma, a tumor on the bone, usually occurs in young adults. Examples of sarcoma include osteosarcoma (bone) and chondrosarcoma (cartilage). Lymphoma refers to a cancer that originates in the nodes or glands of the lymphatic system, whose job it is to produce white blood cells and clean body fluids, or in organs such as the brain and breast. Lymphomas are classified into two categories: Hodgkin's lymphoma and non-Hodgkin's lymphoma. Leukemia, also known as blood cancer, is a cancer of the bone marrow that keeps the marrow from producing normal red and white blood cells and platelets. White blood cells are needed to resist infection. Red blood cells are needed to prevent anemia. Platelets keep the body from easily bruising and bleeding. Examples of leukemia include acute myelogenous leukemia, chronic myelogenous leukemia, acute lymphocytic leukemia, and chronic lymphocytic leukemia. The terms myelogenous and lymphocytic indicate the type of cells that are involved. Finally, myelomas grow in the plasma cells of bone marrow. In some cases, the myeloma cells collect in one bone and form a single tumor, called a plasmacytoma. However, in other cases, the myeloma cells collect in many bones, forming many bone tumors. This is called multiple myeloma.

Tumor induction and progression are often the result of accumulated changes in the tumor-cell genome. Such changes can include inactivation of cell growth inhibiting genes, or tumor suppressor genes, as well as activation of cell growth promoting genes, or oncogenes. Hundreds of activated cellular oncogenes have been identified to date in animal models, however, only a small minority of these genes have proven to be relevant to human cancers (Weinberg et al., *Oncogenes and the Molecular Origins of Cancer*, 1989. Cold Spring Harbor, N.Y.; Stanbridge J. et al., Cell, 1990. 63: p 867-874; Godwin et al., in *Gynecological oncology: principles and practice*, Hoskins W. J., Perez C. A. and Young R. C. (eds.), 1992. pp 87-116, Lippincott, Philadelphia). The activation of oncogenes in human cancers can result from factors such as increased gene copy number or structural changes. These factors can cause numerous cellular effects, for example, they can result in overexpression of a gene product. Several oncogenes involved in human cancer can be activated through gene overexpression.

It has become apparent that the successive genetic aberrations acquired by cancer cells result in defects in regulatory signal transduction circuits that govern normal cell proliferation, differentiation and programmed cell death (Hanahan, D. and Weinberg R. A., Cell, 2000. 100(1): p. 57-700). This in turn results in fundamental defects in cell physiology which dictate malignancy. These defects include: a) self sufficiency in growth signals (i.e. overexpression of growth factor receptor tyrosine kinases such as EGFR and aberrant activation of downstream signal transduction pathways such as Ras/Raf/Mek/Erk 1/2 and Ras/PI3K/Akt), b) resistance to anti-growth signals (i.e. lower expression of TGFβ and its receptor), c) evading apoptosis (i.e. loss of proapoptotic p53; overexpression of pro-survival Bcl-2; hyperactivation of survival pathways such as those mediated by PI3K/Akt), d) sustained angiogenesis (i.e. high levels of secretion of VEGF) and f) tissue invasion and metastasis (i.e. extracellular proteases and prometastatic integrins) (Hanahan, D. and Weinberg R. A., Cell, 2000. 100(1): p. 57-700).

Receptor tyrosine kinases such as EGFR, ErbB2, VEGFR and insulin-like growth factor I receptor (IGF-1R) are intimately involved in the development of many human cancers including colorectal pancreatic, breast and ovarian cancers (Khaleghpour K. et al., Carcinogenesis, 2004. 25(2): p. 241-8; Sekharam M. et al., Cancer Res, 2003. 63(22): p. 7708-16). Binding of ligands such as EGF, VEGF and IGF-1 to their receptors promotes stimulation of the intrinsic tyrosine kinase activity, autophosphorylation of specific tyrosines in the cytoplasmic domain of the receptors and recruitment of signaling proteins that trigger a variety of complex signal transduction pathways (Olayioye M. A. et al., Embo J, 2000. 19(13): p. 3159-67; Porter A. C. and Vaillancourt R. R., Oncogene, 1998. 17(11 Reviews): p. 1343-52). This in turn leads to the activation of many tumor survival and oncogenic pathways such as the Ras/Raf/Mek/Erk1/2, JAK/STAT3 and PI3K/Akt pathways. Although all three pathways have been implicated in colon, pancreatic, breast and ovarian oncogenesis, those that are mediated by Akt have been shown to be critical in many steps of malignant transformation including cell proliferation, anti-apoptosis/survival, invasion and metastasis and angiogenesis (Datta S. R. et al., Genes Dev, 1999. 13(22): p. 2905-27).

Akt is a serine/threonine protein kinase (also known as PKB), which has 3 family members Akt1, Akt2 and Akt3. Stimulation of cells with growth or survival factors results in recruitment to the receptors of the lipid kinase phosphoinositide-3-OH-kinase (PI3K) which phosphorylates phosphoinositol-4,5-biphosphate ($PIP_2$) to $PIP_3$ which recruits Akt to the plasma membrane where it can be activated by phosphorylation on Thr308 andSer473 (Akt1), Thr308 andSer474 (Akt2) and Thr308 andSer472 (Akt3) (Datta S. R. et al., Genes Dev, 1999. 13(22): p. 2905-27). Thus, PI3K activates Akt by phosphorylating PIP2 and converting to PIP3. The phosphatase PTEN dephosphorylates PIP3 to PIP2 and hence prevents the activation of Akt.

The majority of human cancers contain hyperactivated Akt (Datta S. R. et al., Genes Dev, 1999. 13(22): p. 2905-27; Bellacosa A. et al., Int J Cancer, 1995. 64(4): p. 280-5; Sun M. et al., Am J Pathol, 2001. 159(2): p. 431-7). In particular, Akt is overexpressed and/or hyperactivated in 57%, 32%, 27% and 36% of human colorectal, pancreatic, breast and ovarian cancers, respectivel (Roy H. K. et al., Carcinogenesis, 2002. 23(1): p. 201-5; Altomare D. A. et al., J Cell Biochem, 2003. 88(1): p. 470-6; Sun M. et al., Cancer Res, 2001. 61(16): p. 5985-91; Stal O. et al., Breast Cancer Res, 2003. 5(2): p. R37-44; Cheng J. Q. et al., Proc Natl Acad Sci USA, 1992. 89(19): p. 9267-71; Yuan Z. Q. et al., Oncogene, 2000. 19(19): p. 2324-30). Hyperactivation of Akt is due to amplification and/or overexpression of Akt itself as well as genetic alterations upstream of Akt including overexpression of receptor tyrosine kinases and/or their ligands and deletion of the phosphatase PTEN (Khaleghpour K. et al., Carcinogenesis, 2004. 25(2): p. 241-8; Sekharam M. et al., Cancer Res, 2003. 63(22): p. 7708-16; Cohen B. D. et al., Biochem Soc Symp, 1998. 63: p. 199-210; Muller W. J. et al., Biochem Soc Symp, 1998. 63: p. 149-57; Miller W. E. et al., J Virol, 1995. 69(7): p. 4390-8; Slamon D. J. et al., Science, 1987. 235(4785): p. 177-82; Andrulis I. L. et al., J Clin Oncol, 1998. 16(4): p. 1340-9). Proof-of-concept of the involvement of Akt in oncogenesis has been demonstrated preclinically by showing that ectopic expression of Akt induces malignant transformation and promotes cell survival (Sun M. et al., Am J Pathol, 2001. 159(2): p. 431-7; Cheng J. Q. et al., Oncogene, 1997. 14(23): p. 2793-801) and that disruption of Akt pathways inhibits cell growth and induces apoptosis (Jetzt A. et al. Cancer Res, 2003. 63(20): p. 6697-706).

Current treatments of cancer and related diseases have limited effectiveness and numerous serious unintended side effects. Despite demonstrated clinical efficacy of many anticancer drugs, severe systemic toxicity often halts the clinical development of promising chemotherapeutic agents. Further, overexpression of receptor tyrosine kinases such as EGFR and their ligands such as IGF-1, Akt overexpression and/or loss of PTEN (all of which result in hyperactivation of Akt) are associated with poor prognosis, resistance to chemotherapy and shortened survival time of cancer patients. Current research strategies emphasize the search for effective therapeutic modes with less risk.

Thus, a combination therapy including a triciribine compound and erlotinib-like compound hold promise as a potential therapy for treating tumors, cancer, and abnormal cell proliferation while synergistically reducing toxicity or adverse side effects caused by currently administered cancer compounds.

3. SUMMARY OF THE INVENTION

The present invention provides novel therapeutic regimens of triciribine, triciribine phosphate and related compounds in combination with one or more erlotinib-like compounds to treat tumors or cancer in a subject while limiting systemic toxicity. The invention is based on the discovery that tumors or cancers, which overexpress Akt kinase are particularly sensitive to the cytotoxic effects of TCN and related compounds and a synergistic affect would arise with a combination of erlotinib-like compounds. The inventors have determined, contrary to the prior art and experience, how to successfully use triciribine and one or more erlotinib-like compounds to treat tumors and cancer by one or a combination of (i) administering triciribine and erlotinib-like compounds to patients who exhibit enhanced sensitivity to the triciribine compound and or the erlotinib-like compounds; (ii) use of a described dosage level that minimizes the toxicity of the triciribine compound and/or erlotinib-like compounds but yet still exhibits efficacy; or (iii) use of a described dosage regimen that minimizes the toxicity of the triciribine compound and/or erlotinib-like compounds.

In one aspect of the present invention, the invention encompasses a composition including:

(i) a compound of Formula I-IV:

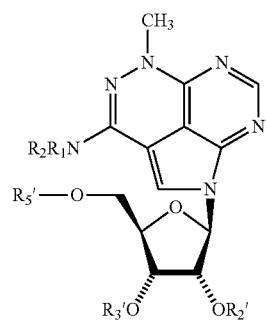

Formula I

-continued

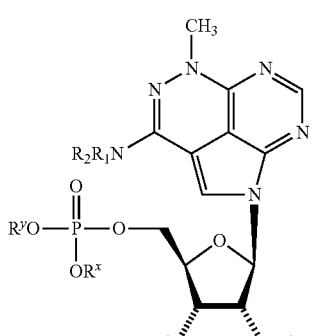
Formula II

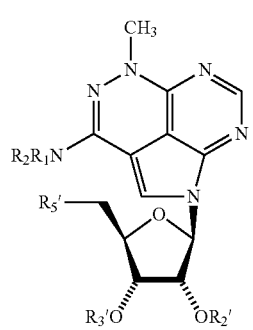
Formula III

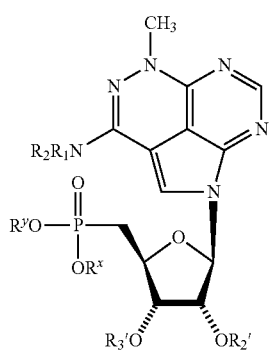
Formula IV wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein Rx and Ry are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

R1 and R2 each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl;

(ii) erlotinib-like compounds as in formula V:

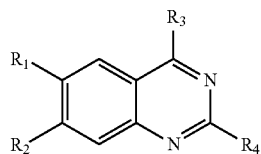
Formula V wherein each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine; and (iii) a pharmaceutically acceptable carrier.

In another embodiment, the invention encompasses a method of treating a tumor or cancer in a mammal including administering to the mammal an effective amount of a composition including:

(i) a compound of formula I-IV:

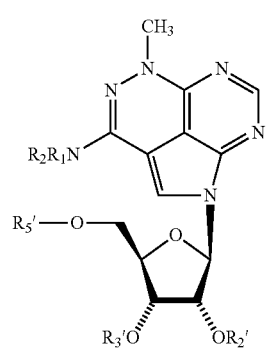
Formula I

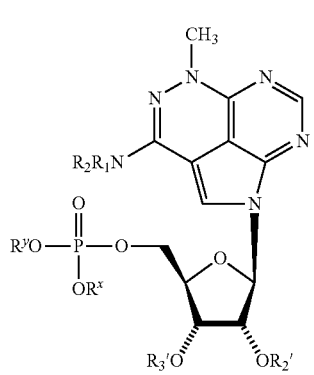
Formula II

Formula III

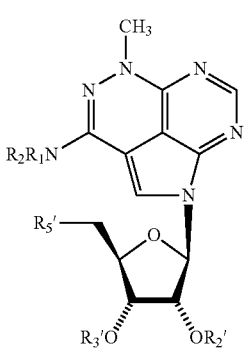

(ii) erlotinib-like compounds as in formula V:

Formula V

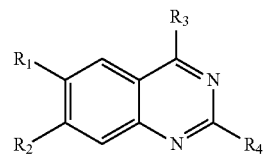

wherein
each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine.

Methods are useful to treat tumors and cancers that are particulary susceptible to the toxic effects of TCN, TCN-P and/or related compounds. In another embodiment, methods are provided for treating a tumor in a mammal, particularly a human that includes (i) obtaining a biological sample from the tumor; (ii) determining whether the tumor overexpresses an Akt kinase, and (iii) treating the tumor that overexpresses Akt kinase with triciribine, triciribine phosphate or a related compound in combination with one or more erlotinib-like compounds, as described herein. In another embodiment, the level of Akt kinase expression can be determined by assaying the tumor or cancer for the presence of a phosphorylated Akt kinase, for example, by using an antibody that can detect the phosphorylated form. In another embodiment, the level of Akt expression can be determined by assaying a tumor or cancer cells obtained from a subject and comparing the levels to a control tissue. In certain embodiments, the Akt can be overexpressed at least 2, 2.5, 3 or 5 fold in the cancer sample compared to the control. In certain embodiments, the overexpressed Akt kinase can be a hyperactivated and phosphorylated Akt kinase.

Formula IV

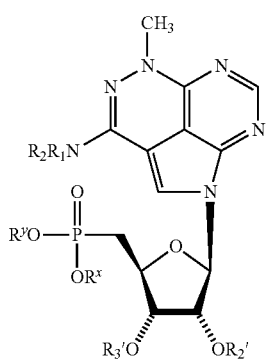

wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein Rx and Ry are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

R1 and R2 each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl; and In another aspect of the present invention, dosing regimens are provided that limit the toxic side effects of TCN and related compounds. In another embodiment, such dosing regimens minimize or eliminate toxic side effects, including, but not limited to, hepatoxicity, thrombocytopenia, hyperglycemia, vomiting, hypocalcemia, anemia, hypoalbunemia, myelosuppression, hypertriglyceridemia, hyperamylasemia, diarrhea, stomachitis and/or fever. In another embodiment, the administration of TCN, TCN-P or related compounds provides at least a partial, such as at least 15, 20 or 30%, or complete response in vivo in at least 15, 20, or 25% of the subjects.

In another embodiment, a method is provided to treat a subject who has been diagnosed with a tumor by administering to the subject an effective amount of TCN, TCN-P or a related compound and one or more erlotinib-like compounds according to a dosing schedule that includes administering the triciribine compound and erlotinib-like compounds approximately one time per week for approximately three weeks followed by a one week period wherein the triciribine compound and erlotinib-like compounds are not administered. In another embodiment, methods are provided to treat tumor or cancer in a subject by administering to the subject a dosing regimen of 10 mg/m2 or less of TCN, TCN-P or a related compound and one or more erlotinib-like compounds each one time per week. In another embodiment, the triciribine compound and one or more erlotinib-like compounds can be administered as a single bolus dose over a short period of time, for example, about 5, 10 or 15 minutes. In further embodiments, dosing schedules are provided in which the triciribine compound and one or more erlotinib-like compounds are administered via continuous infusion for at least 24, 48, 72, 96, or 120 hours. In certain embodiments, the continuous administration can be repeated at least once a week, once every two weeks and/or once a month. In other embodiments, the triciribine compound and one or more erlotinib-like compounds can be administered at least once every three weeks. In further embodiments, the compounds can be administered at least once a day for at least 2, 3, 4 or 5 days.

In further embodiments, the triciribine compound and one or more erlotinib-like compounds as disclosed herein can be administered to patients in an amount that is effective in causing tumor regression. The administration the triciribine compound and one or more erlotinib-like compounds can provide at least a partial, such as at least 15, 20 or 30%, or complete response in vivo in at least 15-20% of the subjects. In certain embodiments, at least 2, 5, 10, 15, 20, 30 or 50 mg/m2 of the triciribine compound and at least about 10, 25, 50, 75, 100, 150, 200, 250 or 500 mg one or more erlotinib-like compounds disclosed herein can be administered to a subject. The administration of the triciribine compound and one or more erlotinib-like compounds can be conducted according to any of therapeutic regimens disclosed herein. In particular embodiments, the dosing regimen can include administering less than 20 mg/m2 of the triciribine compound and one or more erlotinib-like compounds. In one embodiment, less than 10 mg/m2 of the triciribine compound and less than about 200 mg of one or more erlotinib-like compounds can be administered once a week. In further embodiments, dosages of or less than 2 mg/m2, 5 mg/m2, 10 mg/m2, and/or 15 mg/m2 of the triciribine compound and 10 mg, 20 mg, 50 mg, 100 mg, 150 mg, 200 mg, 250 mg, or 500 mg of one or more erlotinib-like compounds can be administered to a subject. In another embodiment, less than 10 mg/m2 of the triciribine compound and less than 150 mg of the erlotinib compound can be administered to a subject via continuous infusion for at least five days. In particular embodiments, the triciribine compound and one or more erlotinib-like compounds as disclosed herein can be used for the treatment of pancreatic, prostate, colo-rectal and/or ovarian cancer.

In another embodiment, the triciribine compound and one or more erlotinib-like compounds and/or therapeutic regimens of the present invention can be used to prevent and/or treat a carcinoma, sarcoma, lymphoma, leukemia, and/or myeloma. In other embodiments of the invention, the triciribine compound and one or more erlotinib-like compounds can be used to treat solid tumors. In still further embodiments, the triciribine compound and one or more erlotinib-like compounds and compositions disclosed herein can be used for the treatment of a tumor or cancer, such as, but not limited to cancer of the following organs or tissues: breast, prostate, bone, lung, colon, including, but not limited to colorectal, urinary, bladder, non-Hodgkin lymphoma, melanoma, kidney, renal, pancreas, pharnx, thyroid, stomach, brain, and/or ovaries. In a particular embodiment, the triciribine compound and one or more erlotinib-like compounds can be used for the treatment of pancreatic, breast, colorectal and/or ovarian cancer. In further embodiments of the present invention, the triciribine compound and one or more erlotinib-like compounds disclosed herein can be used in the treatment of angiogenesis-related diseases. In certain embodiments, methods are provided to treat leukemia via continuous infusion of, the triciribine compound and one or more erlotinib-like compounds via continuous infusion for at least 24, 48, 72 or 96 hours. In other embodiments, the continuous infusion can be repeated, for example, at least once every two, three or four weeks.

In a particular embodiment, there is provided a method for the treatment of tumors, cancer, and others disorders associated with an abnormal cell proliferation in a host, the method includes administering to the host an effect amount of the triciribine compound and one or more erlotinib-like compounds optionally in combination with a pharmaceutically acceptable carrier.

In one aspect, the triciribine compound and one or more erlotinib-like compounds and compositions can be administered in combination and can form part of the same composition, or be provided as a separate composition for administration at the same time or a different time.

In other embodiments, the triciribine compound and one or more Erlotinib-like compounds as disclosed herein can be used to treat tumors or cancers resistant to one or more known anti-cancer drugs, including the embodiments of tumors or cancers and compounds disclosed herein. In one embodiment, the triciribine compound and one or more erlotinib-like compounds as disclosed herein is administered in an effective amount for the treatment of a patient with a drug resistant tumor or cancer, for example, multidrug resistant tumors or cancer including, but not limited to, those resistant to taxol alone, rapamycin, tamoxifen, cisplatin, and/or gefitinib (iressa).

In certain embodiments, a method is provided including administering to a host in need thereof an effective amount of a triciribine compound and one or more erlotinib-like compounds disclosed herein, or pharmaceutical composition including a triciribine compound and one or more erlotinib-like compounds, in an effective amount for the treatment of the treatment of tumors, cancer, and others disorders associated with an abnormal cell proliferation in a host.

In another embodiment, a method for the treatment of a tumor or cancer is provided including an effective amount of a compound disclosed herein, or a salt, isomer, prodrug or ester thereof, to an individual in need thereof, wherein the cancer is for example, carcinoma, sarcoma, lymphoma, leukemia, or myeloma. The compound, or salt, isomer, prodrug or ester thereof, is optionally provided in a pharmaceutically acceptable composition including the appropriate carriers, such as water, which is formulated for the desired route of administration to an individual in need thereof. Optionally the compound is administered in combination or alternation with at least one additional therapeutic agent for the treatment of tumors or cancer.

Also within the scope of the invention is the use of a compound disclosed herein or a salt, prodrug or ester thereof in the treatment of a tumor or cancer, optionally in a pharmaceutically acceptable carrier; and the use of a triciribine compound and one or more erlotinib-like compounds disclosed herein or a salt, prodrug or ester thereof in the manufacture of a medicament for the treatment of cancer or tumor, optionally in a pharmaceutically acceptable carrier.

4. BRIEF DESCRIPTION OF THE DRAWINGS

FIG. 1A-FIG. 1D demonstrates the identification of API-2 (triciribine) as a candidate of Akt inhibitor from the NCI Diversity Set. FIG. 1A illustrates the chemical structure of API-2 (triciribine). FIG. 1B demonstrates that API-2 inhibits phosphorylation levels of AKT2 in AKT2-transformed NIH3T3 cells. Wile type AKT2-transformed NIH3T3 cells were treated with API-2 (1 µM) for indicated times and subjected to immunoblotting analysis with anti-phospho-Akt-T308 and -S473 antibodies (top and middle panels). The bottom panel shows expression of total AKT2. In FIG. 1C, it is shown that API-2 inhibits three isoforms of Akt. HEK293 cells were transfected with HA-Akt1, -AKT2 and -AKT3 and treated with API-2 (1 µM) or wortmannin (15 µM) prior to EGF stimulation, the cells were lysed and immunoprecipitated with anti-HA antibody. The immunoprecipitates were subjected to in vitro kinase assay (top) and immunoblotting analysis with anti-phospho-Akt-T308 (bottom) antibody. Middle panel shows expression of transfected Akt1, AKT2 and AKT3. FIG. 1D illustrates that API-2 did not inhibit Akt in vitro. In vitro kinase assay of constitutively active AKT2 recombinant protein in a kinase buffer containing 1 µM API-2 (lane 3).

Figure 2B:
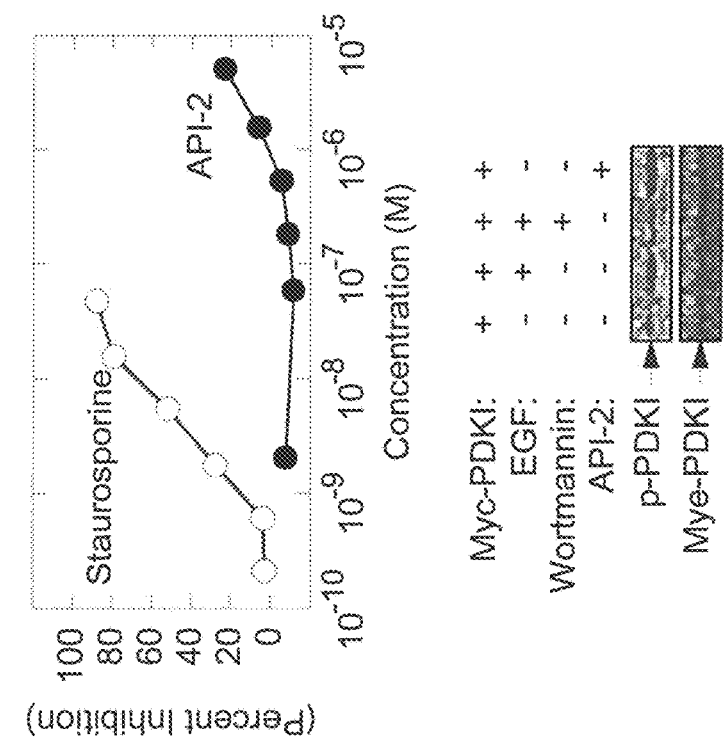
Figure 2A:
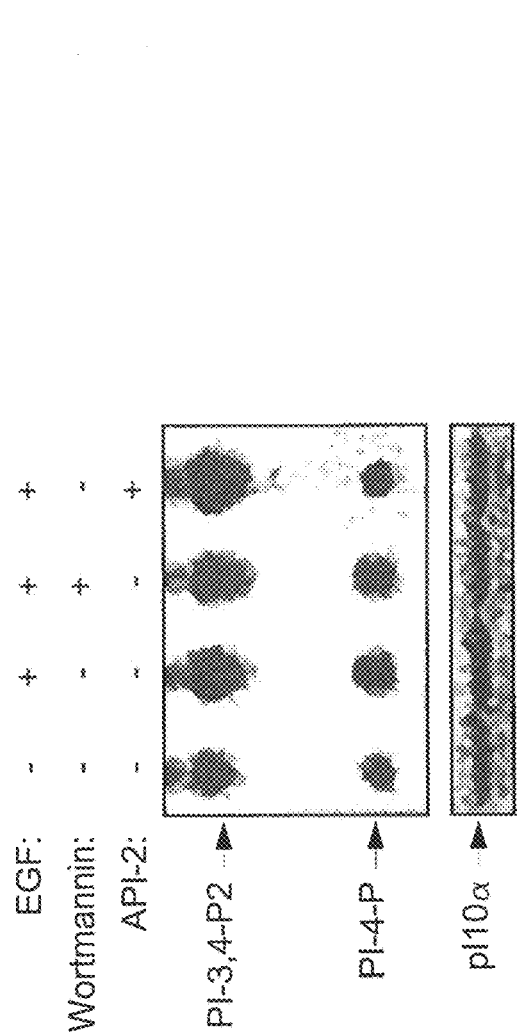
Figure 2C:
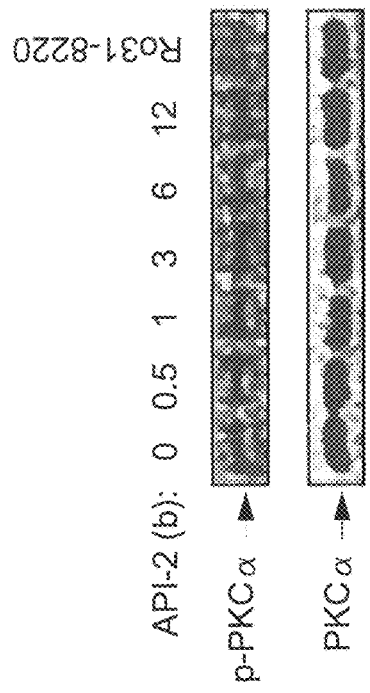
Figure 2D:
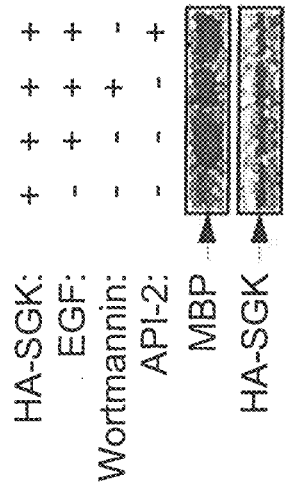
Figure 2F:
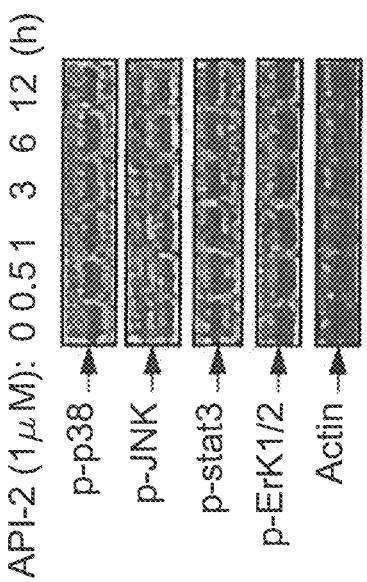
Figure 2E:
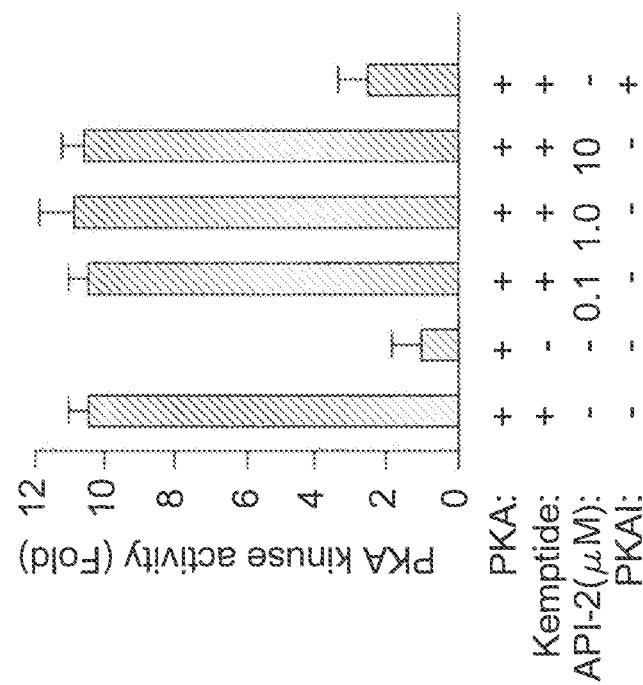

FIG. 2A-FIG. 2F demonstrates that API-2 does not inhibit PI3K, PDK1 and the closely related members of AGC kinase family. FIG. 2A demonstrates an in vitro PI3K kinase assay. HEK293 cells were serum-starved and treated with API-2 (1 µM) or Wortmannin (15 µM) fro 30 minutes prior to EGF stimulation. Cells were lysed and immunoprecipitated with anti-p110α antibody. The immunoprecipitates were subjected to in vitro kinase assay using PI-4-P as substrate. FIG. 2B illustrates the effect of API-2 on in vitro PDK1 activation (top panel), closed circles show inhibition by API-2. Open circles show inhibition by the positive control staurosporine, which is a potent PDK1 inhibitor (IC50=5 nM). Bottom panels are immunoblotting analysis of HEK293 cells that were transfected with Myc-PDK1 and treated with wortmannin or API-2 prior to EGF stimulation. The immunoblots were detected with indicated antibodies. FIG. 2C illustrates an immunoblot analysis of phosphorylation levels of PKC☐ with anti-phospho-PKCα☐T638 (top) and total PKCa (bottom) antibodies following treatment with API-2 or a non-selective PKC inhibitor Ro31-8220. FIG. 2D shows an in vitro SGK kinase assay. HEK293 cells were transfected with HA-SGK and treated with API-2 or wortmannin prior to EGF stimulation. In vitro kinase was performed with HA-SGK immunoprecipitates using MBP as substrate (top). Bottom panel shows the expression of transfected HA-SGK. FIG. 2E illustrates the results of a PKA kinase assay. Immuno-purified PKA was incubated in ADB buffer (Upstate Biotechnology Inc) containing indicated inhibitors (API-2 or PKAI) and substrate Kemptide. The kinase activity was quantified. In FIG. 2F, a western blot is shown. OVCAR3 cells were treated with API-2 for indicated times. Cell lysates were immunoblotted with indicated anti-phospho-antibodies (panels 1-4) and anti-actin antibody (bottom).

Figures 3, 3B, 4, 5, 6, 7, 8, 9, 10:
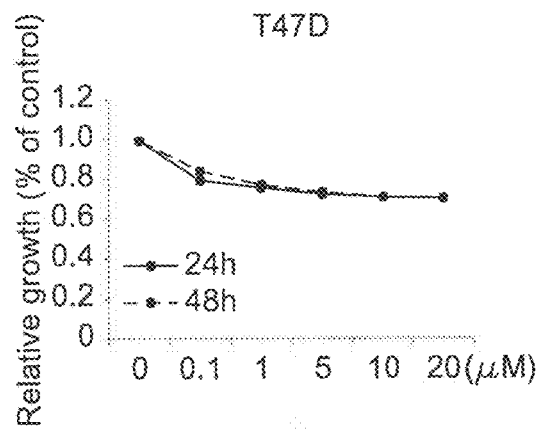
Figures 3, 3B, 4, 5, 6, 7, 8, 9, 10, 11:
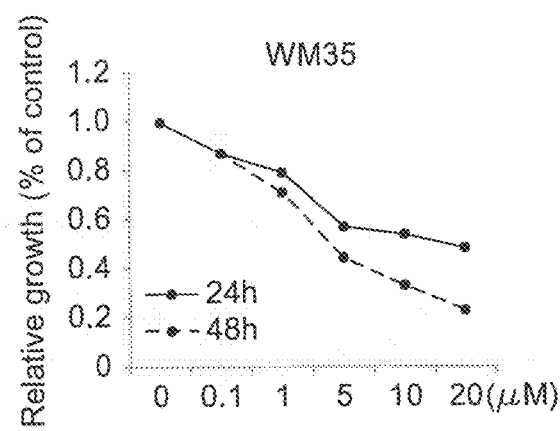
Figures 3, 3B, 4, 5, 6, 7, 8, 9, 10, 11, 12:
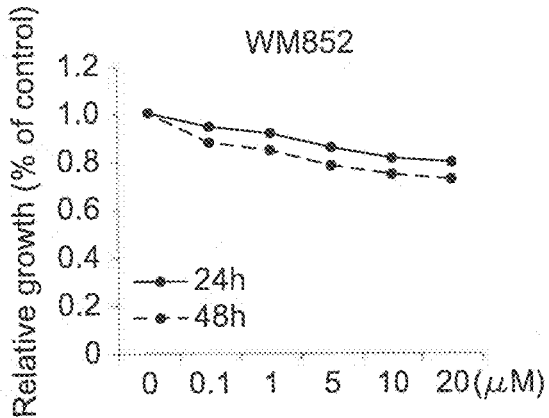
Figures 1, 3C:
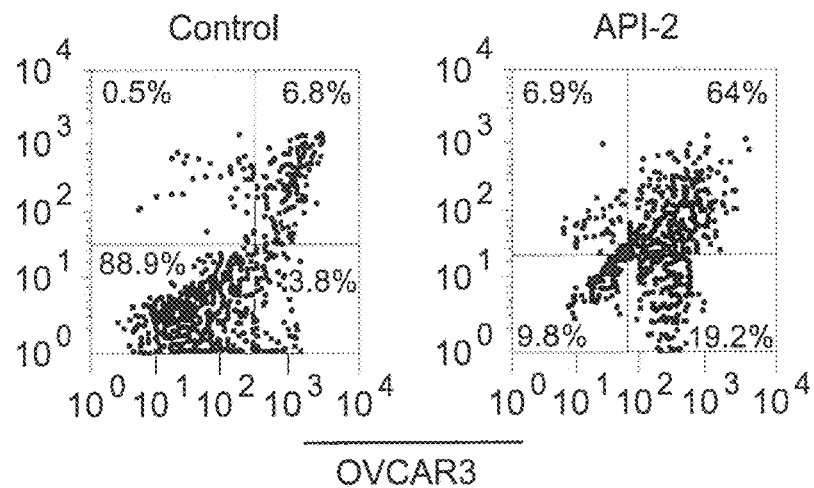
Figures 2, 3C:
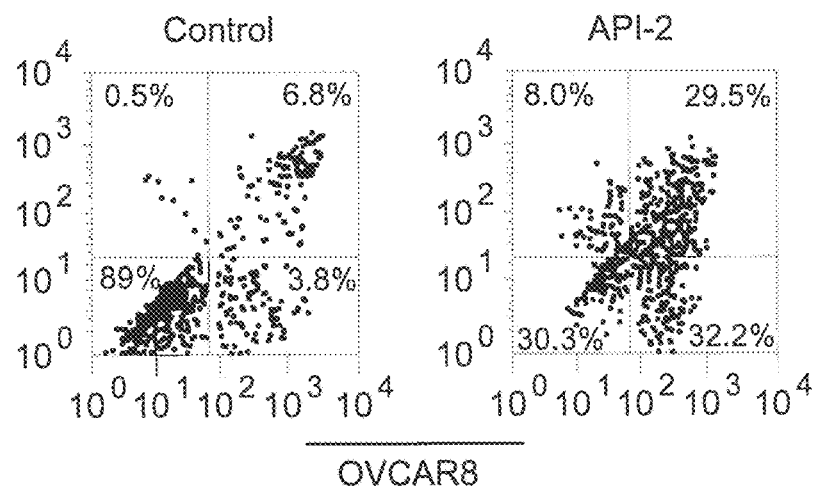
Figures 3, 3C:
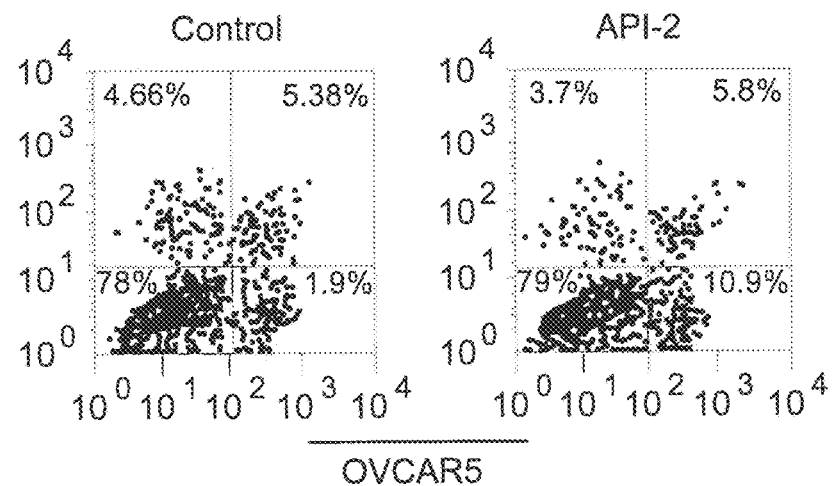

FIG. 3A-FIG. 3C-7 demonstrates that API-2 inhibits Akt activity and cell growth and induces apoptosis in human cancer cells with elevated Akt. FIG. 3A is a western blot, following treatment with API-2, phosphorylation levels of Akt were detected with anti-phospho-Akt-T308 antibody in indicated human cancer cell lines. The blots were reprobed with anti-total Akt antibody (bottom panels). In FIG. 3B, a cell proliferation assay is shown. Cell lines as indicated in the figure were treated with different doses of API-2 for 24 h and 48 h and then analyzed with CellTiter 96 Cell Proliferation Assay kit (Promega). FIG. 3C provides an apoptosis analysis. Cells were treated with API-2 and stained with annexin V and PI and analyzed by FACScan.

Figure 4A:
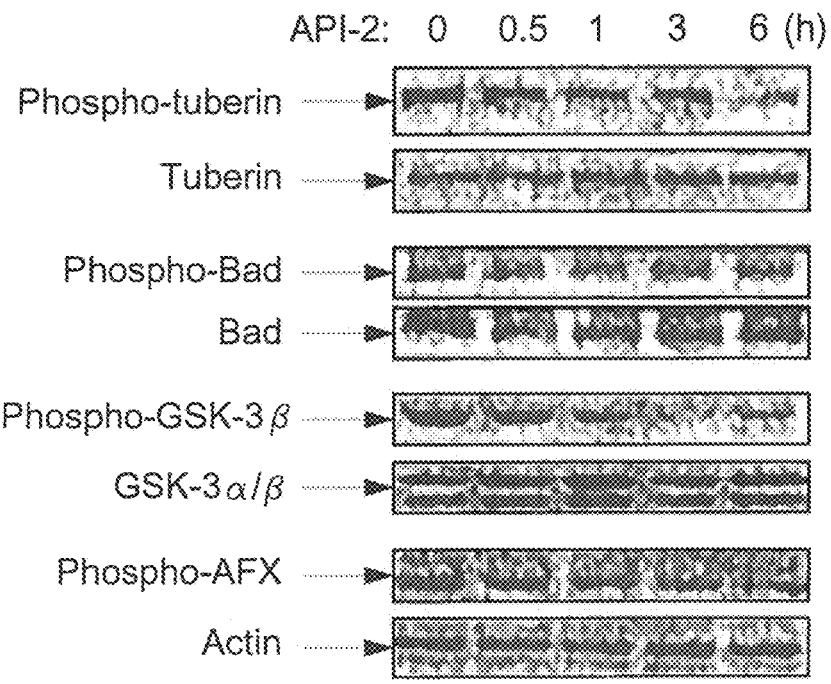
Figure 4C:
Figure 4E:
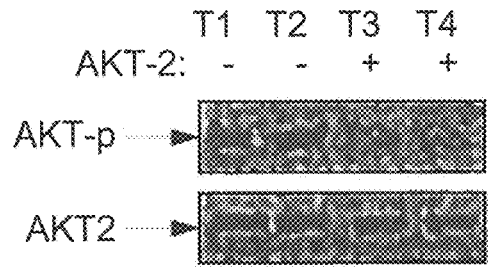
Figure 4D:
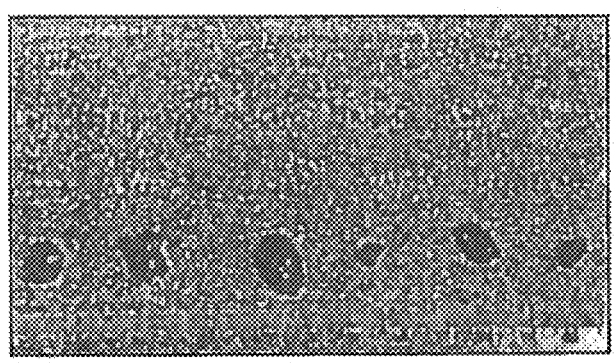
Figure 5:
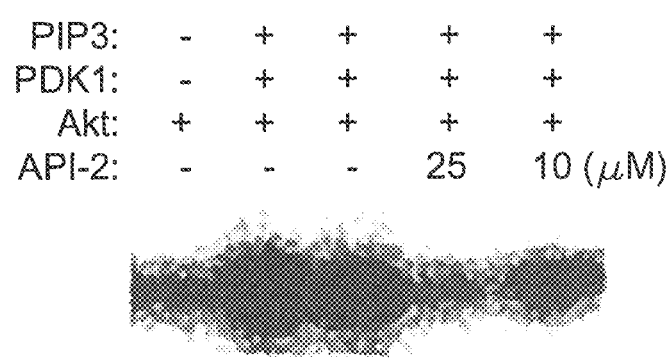
Figure 10:
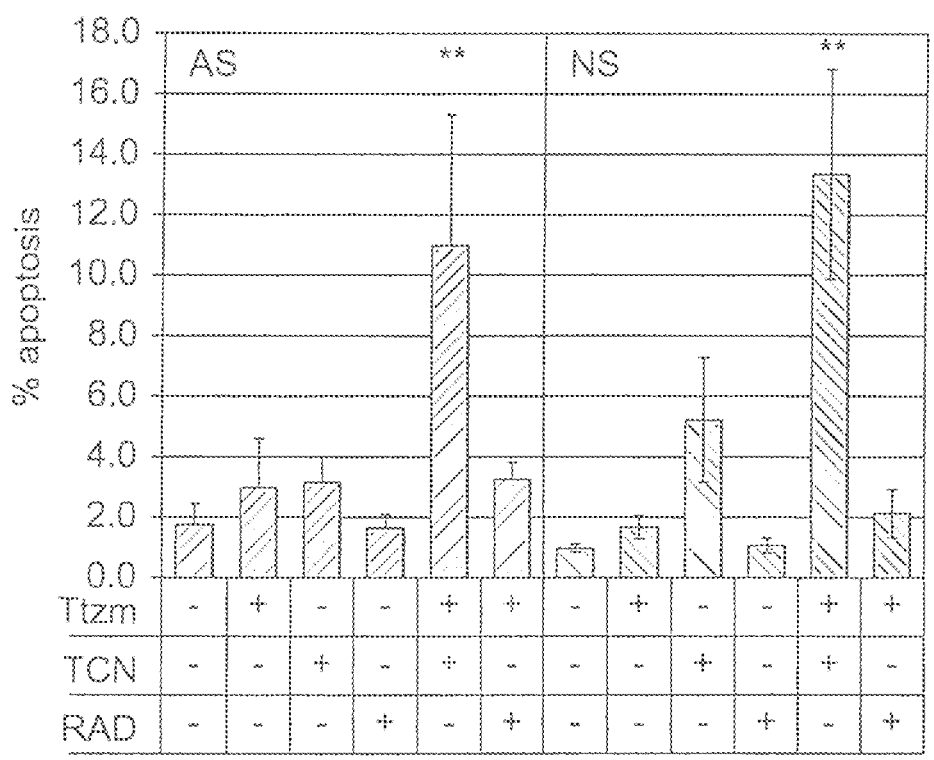

FIG. 4A-FIG. 4E shows that API-2 inhibits downstream targets of Akt and exhibits anti-tumor activity in cancer cell lines with elevated Akt in mouse xenograft. In FIG. 4A, it is demonstrated that API-2 inhibits Akt phosphorylation of tuberin, Bad, AFX and GSK-3β. Following treatment with API-2, OVAR3 cells were lysed and immunoblotted with indicated antibodies. FIG. 4B shows that API-2 inhibits tumor growth. Tumor cells were subcutaneously injected into nude mice with low level of Akt cells on left side and elevated level of Akt cells on right side. When the tumors reached an average size of about 100-150 mm$^3$, animals were treated with either vehicle or 1 mg/kg/day API-2. Each measurement represents an average of 10 tumors. FIG. 4C illustrates a representation of the mice with OVCAR3 (right) and OVCAR5 (left) xenograft treated with API-2 or vehicle (control). FIG. 4D shows examples of tumor size (bottom) and weight (top) at the end of experiment. In FIG. 4E, immunoblot analysis of tumor lysates was performed with anti-phospho-Akt-S473 (top) and anti-AKT2 (bottom) antibodies in OVCAR-3-derived tumors that were treated (T3 and T4) and untreated (T1 and T2) with API-2.

FIG. 5 shows that API-2 (triciribine) inhibits Akt kinase activity in vitro. In vitro kinase assay was performed with recombinant of PDK1 and Akt in a kinase buffer containing phosphatidylinositol-3,4,5-P3 (PIP3), API-2 and histone H2B as substrate. After incubation of 30 min, the reactions were separated by SDS-PAGE and exposed in a film.

FIG. 6A-FIG. 6D provides the mRNA and amino acid sequence of human Akt1, restriction enzyme sites are also noted.

FIG. 7A-FIG. 7D provides the mRNA and amino acid sequence of human Akt2 restriction enzyme sites are also noted.

FIG. 8A-FIG. 8D provides the mRNA and amino acid sequence of human Akt3 restriction enzyme sites are also noted.

FIG. 9A-FIG. 9C shows growth inhibition by the combination of trastuzumab and Akt/mTOR pathway inhibitors. PTEN anti-sense or non-specific oligonucleotide transfected BT474.m1 cells were treated with inhibitors of the Akt/mTOR pathway alone or in combination with trastuzumab and the relative cell growth was assessed. FIG. 9A shows a panel of Akt/mTOR inhibitors. Growth inhibition was assessed in PTEN AS transfected BT474.m1 cells. The doses shown are: Triciribine (TCN) 1 µM; RAD001 0.2 nM; QLT0267 10 µM; KP 372-1 0.05 µM; 4ADPIB 5 µM; Edelfosine 7.5 µM; and trastuzumab (Ttzm) 2 µg/ml. The standard deviation (SD) in the percent growth inhibition is indicated. Results shown are the combined data from 2-3 experiments with triplicates of each treatment within each experiment. FIG. 9B shows TCN inhibits cell growth in combination with trastuzumab. BT474.m1 cells were transfected with PTEN AS oligonucleotide or non-specific (NS) oligonucleotide, treated with trastuzumab and TCN, alone and in combination, at multiple doses of TCN and assayed for growth inhibition. Trastuzumab was administered at a single concentration. FIG. 7C shows RAD001 inhibits cell growth in combination with trastuzumab. BT474.m1 cells were transfected with PTEN AS oligonucleotide or non-specific (NS) oligonucleotide, treated with trastuzumab and RAD001, alone and in combination, at multiple doses of RAD001 and assayed for growth inhibition. For FIGS. 9B and 9C: * indicates a significant difference in growth inhibition following combination treatment as compared to either trastuzumab or TCN/TAD001 alone. P<0.05 was considered significant. Error bars depict the SEM.

FIG. 10 shows the synergistic effects on apoptosis. Twenty-four hours after plating, PTEN AS and NS transfected BT474.m1 cells were treated as indicated with trastuzumab (Ttzm), TCN and/or RAD001 at the following concentrations: trastuzumab 2 µg/ml; triciribine 2.5 µM; RAD001 0.4 nM. Apo-BrdU Tunel assays were performed to assess apoptosis. The experiment was performed 3 times and the data shown is the mean apoptosis. Error bars depite the standard deviation. Trastuzumab+triciribine treatment significantly induced apoptosis (p<0.01) as compared with all other treatments.

Figure 11A:
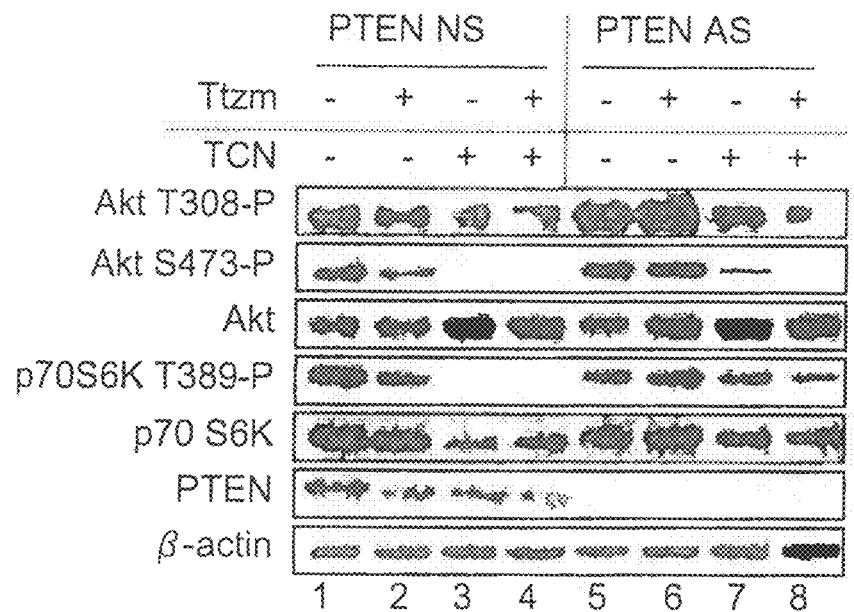
Figure 11B:
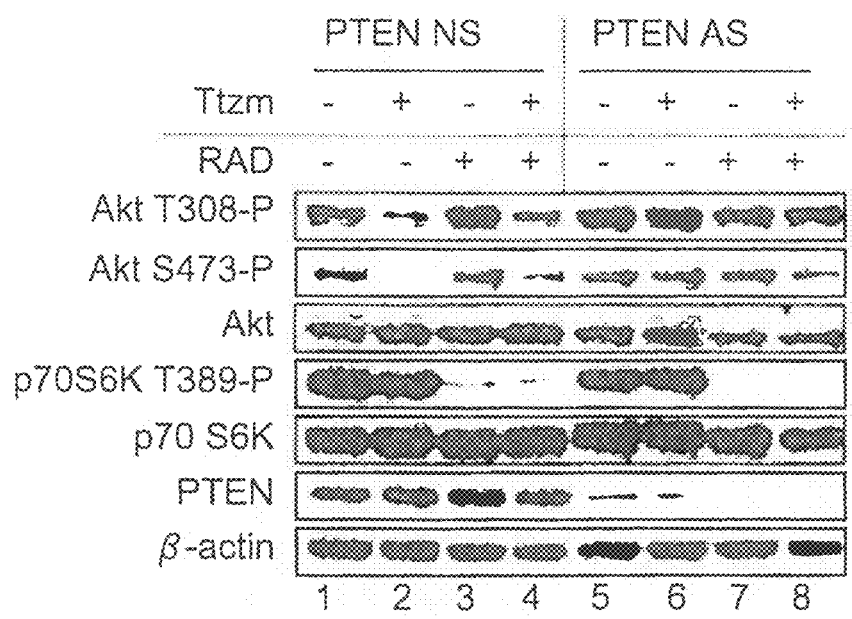

FIG. 11A-FIG. 11B shows inhibition of Akt and p70S6K activity. To evaluate the effects of these drugs on the Akt/mTOR pathway, PTEN AS and NS oligonucleotides were transfected int BT474.m1 cells. Two days later, the cells were treated for 2 hours with trastuzumab and triciribine (TCN) (FIG. 11A) or trastuzumab and RAD001 (FIG. 11B). Total cell lysates were collected, separated by SDS-PAGE and immunoblotted as indicated. The concentration of trastuzumab was 2 µg/ml, triciribine was 2.5 µM and RAD001 was 0.4 nM. The experiments were repeated at least twice to insure that results were reproducible.

Figure 12B:
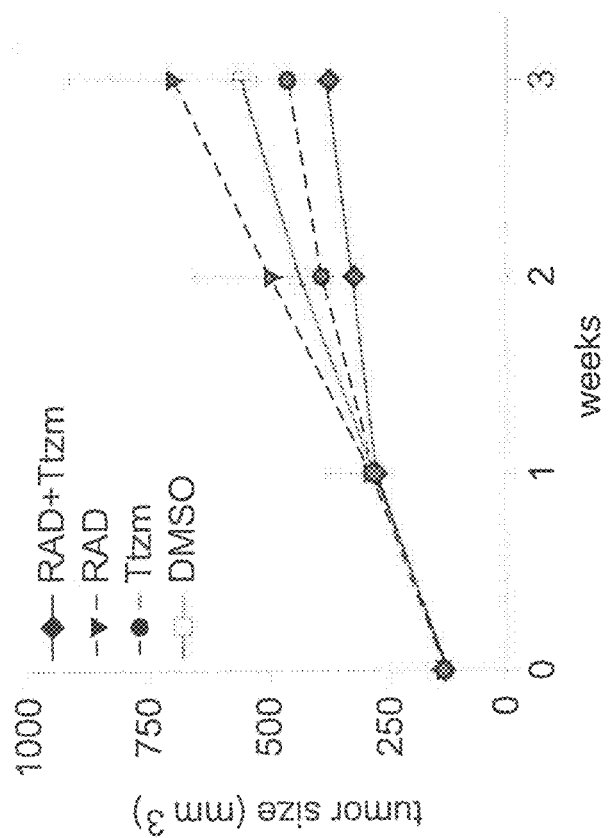
Figure 12A:
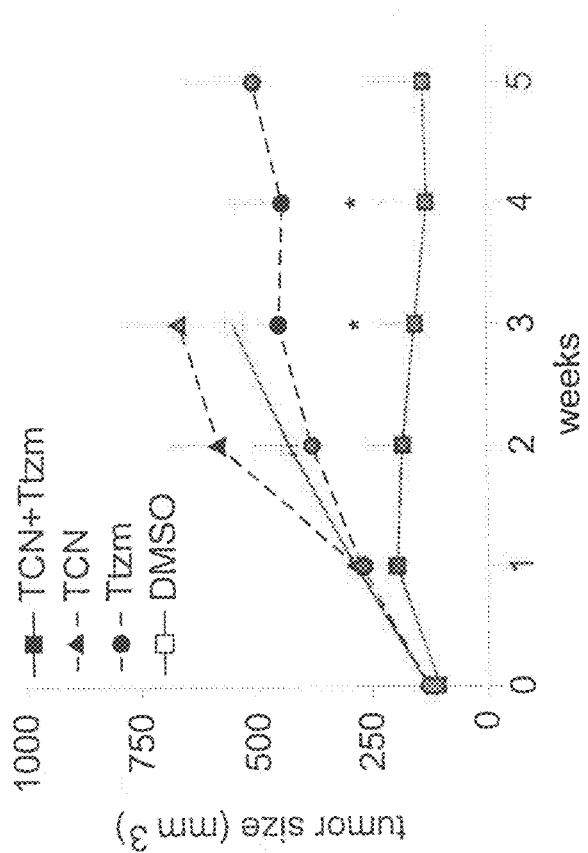

FIG. 12A-FIG. 12B shoes combination treatments inhibited tumor growth in a SCID mice xenograft model. SCID mice received BT474.m1 breast cancer cell xenografts in mammary fat pad. The xenografts grew for 3 weeks to generate tumors with an average size of 100-150 mm$^3$. PTEN antisense oligonucleotides, trastuzumab, triciribine (FIG. 12A) and RAD001 (FIG. 12B) were administered. The tumors were measured twice weekly with calipers and tumor size was averaged for each treatment group. Error bars denote the standard error of the mean. * indicates a significant difference in growth inhibition following combination treatment as compared to either trastuzumab (Ttzm), TCN or DMSO alone. P<0.05 was considered significant.

5. DETAILED DESCRIPTION OF THE INVENTION

The inventors have determined, contrary to the prior art and experience, how to successfully use triciribine compounds in combination with one or more erlotinib-like compounds to treat tumors and cancer by one or a combination of (i) administering triciribine and one or more erlotinib-like compounds only to patients which according to a diagnostic test described below, exhibit enhanced sensitivity to the triciribine compound and/or the erlotinib-like compounds; (ii) using a described dosage level that minimizes the toxicity of the triciribine compound and/or the erlotinib-like compounds but yet still exhibits efficacy; or (iii) using a described dosage regimen that minimizes the toxicity of the triciribine compound and/or the erlotinib-like compounds.

5.1. Definitions

As used herein, the term "compounds of the invention" refers to compounds disclosed herein including compounds of formula I-VIII, and combinations thereof.

As used herein, the terms "cancer" and "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

The term alkyl, as used herein, unless otherwise specified, includes a saturated straight, branched, or cyclic, primary, secondary, or tertiary hydrocarbon of for example $C_1$ to $C_{24}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl is optionally substituted, e.g., with one or more substituents such as halo (F, Cl, Br or I), (e.g. $CF_3$, 2-Br-ethyl, $CH_2F$, $CH_2Cl$, $CH_2CF_3$ or $CF_2CF_3$), hydroxyl (e.g. $CH_2OH$), amino (e.g. $CH_2NH_2$, $CH_2NHCH_3$ or $CH_2N(CH_3)_2$), alkylamino, arylamino, alkoxy, aryloxy, nitro, azido (e.g. $CH_2N_3$), cyano (e.g. $CH_2CN$), sulfonic acid, sulfate, phosphonic acid, phosphate, or phosphonate, either unprotected, or protected as necessary, as known to those skilled in the art, for example, as taught in Greene et al., *Protective Groups in Organic Synthesis*, 1991, 2d Ed., John Wiley and Sons, NY, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term alkylamino or arylamino includes an amino group that has one or two alkyl or aryl substituents, respectively.

The term amino acid includes naturally occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of a natural or synthetic amino acid, including but not limited to α, β, γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "protected" as used herein and unless otherwise defined includes a group that is added to an oxygen, nitrogen, sulfur or phosphorus atom to prevent its further reaction or for other purposes. A wide variety of oxygen and nitrogen protecting groups are known to those skilled in the art of organic synthesis (see Greene and Wuts, *Protective Groups in Organic Synthesis,* 1999, 3d Ed., John Wiley & Sons, Inc., NY).

The term aryl, as used herein, and unless otherwise specified, includes phenyl, biphenyl, or naphthyl, and preferably phenyl. The aryl group is optionally substituted with one or more moieties such as halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene et al., *Protective Groups in Organic Synthesis,* 1999, $3^{rd}$ Ed., John Wiley and Sons, NY.

The term alkaryl or alkylaryl includes an alkyl group with an aryl substituent. The term aralkyl or arylalkyl includes an aryl group with an alkyl substituent.

The term halo, as used herein, includes chloro, bromo, iodo, and fluoro.

The term acyl includes a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

As used herein, the term "substantially free of" or "substantially in the absence of" with respect to enantiomeric purity, refers to a composition that includes at least 85% or 90% by weight, preferably 95% to 98% by weight, and even more preferably 99% to 100% by weight, of the designated enantiomer. In a preferred embodiment, in the methods and compounds of this invention, the compounds are substantially free of other enantiomers.

Similarly, the term "isolated" refers to a compound composition that includes at least 85% or 90% by weight, preferably 95% to 98% by weight, and even more preferably 99% to 100% by weight, of the compound, the remainder comprising other chemical species or enantiomers.

The term "independently" is used herein to indicate that the variable, which is independently applied, varies independently from application to application. Thus, in a compound such as R″XYR″, wherein R″ is "independently carbon or nitrogen," both R″ can be carbon, both R″ can be nitrogen, or one R″ can be carbon and the other R″ nitrogen.

The term "pharmaceutically acceptable salt or prodrug" is used throughout the specification to describe any pharmaceutically acceptable form (such as an ester, phosphate ester, salt of an ester or a related group) of a compound, which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The term "subject" as used herein refers to an animal, preferably a mammal, most preferably a human. Mammals can include non-human mammals, including, but not limited to, pigs, sheep, goats, cows (bovine), deer, mules, horses, monkeys and other non-human primates, dogs, cats, rats, mice, rabbits or any other known or disclosed herein.

5.2. Compounds of the Invention

The present invention provides for the use of TCN, TCN-P and related compounds in combination with an erlotinib-like compound, for example, gefitinib, erlotinib or a salt thereof for use in particular therapeutic regimens for the treatment of proliferative disorders.

As used herein and unless otherwise indicated, the term "triciribine compounds" and "triciribine and related compounds" refers to compounds having the following structures:

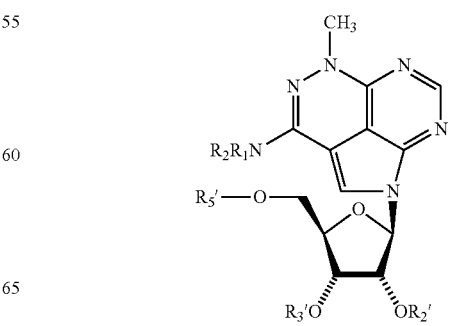

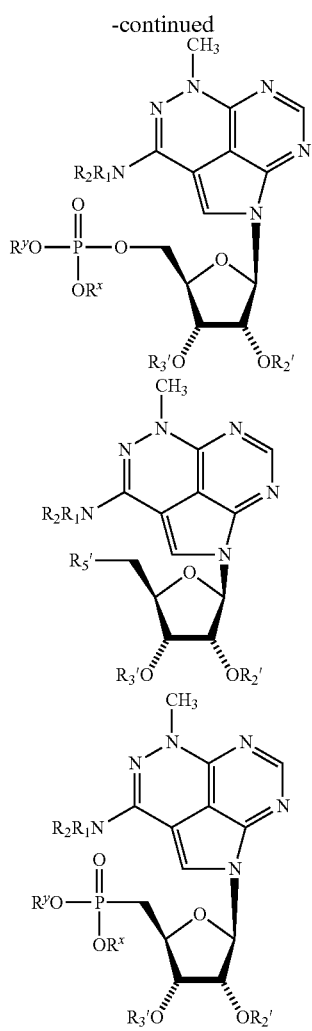

wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein $R^x$ and $R^y$ are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

$R_1$ and $R_2$ each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl.

In one embodiment, R2' and R3' are hydrogen. In another embodiment, R2' and R5' are hydrogen. In yet another embodiment, R2', R3' and R5' are hydrogen. In yet another embodiment, R2', R3', R5', R1 and R2 are hydrogen.

In another embodiment, the triciribine compound has the following structure:

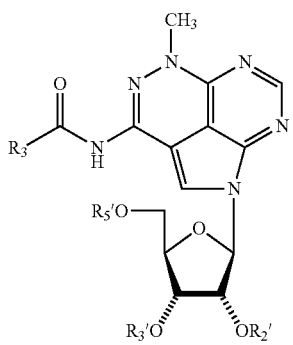

wherein $R_3$ is H, optionally substituted straight chained, branched or cyclic alkyl (including lower alkyl), alkenyl, or alkynyl, $NH_2$, $NHR^4$, $N(R^4)_2$, aryl, alkoxyalkyl, aryloxyalkyl, or substituted aryl; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl. In a subembodiment, $R_3$ is a straight chained C1-11 alkyl, iso-propyl, t-butyl, or phenyl.

In one embodiment, the triciribine compounds provided herein have the following structure:

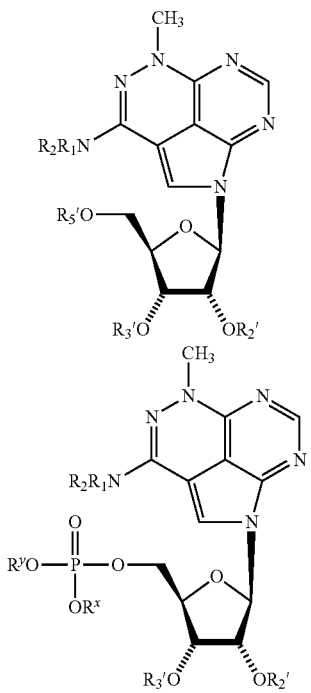

In another embodiment, the triciribine compounds provided herein have the following structure:

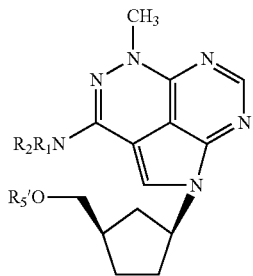

In another embodiment, the triciribine compounds provided herein have the following structure:

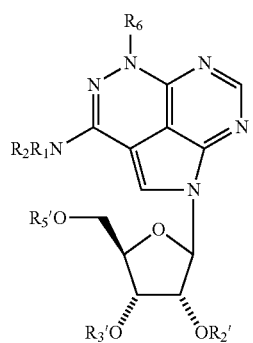

wherein $R_6$ is H, alkyl, (including lower alkyl) alkenyl, alkynyl, alkoxyalkyl, hydroxyalkyl, arylalkyl, cycloalkyl, $NH_2$, $NHR^4$, $NR^4R^4$, $CF_3$, $CH_2OH$, $CH_2F$, $CH_2Cl$, $CH_2CF_3$, $C(Y^3)_3$, $C(Y^3)_2C(Y^3)_3$, $C(=O)OH$, $C(=O)OR^4$, $C(=O)$-alkyl, $C(=O)$-aryl, $C(=O)$-alkoxyalkyl, $C(=O)NH_2$, $C(=O)NHR^4$, $C(=O)N(R^4)_2$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl.

In a subembodiment, $R_6$ is ethyl, $CH_2CH_2OH$, or $CH_2$-phenyl.

In another embodiment, the triciribine compounds provided herein have the following structure:

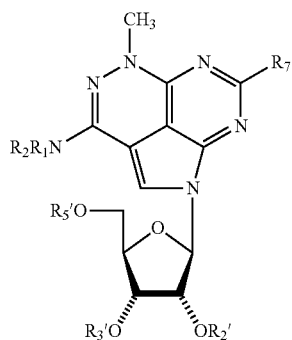

wherein $R_7$ is H, halo, alkyl (including lower alkyl), alkenyl, alkynyl, alkoxy, alkoxyalkyl, hydroxyalkyl, cycloalkyl, nitro, cyano, OH, $OR^4$, $NH_2$, $NHR^4$, $NR^4R^4$, SH, $SR^4$, $CF_3$, $CH_2OH$, $CH_2F$, $CH_2Cl$, $CH_2CF_3$, $C(Y^3)_3$, $C(Y^3)_2C(Y^3)_3$, $C(=O)OH$, $C(=O)OR^4$, $C(=O)$-alkyl, $C(=O)$-aryl, $C(=O)$-alkoxyalkyl, $C(=O)NH_2$, $C(=O)NHR^4$, $C(=O)N(R^4)_2$, or $N_3$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl.

In a subembodiment, $R_7$ is methyl, ethyl, phenyl, chloro or $NH_2$.

In another embodiment, the triciribine compounds provided herein have the following structure:

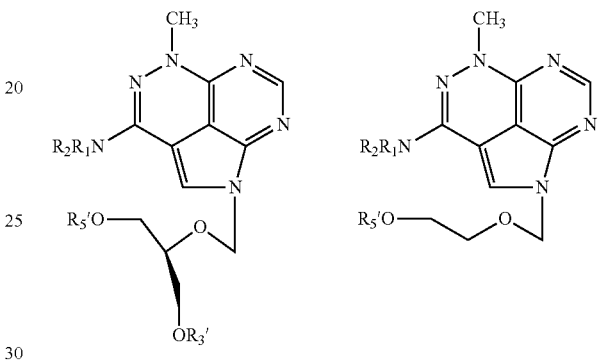

In another embodiment, the triciribine compounds provided herein have the following structure:

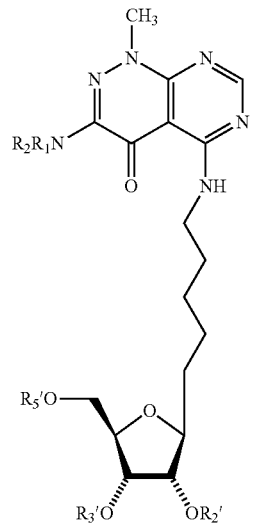

As used herein and unless otherwise indicated, the term "epidermal growth factor receptor inhibitor" refers to compounds that target the epidermal growth factor receptor (EGFR) tyrosine kinase, which is highly expressed and occasionally mutated in various forms of cancer. In certain embodiments, the compounds bind in a reversible fashion to the adenosine triphosphate (ATP) binding site of the receptor. In certain embodiments, two members of the EGFR family come together to form a homodimer. These then use the molecule of ATP to autophosphorylate each other, which causes a conformational change in their intracellular structure, exposing a further binding site for binding proteins that cause a signal cascade to the nucleus. By inhibiting the ATP, autophosphorylation is not possible and the signal is stopped. Illustrative examples of epidermal growth factor receptor inhibitor compounds include erlotinib-like compounds such as for example, gefitinib and erlotinib.

As used herein and unless otherwise indicated, the term "erlotinib-like compounds" refers to a compound of formula:

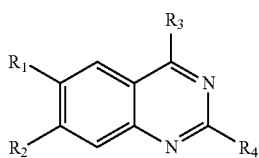

wherein each R1 and R2 is independently hydrogen, independently optionally substituted alkoxy, optionally substituted amine, aromatic amine, heteroaromatic amine, optionally substituted straight chained, branched or cyclic alkyl;

each R3 and R4 is independently hydrogen, independently optionally substituted aromatic amine, heteroaromatic amine, or cyclic amine. In an illustrative embodiment, the erlotinib-like compounds include, but are limited to, the following structure:

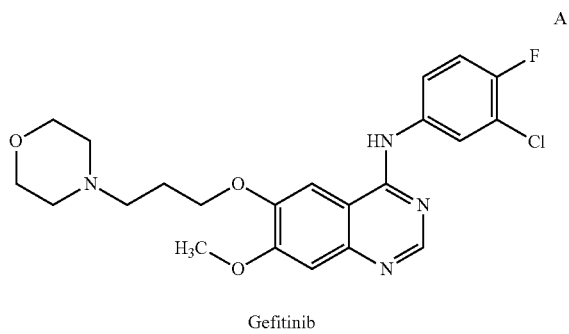

Gefitinib

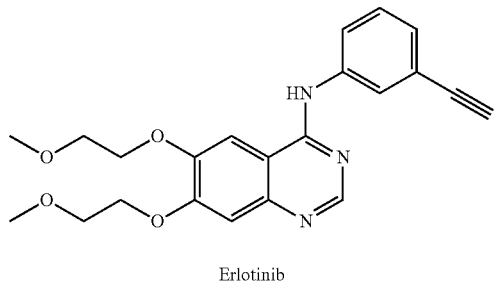

Erlotinib

It is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or steroisomeric form, or mixtures therof, which preferably possesses the useful properties described herein, it being well known in the art how to prepare optically active forms and how to determine activity using the standard tests described herein, or using other similar tests which are will known in the art. Examples of methods that can be used to obtain optical isomers of the compounds include the following:

(i) physical separation of crystals—a technique whereby macroscopic crystals of the individual enantiomers are manually separated. This technique can be used if crystals of the separate enantiomers exist, i.e., the material is a conglomerate, and the crystals are visually distinct;

(ii) simultaneous crystallization—a technique whereby the individual enantiomers are separately crystallized from a solution of the racemate, possible only if the latter is a conglomerate in the solid state;

(iii) enzymatic resolutions—a technique whereby partial or complete separation of a racemate by virtue of differing rates of reaction for the enantiomers with an enzyme (iv) enzymatic asymmetric synthesis—a synthetic technique whereby at least one step of the synthesis uses an enzymatic reaction to obtain an enantiomerically pure or enriched synthetic precursor of the desired enantiomer;

(v) chemical asymmetric synthesis—a synthetic technique whereby the desired enantiomer is synthesized from an achiral precursor under conditions that produce assymetry (i.e., chirality) in the product, which may be achieved using chiral catalysts or chiral auxiliaries;

(vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

(vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

(viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

(ix) enantiospecific synthesis from non-racemic precursors—a synthetic technique whereby the desired enantiomer is obtained from non-chiral starting materials and where the stereochemical integrity is not or is only minimally compromised over the course of the synthesis;

(x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

(xi) chiral gas chromatography—a technique whereby the racemate is volatilized and enantiomers are separated by virtue of their differing interactions in the gaseous mobile phase with a column containing a fixed non-racemic chiral adsorbent phase;

(xii) extraction with chiral solvents—a technique whereby the enantiomers are separated by virtue of preferential dissolution of one enantiomer into a particular chiral solvent;

(xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, triciribine, triciribine phosphate (TCN-P), triciribine 5'-phosphate (TCN-P), or the DMF adduct of triciribine (TCN-DMF) are provided. TCN can be synthesized by any technique known to one skilled in the art, for example, as described in Tetrahedron Letters, 1971. 49: p. 4757-4760. TCN-P can be prepared by any technique known to one skilled in the art, for example, as described in U.S. Pat. No. 4,123,524. The synthesis of TCN-DMF is described, for example, in INSERM, 1978. 81: p. 37-82. Other compounds related to TCN as described herein can be synthesized, for example, according to the methods disclosed in Gudmundsson K. S. et al., Nucleosides Nucleotides Nucleic Acids, 2001. 20(10-11): p. 1823-1830; Porcari A. R. et al., J Med Chem, 2000. 43(12): p. 2457-2463; Porcari A. R. et al., Nucleosides Nucleotides, 1999. 18(11-12): p. 2475-2497; Porcari A. R. et al., J Med Chem, 2000. 43(12): p. 2438-2448; Porcari A. R. et al., Nucleosides Nucleotides Nucleic Acids, 2003. 22(12): p. 2171-2193; Porcari A. R. et al., Nucleosides Nucleotides Nucleic Acids, 2004. 23(1-2): p. 31-39; Schweinsberg P. D. et al., Biochem Pharmacol, 1981. 30(18): p. 2521-2526; Smith K. L. et al., Bioorg Med Chem Lett, 2004. 14(13): p. 3517-3520; Townsend L. B. et al., Nucleic Acids Symp Ser, 1986. 1986(17): p. 41-44; and/or Wotring L. L. et al., Cancer Treat Rep, 1986. 70(4): p. 491-7.

5.3. Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleotides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 1995. 27: p. 1-17. Any of these can be used in combination with the disclosed nucleosides to achieve a desired effect.

In one embodiment, the triciribine or a related compound is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794, 5,194,654, 5,223,263, 5,256,641, 5,411,947, 5,463,092, 5,543,389, 5,543,390, 5,543,391, and 5,554,728, all of which are incorporated herein by reference.

Foreign patent applications that disclose lipophilic substituents that can be attached to the triciribine or a related compound, or lipophilic preparations, include WO 89/02733, WO 90/00555, WO 91/16920, WO 91/18914, WO 93/00910, WO 94/26273, WO/15132, EP 0 350 287, EP 93917054.4, and WO 91/19721.

Additional nonlimiting examples of derivatives of triciribine or related compounds are those that contain substituents as described in the following publications. These derivatized triciribine or related compounds can be used for the indications described in the text or otherwise as antiviral agents, including as anti-HIV or anti-HBV agents. Ho D. H. W., Cancer Res., 1973 33: p. 2816-2820; Holy A. in *Advances in Antiviral Drug Design*, Vol. I, De Clercq (ed.), JAI Press, pp. 179-231; Hong C. I. et al. Biochem Biophys Rs Commun, 1979. 88: p. 1223-1229; Hong C. I. et al., J Med Chem, 1980. 28: p. 171-177; Hostetler K. Y. et al., J Biol Chem, 1990. 266: p. 11714-11717; Hostetler K. Y. et al, Antiviral Res, 1994. 24: p. 59-67; Hostetler K. Y. et al, Antimicrobial Agents Chemother, 1994. 38: p. 2792-2797; Hunston R. N. et al, J Med Chem, 1984. 27: p. 440-444; Ji Y. H. et al, J Med Chem, 1990. 33: p. 2264-2270; Jones A. S. et al., J Chem Soc Perkin Trans, 1984. I: p. 1471-1474; Juodka B. A. and Smart J., Coll Czech Chem Comm, 1974. 39: p. 363-968; Kataoka S. et al, Nucleic Acids Res Sym Ser, 1989. 21: p. 1-2; Kataoka S. et al, Heterocycles, 1991. 32: p. 1351-1356; Kinchington D. et al, Antiviral Chem Chemother, 1992. 3: p. 107-112; Kodama K. et al., Jpn J Cancer Res, 1989. 80: p. 679-685; Korty M. and Engels J., Naunyn-Schmiedeberg's Arch Pharmacol, 1979. 10: p. 103-111; Kumar A. et al., J Med Chem, 1990. 33: p. 2368-2375; LeBec C. and Huynh-dinh T., Tetrahedron Lett, 1991. 32: p. 6553-6556; Lichtenstein J. et al., J Biol Chem, 1960. 235: p. 457-465; Lucthy J. et al., Mitt Geg Lebensmittelunters Hyg, 1981. 72: p. 131-133 (Chem. Abstr. 95, 127093); McGuigan C. et al., Nucleic Acids Res, 1989. 17: p. 6065-6075; McGuigan C. et al., Antiviral Chem Chemother, 1990. 1: p. 107-113; McGuigan C. et al, Antiviral Chem Chemother, 1990. 1: p. 355-360; McGuigan C. et al., Antiviral Chem Chemother, 1990. 1: p. 25-33; McGuigan C. et al., Antiviral Res, 1991. 15: p. 255-263; McGuigan C. et al., Antiviral Res, 1992. 17: p. 311-321; McGuigan C. et al., Antiviral Chem Chemother, 1993. 4: p. 97-101; McGuigan C. et al., J Med Chem, 1993. 36: p. 1048-1052.

Alkyl hydrogen phophonate derivatives of the anti-HIV agent AZT may be less toxic than the parent nucleoside analogue. Antiviral Chem Chemother. 5: 271-277; Meyer R. B. et al., Tetrahedron Lett, 1973. 269-272; Nagyvary J. et al., Biochem Biophys Res Commun, 1973. 55: p. 1072-1077; Namane A. et al., J Med Chem, 1992. 35: p. 3939-3044; Nargeot J. et al., Natl. Acad. Sci. U.S.A., 1983. 80: p. 2395-2399; Nelson K. A. et al., J Am Chem Soc, 1987. 109: p. 4058-4064; Nerbonne J. M. et al., Nature, 1984. 301: p. 74-76; Neumann J. M. et al., J Am Chem Soc, 1 1989. 111: p. 4270-4277; Ohno R. et al., Oncology, 1991. 48: p. 451-455. Palomino E. et al., J Med Chem, 1989. 32: p. 622-625; Perkins R. M. et al., Antiviral Res, 1993. 20(Suppl. I): p. 84; Piantadosi C. et al., J Med Chem, 1991. 34: 1408-1414; Pompon A. et al., Antiviral Chem Chemother, 1994. 5: p. 91-98; Postemark T., Anu Rev Pharmacol, 1974. 14: p. 23-33; Prisbe E. J. et al., J Med Chem, 1986. 29: p. 671-675; Pucch F. et al., Antiviral Res, 1993. 22: p. 155-174; Pugaeva V. P. et al., Gig Trf Prof Zabol, 1969. 13: p. 47-48 (Chem. Abstr. 72, 212); Robins R. K., Pharm Res, 1984. 11-18; Rosowsky A. et al., J Med Chem, 1982. 25: p. 171-178; Ross W., Biochem Pharm, 1961. 8: p. 235-240; Ryu E. K. et al., J Med Chem, 1982. 25: p. 1322-1329; Saffhill R. and Hume W. J., Chem Biol Interact, 1986. 57: p. 347-355; Saneyoshi M. et al., Chem Pharm Bull, 1980. 28: p. 2915-2923; Sastry J. K. et al., Mol Pharmacol, 1992. 41: p. 441-445; Shaw J. P. et al., 9th Annual AAPS Meeting, 1994. San Diego, Calif. (Abstract). Shuto S. et al., Tetrahedron Lett, 1987. 28: p. 199-202; Shuto S. et al., Chem Pharm Bull, 1988. 36: p. 209-217. One preferred phosphate prodrug group is the S-acyl-2-thioethyl group, also referred to as "SATE."

Additional examples of prodrugs that can be used are those described in the following patents and patent applications: U.S. Pat. Nos. 5,614,548, 5,512,671, 5,770,584, 5,962,437, 5,223,263, 5,817,638, 6,252,060, 6,448,392, 5,411,947, 5,744,592, 5,484,809, 5,827,831, 5,696,277, 6,022,029, 5,780,617, 5,194,654, 5,463,092, 5,744,461, 4,444,766, 4,562,179, 4,599,205, 4,493,832, 4,221,732, 5,116,992, 6,429,227, 5,149,794, 5,703,063, 5,888,990, 4,810,697, 5,512,671, 6,030,960, 2004/0259845, U.S. Pat. No. 6,670,341, 2004/0161398, 2002/082242, U.S. Pat. No. 5,512,671, 2002/0082242, and or PCT Publication Nos WO 90/11079, WO 96/39197, and/or WO 93/08807.

5.4. In Vivo Efficacy/Dosing Regimens

In another aspect of the present invention, dosing regimens are provided that limit the toxic side effects of TCN and related compounds. In one embodiment, such dosing regimens minimize the following toxic side effects, including, but not limited to, hepatoxicity, thrombocytopenia, hyperglycemia, vomiting, hypocalcemia, anemia, hypoalbunemia, myelo suppression, hypertriglyceridemia, hyperamylasemia, diarrhea, stomachitis and/or fever.

In another embodiment, the administration of TCN, TCN-P or related compounds and an erlotinib-like compound, for example, gefitinib, erlotinib or a salt thereof, provides at least a partial or complete response in vivo in at least 15-20% of the subjects. In particular embodiments, a partial reponse can be at least 15, 20, 25, 30, 35, 40, 50, 55, 60, 65, 70, 75, 80 or 85% regression of the tumor. In other embodiments, this response can be evident in at least 15, 15, 20, 25, 30, 35, 40, 50, 55, 60, 65, 70, 75, 80, 85 or 90% of the subjects treated with the therapy. In further embodiments, such response rates can be obtained by any therapeutic regimen disclosed herein.

In other embodiments, methods are provided to treat a subject that has been diagnosed with cancer by administering to the subject an effective amount of TCN, TCN-P or a related compound and an erlotinib-like compound, for example, gefitinib, erlotinib or a salt thereof, according to a dosing schedule that includes administering the triciribine compound and/an erlotinib-like compound, for example, gefitinib, erlotinib or a salt thereof, one time per week for three weeks followed by a one week period wherein the drug is not administered (i.e., via a 28 day cycle). In other embodiments, such 28 day cycles can be repeated at least 2, 3, 4, or 5 times or until regression of the tumor is evident.

In further embodiments, a 42 day cycle is provided in which the compounds disclosed herein can be administered once a week for four weeks followed by a two week period in which the triciribine compound and/or an erlotinib-like compound, for example, gefitinib, erlotinib or a salt thereof, is not administered. In other embodiments, such 42 day cycles can be repeated at least 2, 3, 4, or 5 times or until regression of the tumor is evident. In a particular embodiment, less than 12, less than 11 or less than 10 mg/m$^2$ of TCN, TCN-P or a related compound can be administered according to a 42 day cycle. In other particular embodiments, 2, 3, 4, 5, 6, 7, 8, 9, 10 or 15 mg/m$^2$ of TCN, TCN-P or a related compound can be administered according to a 42 day cycle. In another particular embodiment, about 1 to about 50 mg of an erlotinib-like compound, for example, gefitinib, erlotinib or a salt thereof is administered. In a particular embodiment, 1, 5, 10, 15, 20, 25, 30, 35, or 40 mg of an erlotinib-like compound, for example, gefitinib, erlotinib or a salt thereof, can be administered according to a 42 day cycle.

In another embodiment, methods are provided to treat cancer in a subject by administering to the subject a dosing regimen of 10 mg/m$^2$ or less of TCN, TCN-P or a related compound and less than about 30 mg of an erlotinib-like compound, for example, gefitinib, erlotinib or a salt thereof, one time per week. In particular embodiments, 0.5, 1, 1.5, 2, 2.5, 3, 3.5, 4, 4.5, 5, 5.5, 6, 6.5, 7, 7.5, 8, 8.5, 9, 9.5 or 10 mg/m$^2$ of TCN, TCN-P or a related compound as dislosed herein can be administered one time per week In another particular embodiment, 1, 5, 10, 15, 20, 25, 30, 35, or 40 mg of an erlotinib-like compound, for example, gefitinib, erlotinib or a salt thereof, can be administered one time per week.

In embodiments of the present invention, the compounds disclosed herein can be administered simultaneously as a single bolus dose over a short period of time, for example, about 5, 10, 15, 20, 30 or 60 minutes. In further embodiments, dosing schedules are provided in which the compounds are administered simultaneously via continuous infusion for at least 24, 48, 72, 96, or 120 hours. In certain embodiments, the administration of the triciribine compound and/or an erlotinib-like compound, for example, gefitinib, erlotinib or a salt thereof, via continuous or bolus injections can be repeated at a certain frequency at least: once a week, once every two weeks, once every three weeks, once a month, once every five weeks, once every six weeks, once every eight weeks, once every ten weeks and/or once every twelve weeks. The type and frequency of administrations can be combined in any manner disclosed herein to create a dosing cycle. The triciribine compound and/or an erlotinib-like compound, for example, gefitinib, erlotinib or a salt thereof, can be repeatedly administered via a certain dosing cycles, for example as a bolus injection once every two weeks for three months. The dosing cycles can be administered for at least: one, two three, four five, six, seven, eight, nine, ten, eleven, twelve, eighteen or twenty four months. Alternatively, at least 2, 3, 4, 5, 6, 7, 8, 9, 10, 11, 12, 15 or 20 dosing cycles can be administered to a patient. The triciribine compound and/or an erlotinib-like compound, for example, gefitinib, erlotinib or a salt thereof, can be administered according to any combination disclosed herein, for example, the triciribine compound and/or an erlotinib-like compound, for example, gefitinib, erlotinib or a salt thereof, can be administered once a week every three weeks for 3 cycles.

In further embodiments, the compounds can be administered separately at least once a day for at least 2, 3, 4, 5, 6, 7, 8, 9 or 10 days. Such administration can be followed by corresponding periods in which the triciribine compound and/or an erlotinib-like compound, for example, gefitinib, erlotinib or a salt thereof, are not administered The TCN, TCN-P and related compounds and an erlotinib-like compound, for example, gefitinib, erlotinib or a salt thereof, as disclosed herein can be administered to patients in an amount that is effective in causing tumor regression. The administration of TCN, TCN-P or related compounds and an erlotinib-like compound, for example, gefitinib, erlotinib or a salt thereof can provide at least a partial, such as at least 15, 20 or 30%, or complete response in vivo in at least 15-20% of the subjects. In certain embodiments, at least 2, 5, 10, 15, 20, 30 or 50 mg/m$^2$ of a triciribine compound disclosed herein can be administered to a subject. In certain embodiments, at least about 0.5, 1, 1.5, 2, 2.5, 3, 3.5, 4, 4.5, 5, 5.5, 6, 6.5, 7, 7.5, 8, 8.5, 9, 9.5, 10, 12, 15, 17, 20, 25, 30, 35, 40, 45, 50, 55, 60, 65, 70, 75, 80, 85, 90, 95, 100, 150, 165, 175, 200, 250, 300, or 350 mg/m$^2$ of TCN, TCN-P or a related compound disclosed herein can be administered to a subject. In certain embodiments, 1, 5, 10, 15, 20, 25, 30, 35, or 40 mg of an erlotinib-like compound, for example, gefitinib, erlotinib or a salt thereof, can be administered to a subject.

The administration of the compound can be conducted according to any of therapeutic regimens disclosed herein. In particular embodiments, the dosing regimen includes administering less than about 20 mg/m$^2$ of TCN and related compounds and less than about 30 mg of an erlotinib-like compound, for example, gefitinib, erlotinib or a salt thereof, either concurrently, sequentially, or conducted over a period of time. In one embodiment, less than 20 mg/m$^2$ of TCN or related compounds can be administered once a week concurrently with less than about 30 mg of an erlotinib-like compound, for example, gefitinib, erlotinib or a salt thereof. In another embodiment, less than 20 mg/m$^2$ of TCN or related compounds can be administered once a week and less than about 30 mg of an erlotinib-like compound, for example, gefitinib, erlotinib or a salt thereof can be administered the following week.

In further embodiments, 2 mg/m$^2$, 5 mg/m$^2$, 10 mg/m$^2$, and/or 15 mg/m$^2$ of TCN or a related compound and less than about 300, 250, 200, 150, or 100 mg an erlotinib-like compound, for example, gefitinib, erlotinib or a salt thereof can be administered to a subject. In another embodiment, less than 10 mg/m$^2$ of a triciribine compound and less than about 300 mg of an erlotinib-like compound, for example, gefitinib, erlotinib or a salt thereof can be administered to a subject via continuous infusion for at least five days. The present invention provides for any combination of dosing type, frequency, number of cycles and dosage amount disclosed herein.

5.5. Screening of Patient Populations

In another aspect of the present invention, methods are provided to identify cancers or tumors that are susceptible to the toxic effects of triciribine (TCN) and related compounds. In one embodiment, methods are provided to treat a cancer or tumor in a mammal by (i) obtaining a biological sample from the tumor; (ii) determining whether the cancer or tumor overexpresses Akt kinase or hyperactivated and phosphorylated Akt kinase, and (iii) treating the cancer or tumor with triciribine or a related compound as described herein. In one embodiment, the biological sample can be a biopsy. In other embodiments, the biological sample can be fluid, cells and/or aspirates obtained from the tumor or cancer.

The biological sample can be obtained according to any technique known to one skilled in the art. In one embodiment, a biopsy can be conducted to obtain the biological sample. A biopsy is a procedure performed to remove tissue or cells from the body for examination. Some biopsies can be performed in a physician's office, while others need to be done in a hospital setting. In addition, some biopsies require use of an anesthetic to numb the area, while others do not require any sedation. In certain embodiments, an endoscopic biopsy can be performed. This type of biopsy is performed through a fiberoptic endoscope (a long, thin tube that has a close-focusing telescope on the end for viewing) through a natural body orifice (i.e., rectum) or a small incision (i.e., arthroscopy). The endoscope is used to view the organ in question for abnormal or suspicious areas, in order to obtain a small amount of tissue for study. Endoscopic procedures are named for the organ or body area to be visualized and/or treated. The physician can insert the endoscope into the gastrointestinal tract (alimentary tract endoscopy), bladder (cystoscopy), abdominal cavity (laparoscopy), joint cavity (arthroscopy), mid-portion of the chest (mediastinoscopy), or trachea and bronchial system (laryngoscopy and bronchoscopy).

In another embodiment, a bone marrow biopsy can be performed. This type of biopsy can be performed either from the sternum (breastbone) or the iliac crest hipbone (the bone area on either side of the pelvis on the lower back area). The skin is cleansed and a local anesthetic is given to numb the area. A long, rigid needle is inserted into the marrow, and cells are aspirated for study; this step is occasionally uncomfortable. A core biopsy (removing a small bone 'chip' from the marrow) may follow the aspiration.

In a further embodiment, an excisional or incisional biopsy can be performed on the mammal. This type of biopsy is often used when a wider or deeper portion of the skin is needed. Using a scalpel (surgical knife), a full thickness of skin is removed for further examination, and the wound is sutured (sewed shut with surgical thread). When the entire tumor is removed, it is referred to as an excisional biopsy technique. If only a portion of the tumor is removed, it is referred to as an incisional biopsy technique. Excisional biopsy is often the method usually preferred, for example, when melanoma (a type of skin cancer) is suspected.

In still further embodiments, a fine needle aspiration (FNA) biopsy can be used. This type of biopsy involves using a thin needle to remove very small pieces from a tumor. Local anesthetic is sometimes used to numb the area, but the test rarely causes much discomfort and leaves no scar. FNA is not, for example, used for diagnosis of a suspicious mole, but may be used, for example, to biopsy large lymph nodes near a melanoma to see if the melanoma has metastasized (spread). A computed tomography scan (CT or CAT scan) can be used to guide a needle into a tumor in an internal organ such as the lung or liver.

In other embodiments, punch shave and/or skin biopsies can be conducted. Punch biopsies involve taking a deeper sample of skin with a biopsy instrument that removes a short cylinder, or "apple core," of tissue. After a local anesthetic is administered, the instrument is rotated on the surface of the skin until it cuts through all the layers, including the dermis, epidermis, and the most superficial parts of the subcutis (fat). A shave biopsy involves removing the top layers of skin by shaving it off. Shave biopsies are also performed with a local anesthetic. Skin biopsies involve removing a sample of skin for examination under the microscope to determine if, for example, melanoma is present. The biopsy is performed under local anesthesia.

In particular embodiment, methods are provided to determine whether the tumor overexpresses an Akt kinase. Akt kinase overexpression can refer to the phosphorylation state of the kinase. Hyperphosphorylation of Akt can be detected according to the methods described herein. In one embodiment, a tumor biopsy can be compared to a control tissue. The control tissue can be a normal tissue from the mammal in which the biopsy was obtained or a normal tissue from a healthy mammal. Akt kinase overexpression or hyperphosphorylation can be determined if the tumor biopsy contains greater amounts of Akt kinase and/or Akt kinase phosphorylation than the control tissue, such as, for example, at least approximately 1.5, 2, 2.25, 2.5, 2.75, 3, 3.25, 3.5, 3.75, 4, 4.25, 4.5, 4.75, 5, 5.5, 6, 7, 8, 9, or 10-fold greater amounts of Akt kinase than contained in the control tissue.

In one embodiment, the present invention provides a method to detect aberrant Akt kinase expression in a subject or in a biological sample from the subject by contacting cells, cell extracts, serum or other sample from the subjects or said biological sample with an immunointeractive molecule specific for an Akt kinase or antigenic portion thereof and screening for the level of immunointeractive molecule-Akt kinase complex formation, wherein an elevated presence of the complex relative to a normal cell is indicative of an aberrant cell that expresses or overexpresses Akt. In one example, cells or cell extracts can be screened immunologically for the presence of elevated levels of Akt kinase.

In an alternative embodiment, the aberrant expression of Akt in a cell is detected at the genetic level by screening for the level of expression of a gene encoding an Akt kinase wherein an elevated level of a transcriptional expression product (i.e., mRNA) compared to a normal cell is indicative of an aberrant cell. In certain embodiments, real-time PCR as well as other PCR procedures can be used to determine transcriptional activity. In one embodiment, mRNA can be obtained from cells of a subject or from a biological sample from a subject and cDNA optionally generated. The mRNA or cDNA can then be contacted with a genetic probe capable of hybridizing to and/or amplifying all or part of a nucleotide sequence encoding Akt kinase or its complementary nucleotide sequence and then the level of the mRNA or cDNA can be detected wherein the presence of elevated levels of the mRNA or cDNA compared to normal controls can be assessed.

Yet another embodiment of the present invention contemplates the use of an antibody, monoclonal or polyclonal, to Akt kinase in a quantitative or semi-quantitative diagnostic kit to determine relative levels of Akt kinase in suspected cancer cells from a patient, which can include all the reagents necessary to perform the assay. In one embodiment, a kit utilizing reagents and materials necessary to perform an ELISA assay is provided. Reagents can include, for example, washing buffer, antibody dilution buffer, blocking buffer, cell staining solution, developing solution, stop solution, anti-phospho-protein specific antibodies, anti-Pan protein specific antibodies, secondary antibodies, and distilled water. The kit can also include instructions for use and can optionally be automated or semi-automated or in a form which is compatible with automated machine or software. In one embodiment, a phosphor-ser-473 Akt antibody that detects the activated form of AKT (Akt phosphorylated at serine 474) can be utilized as the antibody in a diagnostic kit. See, for example, Yuan et al., Oncogene, 2000. 19: p. 2324-2330.

5.6. Akt Kinases

Akt, also named $PKB^3$, represents a subfamily of the serine/threonine kinase. Three members, AKT1, AKT2, and AKT3, have been identified in this subfamily. Akt is activated by extracellular stimuli in a PI3K-dependent manner (Datta S. R. et al., Genes Dev, 1999. 13: p. 2905-2927). Full activation of Akt requires phosphorylation of $Thr^{308}$ in the activation loop and $Ser^{473}$ in the C-terminal activation domain. Akt is negatively regulated by PTEN tumor suppressor. Mutations in PTEN have been identified in various tumors, which lead to activation of Akt pathway (Datta S. R. et al., Genes Dev, 1999. 13: p. 2905-2927). In addition, amplification, overexpression and/or activation of Akt have been detected in a number of human malignancies (*Datta* S. R. et al., Genes Dev, 1999. 13: p. 2905-2927); Cheng J. Q. and Nicosia S. V., in *Encyclopedic Reference of Cancer*, 2001, Schwab D. (ed.) Springer, Berlin Heidelberg and New York: pp 35-7). Ectopic expression of Akt, especially constitutively active Akt, induces cell survival and malignant transformation whereas inhibition of Akt activity stimulates apoptosis in a range of mammalian cells (Datta S. R. et al., Genes Dev, 1999. 13: p. 2905-2927); Cheng J. Q. and Nicosia S. V, in *Encyclopedic Reference of Cancer,* 2001, Schwab D. (ed.) Springer, Berlin Heidelberg and New York: pp 35-7; Sun M. et al., Am J Path, 2001. 159: p. 431-437; Cheng J. Q. et al., Oncogene, 1997. 14: p. 2793-2801). Further, activation of Akt has been shown to associate with tumor invasiveness and chemoresistance (West K. A. et al., Drug Resist Updat, 2002. 5: p. 234-248).

Activation of the Akt pathway plays a pivotal role in malignant transformation and chemoresistance by inducing cell survival, growth, migration, and angiogenesis. The present invention provides methods to determine levels of Akt kinase overexpression and/or hyperactivated and phosphorylated Akt kinase.

The Akt kinase can be any known Akt family kinase, or kinase related thereto, including, but not limited to Akt 1, Akt 2, Akt 3. The mRNA and amino acid sequences of human Akt1, Akt2, and Akt 3 are illustrated in FIGS. 6*a-c*, 7*a-d*, and 8*a-c*, respectively.

5.7. Diagnostic Assays

Immunological Assays

In one embodiment, a method is provided for detecting the aberrant expression of an Akt kinase in a cell in a mammal or in a biological sample from the mammal, by contacting cells, cell extracts or serum or other sample from the mammal or biological sample with an immunointeractive molecule specific for an Akt kinase or antigenic portion thereof and screening for the level of immunointeractive molecule-Akt kinase complex formations and determining whether an elevated presence of the complex relative to a normal cell is present.

The immunointeractive molecule can be a molecule having specificity and binding affinity for an Akt kinase or its antigenic parts or its homologs or derivatives thereof. In one embodiment, the immunointeractive molecule can be an immunglobulin molecule. In other embodiments, the immunointeractive molecules can be an antibody fragments, single chain antibodies, and/or deimmunized molecules including humanized antibodies and T-cell associated antigen-binding molecules (TABMs). In one particular embodiment, the antibody can be a monoclonal antibody. In another particular embodiment, the antibody can be a polyclonal antibody. The immunointeractive molecule can exhibit specificity for an Akt kinase or more particularly an antigenic determinant or epitope on an Akt kinase. An antigenic determinant or epitope on an Akt kinase includes that part of the molecule to which an immune response is directed. The antigenic determinant or epitope can be a B-cell epitope or where appropriate a T-cell epitope. In one embodiment, the antibody is a phosphor-ser 473 Akt antibody.

One embodiment of the present invention provides a method for diagnosing the presence of cancer or cancer-like growth in a mammal, in which aberrant Akt activity is present, by contacting cells or cell extracts from the mammal or a biological sample from the subject with an Akt kinase-binding effective amount of an antibody having specificity for the Akt kinase or an antigenic determinant or epitope thereon and then quantitatively or qualitatively determining the level of an Akt kinase-antibody complex wherein the presence of elevated levels of said complex compared to a normal cell is determined.

Antibodies can be prepared by any of a number of means known to one skilled in the art. For example, for the detection of human Akt kinase, antibodies can be generally but not necessarily derived from non-human animals such as primates, livestock animals (e.g. sheep, cows, pigs, goats, horses), laboratory test animals (e.g. mice, rats, guinea pigs, rabbits) and/or companion animals (e.g. dogs, cats). Antibodies may also be recombinantly produced in prokaryotic or eukaryotic host cells. Generally, antibody based assays can be conducted in vitro on cell or tissue biopsies. However, if an antibody is suitably deimmunized or, in the case of human use, humanized, then the antibody can be labeled with, for example, a nuclear tag, administered to a patient and the site of nuclear label accumulation determined by radiological techniques. The Akt kinase antibody can be a cancer targeting agent. Accordingly, another embodiment of the present invention provides deimmunized forms of the antibodies for use in cancer imaging in human and non-human patients.

In general, for the generation of antibodies to an Akt kinase, the enzyme is required to be extracted from a biological sample whether this be from animal including human tissue or from cell culture if produced by recombinant means. The Akt kinase can be separated from the biological sample by any suitable means. For example, the separation may take advantage of any one or more of the Akt kinase's surface charge properties, size, density, biological activity and its affinity for another entity (e.g. another protein or chemical compound to which it binds or otherwise associates). Thus, for example, separation of the Akt kinase from the biological fluid can be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead (trademark) separation, immunochromatography, immuno-precipitation). The separation of Akt kinase from the biological fluid can preserve conformational epitopes present on the kinase and, thus, suitably avoids techniques that cause denaturation of the enzyme. In a further embodiment, the kinase can be separated from the biological fluid using any one or more of affinity separation, gel filtration and/or ultra-filtration.

Immunization and subsequent production of monoclonal antibodies can be carried out using standard protocols known in the art, such as, for example, described by Kohler and Milstein (Kohler and Milstein, Nature, 1975. 256: p. 495-499; Kohler and Milstein, Eur J Immunol, 1976. 6(7): p. 511-519; Coligan et al., (Current Protocols in Immunology, 1991-1997, John Wiley & Sons, Inc.) or Toyama et al. (Monoclonal Antibody, Experiment Manual, 1987, Kodansha Scientific). Essentially, an animal is immunized with an Akt kinase-containing biological fluid or fraction thereof or a recombinant form of Akt kinase by standard methods to produce antibody-producing cells, particularly antibody-producing somatic cells (e.g. B lymphocytes). These cells can then be removed from the immunized animal for immortalization. In certain embodiment, a fragment of an Akt kinase can be used to the generate antibodies. The fragment can be associated with a carrier. The carrier can be any substance of typically high molecular weight to which a non- or poorly immunogenic substance (e.g. a hapten) is naturally or artificially linked to enhance its immunogenicity.

Immortalization of antibody-producing cells can be carried out using methods which are well-known in the art. For example, the immortalization may be achieved by the transformation method using Epstein-Barr virus (EBV) (Kozbor et al., Methods in Enzymology, 1986. 121: p. 140). In another embodiment, antibody-producing cells are immortalized using the cell fusion method (described in Coligan et al., 1991-1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In a particular embodiment, mice spleen cells can be used. In other embodiments, rat, rabbit, sheep or goat cells can also be used. Specialized myeloma cell lines have been developed from lymphocytic tumours for use in hybridoma-producing fusion procedures (Kohler and Milstein, 1976, supra; Shulman et al., Nature, 1978. 276: p. 269-270; Volk et al., J Virol, 1982. 42(1): p. 220-227). Many myeloma cell lines can also be used for the production of fused cell hybrids, including, e.g. P3.times.63-Ag8, P3.times.63-AG8.653, P3/NS1-Ag4-1 (NS-1), Sp2/0-Ag14 and S194/5.XXO.Bu.1. The P3.times.63-Ag8 and NS-1 cell lines have been described by Kohler and Milstein (1976, supra). Shulman et al. (1978, supra) developed the Sp2/0-Ag14 myeloma line. The 5194/5.XXO.Bu.1 line was reported by Trowbridge (J Exp Med, 1978. 148(1): p. 313-323). Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler and Milstein, 1975, supra; Kohler and Milstein, 1976, supra; Gefter et al., Somatic Cell Genet, 1977. 3: p. 231-236; Volk et al., 1982, supra). The fusion-promoting agents used by those investigators were Sendai virus and polyethylene glycol (PEG). In certain embodiments, means to select the fused cell hybrids from the remaining unfused cells, particularly the unfused myeloma cells, are provided. Generally, the selection of fused cell hybrids can be accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. (Monoclonal Antibodies and Hybridomas: A New Dimension in Biological Analyses, 1980, Plenum Press, New York, p. 376-384) and by FACS analysis (O'Reilly et al., Biotechniques, 1998 25: p. 824-830).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines can then be tested for their specificity to detect the Akt kinase of interest by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target LIM kinase but which does not recognize non-target epitopes are identified and then directly cultured in vitro or injected into a histocompatible animal to form tumours and to produce, collect and purify the required antibodies.

The present invention provides, therefore, a method of detecting in a sample an Akt kinase or fragment, variant or derivative thereof comprising contacting the sample with an antibody or fragment or derivative thereof and detecting the level of a complex containing the antibody and Akt kinase or fragment, variant or derivative thereof compared to normal controls wherein elevated levels of Akt kinase is determined. Any suitable technique for determining formation of the complex may be used. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) immunochromatographic techniques (ICTs), and Western blotting which are well known to those of skill in the art. Immunoassays can also include competitive assays. The present invention encompasses qualitative and quantitative immunoassays.

Suitable immunoassay techniques are described, for example, in U.S. Pat. Nos. 4,016,043; 4,424,279; and 4,018,653. These include both single-site and two-site assays of the non-competitive types, as well as the traditional competitive binding assays. These assays also include direct binding of a labeled antigen-binding molecule to a target antigen.

The invention further provides methods for quantifying Akt protein expression and activation levels in cells or tissue samples obtained from an animal, such as a human cancer patient or an individual suspected of having cancer. In one embodiment, the invention provides methods for quantifying Akt protein expression or activation levels using an imaging system quantitatively. The imaging system can be used to receive, enhance, and process images of cells or tissue samples, that have been stained with AKT protein-specific stains, in order to determine the amount or activation level of AKT protein expressed in the cells or tissue samples from such an animal. In embodiments of the methods of the invention, a calibration curve of AKT1 and AKT2 protein expression can be generated for at least two cell lines expressing differing amounts of AKT protein. The calibration curve can then used to quantitatively determine the amount of AKT protein that is expressed in a cell or tissue sample. Analogous calibration curves can be made for activated AKT proteins using reagents specific for the activation features. It can also be used to determine changes in amounts and activation state of AKT before and after clinical cancer treatment.

In one particular embodiment of the methods of the invention, AKT protein expression in a cell or tissue sample can be quantified using an enzyme-linked immunoabsorbent assay (ELISA) to determine the amount of AKT protein in a sample. Such methods are described, for example, in U.S. Patent Publication No. 2002/0015974.

In other embodiments enzyme immunoassays can be used to detect the Akt kinase. In such assays, an enzyme is conjugated to the second antibody, generally by means of glutaraldehyde or periodate. The substrates to be used with the specific enzymes are generally chosen for the production of, upon hydrolysis by the corresponding enzyme, a detectable colour change. It is also possible to employ fluorogenic substrates, which yield a fluorescent product rather than the chromogenic substrates. The enzyme-labeled antibody can be added to the first antibody-antigen complex, allowed to bind, and then the excess reagent washed away. A solution containing the appropriate substrate can then be added to the complex of antibody-antigen-antibody. The substrate can react with the enzyme linked to the second antibody, giving a qualitative visual signal, which may be further quantitated, usually spectrophotometrically, to give an indication of the amount of antigen which was present in the sample. Alternately, fluorescent compounds, such as fluorescein, rhodamine and the lanthanide, europium (EU), can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent-labeled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules can also be employed.

In a particular embodiment, antibodies to Akt kinase can also be used in ELISA-mediated detection of Akt kinase especially in serum or other circulatory fluid. This can be accomplished by immobilizing anti-Akt kinase antibodies to a solid support and contacting these with a biological extract such as serum, blood, lymph or other bodily fluid, cell extract or cell biopsy. Labeled anti-Akt kinase antibodies can then be used to detect immobilized Akt kinase. This assay can be varied in any number of ways and all variations are encompassed by the present invention and known to one skilled in the art. This approach can enable rapid detection and quantitation of Akt kinase levels using, for example, a serum-based assay.

In one embodiment, an Akt ELISA assay kit may be used in the present invention. For example, a Cellular Activation of Signaling ELISA kit for Akt S473 from SuperArray Bioscience can be utilized in the present invention. In one embodiment, the antibody can be an anti-pan antibody that recognizes Akt S473. ELISA assay kit containing an anti-Akt antibody and additional reagents, including, but not limited to, washing buffer, antibody dilution buffer, blocking buffer, cell staining solution, developing solution, stop solution, secondary antibodies, and distilled water.

Nucleotide Detection

In another embodiment, a method to detect Akt kinases is provided by detecting the level of expression in a cell of a polynucleotide encoding an Akt kinase. Expression of the polynucleotide can be determined using any suitable technique known to one skilled in the art. In one embodiment, a labeled polynucleotide encoding an Akt kinase can be utilized as a probe in a Northern blot of an RNA extract obtained from the cell. In other embodiments, a nucleic acid extract from an animal can be utilized in concert with oligonucleotide primers corresponding to sense and anti-sense sequences of a polynucleotide encoding the kinase, or flanking sequences thereof, in a nucleic acid amplification reaction such as RT PCR. A variety of automated solid-phase detection techniques are also available to one skilled in the art, for example, as described by Fodor et al. (Science, 1991. 251: p. 767-777) and Kazal et al. (Nature Medicine, 1996. 2: p. 753-759).

In other embodiments, methods are provided to detect Akt kinase encoding RNA transcripts. The RNA can be isolated from a cellular sample suspected of containing Akt kinase RNA, e.g. total RNA isolated from human cancer tissue. RNA can be isolated by methods known in the art, e.g. using TRIZOL reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs can then amplified with sequence-specific oligonucleotides in PCR reactions to yield an amplified product.

Polymerase chain reaction or "PCR" refers to a procedure or technique in which amounts of a preselected fragment of nucleic acid, RNA and/or DNA, are amplified as described, for example, in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al. (Quant Biol, 1987. 51: p. 263; Erlich, eds., PCR Technology, 1989, Stockton Press, NY). Thus, amplification of specific nucleic acid sequences by PCR relies upon oligonucleotides or "primers" having conserved nucleotide sequences wherein the conserved sequences are deduced from alignments of related gene or protein sequences, e.g. a sequence comparison of mammalian Akt kinase genes. For example, one primer is prepared which is predicted to anneal to the antisense strand and another primer prepared which is predicted to anneal to the sense strand of a cDNA molecule which encodes a Akt kinase. To detect the amplified product, the reaction mixture is typically subjected to agarose gel electrophoresis or other convenient separation technique and the relative presence of the Akt kinase specific amplified DNA detected. For example, Akt kinase amplified DNA may be detected using Southern hybridization with a specific oligonucleotide probe or comparing its electrophoretic mobility with DNA standards of known molecular weight. Isolation, purification and characterization of the amplified Akt kinase DNA can be accomplished by excising or eluting the fragment from the gel (for example, see references Lawn et al., Nucleic Acids Res, 1981. 2: p. 6103; Goeddel et al., Nucleic Acids Res, 1980. 8: p. 4057), cloning the amplified product into a cloning site of a suitable vector, such as the pCRII vector (Invitrogen), sequencing the cloned insert and comparing the DNA sequence to the known sequence of LIM kinase. The relative amounts of LIM kinase mRNA and cDNA can then be determined.

In one embodiment, real-time PCR can be used to determine transcriptional levels of Akt nucleotides. Determination of transcriptional activity also includes a measure of potential translational activity based on available mRNA transcripts. Real-time PCR as well as other PCR procedures use a number of chemistries for detection of PCR product including the binding of DNA binding fluorophores, the 5' endonuclease, adjacent liner and hairpin oligoprobes and the self-fluorescing amplicons. These chemistries and real-time PCR in general are discussed, for example, in Mackay et al., Nucleic Acids Res, 2002. 30(6): p. 1292-1305; Walker, J Biochem Mol Toxicology, 2001. 15(3): p. 121-127; Lewis et al., J Pathol, 2001. 195: p. 66-71.

In an alternate embodiment, the aberrant expression of Akt can be identified by contacting a nucleotide sequences isolated from a biological sample with an oligonucleotide probe having a sequence complementary to an Akt sequences selected from the nucleotide sequences of FIGS. 6a-c, 7a-d, or 8a-c, or fragment thereof, and then detecting the sequence by hybridizing the probe to the sequence, and comparing the results to a normal sample. The hybridization of the probe to the biological sample can be detected by labeling the probe using any detectable agent. The probe can be labeled for example, with a radioisotope, or with biotin, fluorescent dye, electron-dense reagent, enzyme, hapten or protein for which antibodies are available. The detectable label can be assayed by any desired means, including spectroscopic, photochemical, biochemical, immunochemical, radioisotopic, or chemical means. The probe can also be detected using techniques such as an oligomer restriction technique, a dot blot assay, a reverse dot blot assay, a line probe assay, and a 5' nuclease assay. Alternatively, the probe can be detected using any of the generally applicable DNA array technologies, including macroarray, microarray and DNA microchip technologies. The oligonucleotide probe typically includes approximately at least 14, 15, 16, 18, 20, 25 or 28 nucleotides that hybridize to the nucleotides selected from FIGS. 6a-c, 7a-d, and 8a-c, or a fragment thereof. It is generally not preferred to use a probe that is greater than approximately 25 or 28 nucleotides in length. The oligonucleotide probe is designed to identify an Akt nucleotide sequence.

Kinase Assays

The activity of the Akt kinases can be measured using any suitable kinase assay known in the art. For example, and not by way of limitation, the methods described in Hogg et al (Oncogene, 1994. 9: p. 98-96), Mills et al (J Biol Chem, 1992. 267: p. 16000-006) and Tomizawa et al. (FEBS Lett, 2001. 492: p. 221-7), Schmandt et al. (J Immunol, 1994. 152: p. 96-105) can be used. Further serine, threonine and tyrosine kinase assays are described in Ausubel et al. (Short Protocols in Molecular Biology, 1999, unit 17.6).

Akt kinase assays can generally use an Akt polypeptide, a labeled donor substrate, and a receptor substrate that is either specific or non-specific for Akt. In such assays Akt transfers a labeled moiety from the donor substrate to the receptor substrate, and kinase activity is measured by the amount of labeled moiety transferred from the donor substrate to the receptor substrate. Akt polypeptide can be produced using various expression systems, can be purified from cells, can be in the form of a cleaved or uncleaved recombinant fusion protein and/or can have non-Akt polypeptide sequences, for example a His tag or .beta.-galactosidase at its N- or C-terminus. Akt activity can be assayed in cancerous cells lines if the cancerous cell lines are used as a source of the Akt to be assayed. Suitable donor substrates for Akt assays include any molecule that is susceptible to dephosphorylation by Akt, such as, for example include .gamma.-labeled ATP and ATP analogs, wherein the label is $^{33}P$, $^{32}P$, $^{35}S$ or any other radioactive isotope or a suitable fluorescent marker. Suitable recipient substrates for Akt assays include any polypeptide or other molecule that is susceptible to phosphorylation by Akt. Recipient substrates can be derived from fragments of in vivo targets of Akt. Recipient substrates fragments can be 8 to 50 amino acids in length, usually 10 to 30 amino acids and particularly of about 10, 12, 15, 18, 20 and 25 amino acids in length. Further recipient substrates can be determined empirically using a set of different polypeptides or other molecules. Targets of Recipient substrates for TTK can be capable of being purified from other components of the reaction once the reaction has been performed. This purification is usually done through a molecular interaction, where the recipient substrates is biotinylated and purified through its interaction with streptavidin, or a specific antibody is available that can specifically recognize the recipient substrates. The reaction can be performed in a variety of conditions, such as on a solid support, in a gel, in solution or in living cells. The choice of detection methods depends on type of label used for the donor molecule and may include, for example, measurement of incorporated radiation or fluorescence by autoradiography, scintillation, scanning or fluorography.

6. Methods of Treatment

The compounds and pharmaceutical compositions provided herein can be used in the treatment of a condition including tumors, cancer, and other disorders associated with abnormal cell proliferation. In one embodiment, the compounds of the present invention can be used to treat a carcinoma, sarcoma, lymphoma, leukemia, and/or myeloma. In other embodiments of the present invention, the compounds disclosed herein can be used to treat solid tumors.

The compounds of the present invention can be used for the treatment of cancer, such as, but not limited to cancer of the following organs or tissues: breast, prostate, lung, bronchus, colon, urinary, bladder, non-Hodgkin lymphoma, melanoma, kidney, renal, pancreas, pharnx, thyroid, stomach, brain, multiple myeloma, esophagus, liver, intrahepatic bile duct, cervix, larynx, acute myeloid leukemia, chronic lymphatic leukemia, soft tissue, such as heart, Hodgkin lymphoma, testis, small intestine, chronic myeloid leukemia, acute lymphatic leukemia, anus, anal canal, anorectal, thyroid, vulva, gallbladder, pleura, eye, nose nasal cavity, middle ear, nasopharnx, ureter, peritoneum, omentum, mesentery, and gastrointestineal, high grade glioma, glioblastoma, colon, rectal, pancreatic, gastric cancers, hepatocellular carcinoma; head and neck cancers, carcinomas; renal cell carcinoma; adenocarcinoma; sarcomas; hemangioendothelioma; lymphomas; leukemias, mycosis fungoides. In additional embodiments, the compounds of the present invention can be used to treat skin diseases including, but not limited to, the malignant diseases angio sarcoma, hemangioendothelioma, basal cell carcinoma, squamous cell carcinoma, malignant melanoma and Kaposi's sarcoma, and the non-malignant diseases or conditions such as psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagious, seborrheic keratosis, and actinic keratosis.

Compositions including the compounds of the invention can be used to treat these cancers and other cancers at any stage from the discovery of the cancer to advanced stages. In addition, compositions including compounds of the invention can be used in the treatment of the primary cancer and metastases thereof.

In other embodiments of the invention, the compounds described herein can be used for the treatment of cancer, including, but not limited to the cancers listed in Table 2 below.

TABLE 2

| Types of Cancer | |
|---|---|
| Acute Lymphoblastic Leukemia, Adult | Hairy Cell Leukemia |
| | Head and Neck Cancer |
| Acute Lymphoblastic Leukemia, Childhood | Hepatocellular (Liver) Cancer, Adult (Primary) |
| Acute Myeloid Leukemia, Adult | Hepatocellular (Liver) Cancer, Childhood |
| Acute Myeloid Leukemia, Childhood | (Primary) |
| Adrenocortical Carcinoma | Hodgkin's Lymphoma, Adult |
| Adrenocortical Carcinoma, Childhood | Hodgkin's Lymphoma, Childhood |
| | Hodgkin's Lymphoma During Pregnancy |
| AIDS-Related Cancers | Hypopharyngeal Cancer |
| AIDS-Related Lymphoma | Hypothalamic and Visual Pathway Glioma, Childhood |
| Anal Cancer | |
| Astrocytoma, Childhood Cerebellar | Intraocular Melanoma |
| Astrocytoma, Childhood Cerebral | Islet Cell Carcinoma (Endocrine Pancreas) |
| Basal Cell Carcinoma | Kaposi's Sarcoma |

TABLE 2-continued

| Types of Cancer | |
|---|---|
| Bile Duct Cancer, Extrahepatic | Kidney (Renal Cell) Cancer |
| Bladder Cancer | Kidney Cancer, Childhood |
| Bladder Cancer, Childhood | Laryngeal Cancer |
| Bone Cancer, Osteosarcoma/Malignant Fibrous Histiocytoma | Laryngeal Cancer, Childhood |
| | Leukemia, Acute Lymphoblastic, Adult |
| | Leukemia, Acute Lymphoblastic, Childhood |
| Brain Stem Glioma, Childhood | |
| Brain Tumor, Adult | Leukemia, Acute Myeloid, Adult |
| Brain Tumor, Brain Stem Glioma, Childhood | Leukemia, Acute Myeloid, Childhood |
| | Leukemia, Chronic Lymphocytic |
| Brain Tumor, Cerebellar Astrocytoma, Childhood | Leukemia, Chronic Myelogenous |
| | Leukemia, B Cell |
| Brain Tumor, Cerebral Astrocytoma/Malignant Glioma, Childhood | Lip and Oral Cavity Cancer |
| | Liver Cancer, Adult (Primary) |
| | Liver Cancer, Childhood (Primary) |
| Brain Tumor, Ependymoma, Childhood | Lung Cancer, Non-Small Cell |
| | Lung Cancer, Small Cell |
| Brain Tumor, Medulloblastoma, Childhood | Lymphoma, AIDS-Related |
| | Lymphoma, Burkitt's |
| Brain Tumor, Supratentorial Primitive Neuroectodermal Tumors, Childhood | Lymphoma, Cutaneous T-Cell, see Mycosis Fungoides and Sézary Syndrome |
| | Lymphoma, Hodgkin's, Adult |
| Brain Tumor, Visual Pathway and Hypothalamic Glioma, Childhood | Lymphoma, Hodgkin's, Childhood |
| | Lymphoma, Hodgkin's During Pregnancy |
| Brain Tumor, Childhood | Lymphoma, Non-Hodgkin's, Adult |
| Breast Cancer | Lymphoma, Non-Hodgkin's, Childhood |
| Breast Cancer, Childhood | Lymphoma, Non-Hodgkin's During Pregnancy |
| Breast Cancer, Male | |
| Bronchial Adenomas/Carcinoids, Childhood | Lymphoma, Primary Central Nervous System |
| Burkitt's Lymphoma | Macroglobulinemia, Waldenström's |
| Carcinoid Tumor, Childhood | Malignant Fibrous Histiocytoma of Bone/Osteosarcoma |
| Carcinoid Tumor, Gastrointestinal | |
| Carcinoma of Unknown Primary | Medulloblastoma, Childhood |
| Central Nervous System Lymphoma, Primary | Melanoma |
| | Melanoma, Intraocular (Eye) |
| Cerebellar Astrocytoma, Childhood | Merkel Cell Carcinoma |
| Cerebral Astrocytoma/Malignant Glioma, Childhood | Mesothelioma, Adult Malignant |
| | Mesothelioma, Childhood |
| Cervical Cancer | Metastatic Squamous Neck Cancer with Occult Primary |
| Childhood Cancers | |
| Chronic Lymphocytic Leukemia | Multiple Endocrine Neoplasia Syndrome, Childhood |
| Chronic Myelogenous Leukemia | |
| Chronic Myeloproliferative Disorders | Multiple Myeloma/Plasma Cell Neoplasm |
| Colon Cancer | Mycosis Fungoides |
| Colorectal Cancer, Childhood | Myelodysplastic Syndromes |
| Cutaneous T-Cell Lymphoma, see Mycosis Fungoides and Sézary Syndrome | Myelodysplastic/Myeloproliferative Diseases |
| | Myelogenous Leukemia, Chronic |
| Endometrial Cancer | Myeloid Leukemia, Adult Acute |
| Ependymoma, Childhood | Myeloid Leukemia, Childhood Acute |
| Esophageal Cancer | Myeloma, Multiple |
| Esophageal Cancer, Childhood | Myeloproliferative Disorders, Chronic |
| Ewing's Family of Tumors | Nasal Cavity and Paranasal Sinus Cancer |
| Extracranial Germ Cell Tumor, Childhood | Nasopharyngeal Cancer |
| | Nasopharyngeal Cancer, Childhood |
| Extragonadal Germ Cell Tumor | Neuroblastoma |
| Extrahepatic Bile Duct Cancer | Non-Hodgkin's Lymphoma, Adult |
| Eye Cancer, Intraocular Melanoma | Non-Hodgkin's Lymphoma, Childhood |
| Eye Cancer, Retinoblastoma | Non-Hodgkin's Lymphoma During Pregnancy |
| Gallbladder Cancer | |
| Gastric (Stomach) Cancer | Non-Small Cell Lung Cancer |
| Gastric (Stomach) Cancer, Childhood | Oral Cancer, Childhood |
| Gastrointestinal Carcinoid Tumor | Oral Cavity Cancer, Lip and |
| Germ Cell Tumor, Extracranial, Childhood | Oropharyngeal Cancer |
| | Osteosarcoma/Malignant Fibrous Histiocytoma of Bone |
| Germ Cell Tumor, Extragonadal | |
| Germ Cell Tumor, Ovarian | Ovarian Cancer, Childhood |
| Gestational Trophoblastic Tumor | Ovarian Epithelial Cancer |
| Glioma, Adult | Ovarian Germ Cell Tumor |
| Glioma, Childhood Brain Stem | Ovarian Low Malignant Potential Tumor |
| Glioma, Childhood Cerebral Astrocytoma | Pancreatic Cancer |
| | Pancreatic Cancer, Childhood |
| Glioma, Childhood Visual Pathway and Hypothalamic | Pancreatic Cancer, Islet Cell |
| | Paranasal Sinus and Nasal Cavity Cancer |
| Skin Cancer (Melanoma) | Parathyroid Cancer |
| Skin Carcinoma, Merkel Cell | Penile Cancer |
| Small Cell Lung Cancer | Pheochromocytoma |

TABLE 2-continued

Types of Cancer

| | |
|---|---|
| Small Intestine Cancer | Pineoblastoma and Supratentorial Primitive |
| Soft Tissue Sarcoma, Adult | Neuroectodermal Tumors, Childhood |
| Soft Tissue Sarcoma, Childhood | Pituitary Tumor |
| Squamous Cell Carcinoma, see Skin Cancer (non-Melanoma) | Plasma Cell Neoplasm/Multiple Myeloma |
| | Pleuropulmonary Blastoma |
| Squamous Neck Cancer with Occult Primary, Metastatic | Pregnancy and Breast Cancer |
| | Pregnancy and Hodgkin's Lymphoma |
| Stomach (Gastric) Cancer | Pregnancy and Non-Hodgkin's Lymphoma |
| Stomach (Gastric) Cancer, Childhood | Primary Central Nervous System Lymphoma |
| Supratentorial Primitive Neuroectodermal Tumors, Childhood | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer Urethral Cancer Uterine Cancer, Endometrial | Skin Cancer, Childhood |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In further embodiments of the present invention, the compounds disclosed herein can be used in the treatment of angiogenesis-related diseases.

Antiangiogenic small molecules include thalidomide, which acts in part by inhibiting NFkB, 2-methoxyestradiol, which influences microtubule activation and hypoxia inducing factor (HIF1a) activation, cyclo-oxygenase 2 (COX2) inhibitors, and low doses of conventional chemotherapeutic agents, including cyclophosphamide, taxanes, and vinca alkaloids (vincristine, vinblastine) (D'Amato R. J. et al., Proc. Natl. Acad. Sci. U.S.A, 1994. 91: p. 3964-3968; D'Amato R. J. et al., Proc. Natl. Acad. Sci. U.S.A, 1994. 91: p. 4082-4085). In addition, certain tyrosine kinase inhibitors indirectly decrease angiogenesis by decreasing production of VEGF and other proangiogenic factors by tumor and stromal cells. These drugs include Herceptin, imatinib (Glivec), and Iressa (Bergers G. et al., J Clin Invest, 2003. 111: p. 1287-1295; Ciardiello F. et al., Clin Cancer Res, 2001. 7: p. 1459-1465; Plum S. M. et al., Clin Cancer Res, 2003. 9: p. 4619-4626).

Recently, angiogenesis inhibitors have moved from animal models to human patients. Angiogenesis inhibitors represent a promising treatment for a variety of cancers. Recently, Avastin a high affinity antibody against vascular endothelial growth factor (VEGF), has been shown to prolong life as a single agent in advanced renal cell carcinoma and prolong life in combination with chemotherapy in advanced colon cancer (Yang J. C. et al., New Eng J Med, 2003. 349: p. 427-434; Kabbinavar F. et al., J Clin Onc, 2003. 21: p. 60-65).

Angiogenesis-related diseases include, but are not limited to, inflammatory, autoimmune, and infectous diseases; angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; eczema; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. In addition, compositions of this invention can be used to treat diseases such as, but not limited to, intestinal adhesions, atherosclerosis, scleroderma, warts, and hypertrophic scars (i.e., keloids). Compositions of this invention can also be used in the treatment of diseases that have angiogenesis as a pathologic consequence such as cat scratch disease (*Rochele minalia quintosa*), ulcers (*Helobacter pylori*), tuberculosis, and leprosy.

6.1. Treatment of Drug Resistant Tumors or Cancers

The invention provides compounds that can be used to treat drug resistant cancer, including the embodiments of cancers and the triciribine compound and/or the an erlotinib-like compound, for example, gefitinib, erlotinib or a salt thereof.

Multidrug resistance (MDR) occurs in human cancers and can be a significant obstacle to the success of chemotherapy. Multidrug resistance is a phenomenon whereby tumor cells in vitro that have been exposed to one cytotoxic agent develop cross-resistance to a range of structurally and functionally unrelated compounds. In addition, MDR can occur intrinsically in some cancers without previous exposure to chemotherapy agents. Thus, in one embodiment, the present invention provides methods for the treatment of a patient with a drug resistant cancer, for example, multidrug resistant cancer, by administration of TCN, TCN-P or a related compound and an erlotinib-like compound, for example, gefitinib, erlotinib or a salt thereof. In certain embodiments, TCN, TCN-P and related compounds and an erlotinib-like compound, for example, gefitinib, erlotinib or a salt thereof can be used to treat cancers that are resistant to taxol alone, rapamycin, tamoxifen, cisplatin, and/or gefitinib (iressa).

In one embodiment, TCN, TCN-P or a related compound and an erlotinib-like compound, for example, gefitinib, erlotinib or a salt thereof can be used for the treatment of drug resistent cancers of the colon, bone, kidney, adrenal, pancreas, liver and/or any other cancer known in the art or described herein.

6.2. Combination Therapy

In one embodiment, the triciribine compounds and an erlotinib-like compound, for example, gefitinib, erlotinib or a salt thereof can be administered together with other cytotoxic agents. In another embodiment, the triciribine compounds and an erlotinib-like compound, for example, gefitinib, erlotinib or a salt thereof and compositions thereof, when used in the treatment of solid tumors, can be administered the use of radiation.

In another embodiment of the present invention, the triciribine compounds and an erlotinib-like compound, for example, gefitinib, erlotinib or a salt thereof and compositions disclosed herein can be combined with at least one additional chemotherapeutic agent. The additional agents can be administered in combination or alternation with the compounds disclosed herein. The drugs can form part of the same composition, or be provided as a separate composition for administration at the same time or a different time.

In one embodiment, the triciribine compounds and an erlotinib-like compound, for example, gefitinib, erlotinib or a salt thereof disclosed herein can be combined with anti-angiogenic agents to enhance their effectiveness, or combined with other antiangiogenic agents and administered together with other cytotoxic agents. In another embodiment, the triciribine compounds and an erlotinib-like compound, for example, gefitinib, erlotinib or a salt thereof and compositions, when used in the treatment of solid tumors, can be administered with the agents selected from, but not limited to IL-12, retinoids, interferons, angiostatin, endostatin, thalidomide, thrombospondin-1, thrombospondin-2, captopryl, anti-neoplastic agents such as alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and radiation. In further embodiments, the compounds and compositions disclosed herein can be administered in combination or alternation with, for example, drugs with antimitotic effects, such as those which target cytoskeletal elements, including podophylotoxins or vinca alkaloids (vincristine, vinblastine); antimetabolite drugs (such as 5-fluorouracil, cytarabine, gemcitabine, purine analogues such as pentostatin, methotrexate); alkylating agents or nitrogen mustards (such as nitrosoureas, cyclophosphamide or ifosphamide); drugs which target DNA such as the antracycline drugs adriamycin, doxorubicin, pharmorubicin or epirubicin; drugs which target topoisomerases such as etoposide; hormones and hormone agonists or antagonists such as estrogens, antiestrogens (tamoxifen and related compounds) and androgens, flutamide, leuprorelin, goserelin, cyprotrone or octreotide; drugs which target signal transduction in tumour cells including antibody derivatives such as herceptin; alkylating drugs such as platinum drugs (cis-platin, carbonplatin, oxaliplatin, paraplatin) or nitrosoureas; drugs potentially affecting metastasis of tumours such as matrix metalloproteinase inhibitors; gene therapy and antisense agents; antibody therapeutics; other bioactive compounds of marine origin, notably the didemnins such as aplidine; steroid analogues, in particular dexamethasone; anti-inflammatory drugs, including nonsteroidal agents (such as acetaminophen or ibuprofen) or steroids and their derivatives in particular dexamethasone; anti-emetic drugs, including 5HT-3 inhibitors (such as gramisetron or ondasetron), and steroids and their derivatives in particular dexamethasone. In still further embodiments, the compounds and compositions can be used in combination or alternation with the chemotherapeutic agents disclosed below in Table 3.

TABLE 3

| Chemotherapeutic Agents | |
|---|---|
| 13-cis-Retinoic Acid | Neosar |
| 2-Amino-6-Mercaptopurine | Neulasta |
|  | Neumega |
| 2-CdA | Neupogen |
| 2-Chlorodeoxyadenosine | Nilandron |
| 5-fluorouracil | Nilutamide |
| 5-FU | Nitrogen Mustard |
| 6-TG | Novaldex |
| 6-Thioguanine | Novantrone |
| 6-Mercaptopurine | Octreotide |
| 6-MP | Octreotide acetate |
| Accutane | Oncospar |
| Actinomycin-D | Oncovin |
| Adriamycin | Ontak |
| Adrucil | Onxal |
| Agrylin | Oprevelkin |
| Ala-Cort | Orapred |
| Aldesleukin | Orasone |
| Alemtuzumab | Oxaliplatin |
| Alitretinoin | Paclitaxel |
| Alkaban-AQ | Pamidronate |
| Alkeran | Panretin |
| All-transretinoic acid | Paraplatin |
| Alpha interferon | Pediapred |
| Altretamine | PEG Interferon |
| Amethopterin | Pegaspargase |
| Amifostine | Pegfilgrastim |
| Aminoglutethimide | PEG-INTRON |
| Anagrelide | PEG-L-asparaginase |
| Anandron | Phenylalanine Mustard |
| Anastrozole | Platinol |
| Arabinosylcytosine | Platinol-AQ |
| Ara-C | Prednisolone |
| Aranesp | Prednisone |
| Aredia | Prelone |
| Arimidex | Procarbazine |
| Aromasin | PROCRIT |
| Arsenic trioxide | Proleukin |
| Asparaginase | Prolifeprospan 20 with Carmustine implant |
| ATRA | Purinethol |
| Avastin | Raloxifene |
| BCG | Rheumatrex |

TABLE 3-continued

Chemotherapeutic Agents

| | |
|---|---|
| BCNU | Rituxan |
| Bevacizumab | Rituximab |
| Bexarotene | Roveron-A (interferon alfa-2a) |
| Bicalutamide | Rubex |
| BiCNU | Rubidomycin hydrochloride |
| Blenoxane | Sandostatin |
| Bleomycin | Sandostatin LAR |
| Bortezomib | Sargramostim |
| Busulfan | Solu-Cortef |
| Busulfex | Solu-Medrol |
| C225 | STI-571 |
| Calcium Leucovorin | Streptozocin |
| Campath | Tamoxifen |
| Camptosar | Targretin |
| Camptothecin-11 | Taxol |
| Capecitabine | Taxotere |
| Carac | Temodar |
| Carboplatin | Temozolomide |
| Carmustine | Teniposide |
| Carmustine wafer | TESPA |
| Casodex | Thalidomide |
| CCNU | Thalomid |
| CDDP | TheraCys |
| CeeNU | Thioguanine |
| Cerubidine | Thioguanine Tabloid |
| cetuximab | Thiophosphoamide |
| Chlorambucil | Thioplex |
| Cisplatin | Thiotepa |
| Citrovorum Factor | TICE |
| Cladribine | Toposar |
| Cortisone | Topotecan |
| Cosmegen | Toremifene |
| CPT-11 | Trastuzumab |
| Cyclophosphamide | Tretinoin |
| Cytadren | Trexall |
| Cytarabine | Trisenox |
| Cytarabine liposomal | TSPA |
| Cytosar-U | VCR |
| Cytoxan | Velban |
| Dacarbazine | Velcade |
| Dactinomycin | VePesid |
| Darbepoetin alfa | Vesanoid |
| Daunomycin | Viadur |
| Daunorubicin | Vinblastine |
| Daunorubicin hydrochloride | Vinblastine Sulfate |
| | Vincasar Pfs |
| Daunorubicin liposomal | Vincristine |
| DaunoXome | Vinorelbine |
| Decadron | Vinorelbine tartrate |
| Delta-Cortef | VLB |
| Deltasone | VP-16 |
| Denileukin diftitox | Vumon |
| DepoCyt | Xeloda |
| Dexamethasone | Zanosar |
| Dexamethasone acetate | Zevalin |
| dexamethasone sodium phosphate | Zinecard |
| | Zoladex |
| Dexasone | Zoledronic acid |
| Dexrazoxane | Zometa |
| DHAD | Gliadel wafer |
| DIC | Glivec |
| Diodex | GM-CSF |
| Docetaxel | Goserelin |
| Doxil | granulocyte - colony stimulating factor |
| Doxorubicin | Granulocyte macrophage colony stimulating factor |
| Doxorubicin liposomal | |
| Droxia | Halotestin |
| DTIC | Herceptin |
| DTIC-Dome | Hexadrol |
| Duralone | Hexalen |
| Efudex | Hexamethylmelamine |
| Eligard | HMM |
| Ellence | Hycamtin |
| Eloxatin | Hydrea |
| Elspar | Hydrocort Acetate |
| Emcyt | Hydrocortisone |
| Epirubicin | Hydrocortisone sodium phosphate |
| Epoetin alfa | Hydrocortisone sodium succinate |
| Erbitux | Hydrocortone phosphate |
| Erwinia L-asparaginase | Hydroxyurea |
| Estramustine | Ibritumomab |
| Ethyol | Ibritumomab Tiuxetan |
| Etopophos | Idamycin |
| Etoposide | Idarubicin |
| Etoposide phosphate | Ifex |
| Eulexin | IFN-alpha |
| Evista | Ifosfamide |
| Exemestane | IL-2 |
| Fareston | IL-11 |
| Faslodex | Imatinib mesylate |
| Femara | Imidazole Carboxamide |
| Filgrastim | Interferon alfa |
| Floxuridine | Interferon Alfa-2b (PEG conjugate) |
| Fludara | Interleukin-2 |
| Fludarabine | Interleukin-11 |
| Fluoroplex | Intron A (interferon alfa-2b) |
| Fluorouracil | Leucovorin |
| Fluorouracil (cream) | Leukeran |
| Fluoxymesterone | Leukine |
| Flutamide | Leuprolide |
| Folinic Acid | Leurocristine |
| FUDR | Leustatin |
| Fulvestrant | Liposomal Ara-C |
| G-CSF | Liquid Pred |
| Gefitinib | Lomustine |
| Gemcitabine | L-PAM |
| Gemtuzumab ozogamicin | L-Sarcolysin |
| Gemzar | Meticorten |
| Gleevec | Mitomycin |
| Lupron | Mitomycin-C |
| Lupron Depot | Mitoxantrone |
| Matulane | M-Prednisol |
| Maxidex | MTC |
| Mechlorethamine | MTX |
| Mechlorethamine Hydrochlorine | Mustargen |
| | Mustine |
| Medralone | Mutamycin |
| Medrol | Myleran |
| Megace | Iressa |
| Megestrol | Irinotecan |
| Megestrol Acetate | Isotretinoin |
| Melphalan | Kidrolase |
| Mercaptopurine | Lanacort |
| Mesna | L-asparaginase |
| Mesnex | LCR |
| Methotrexate | |
| Methotrexate Sodium | |
| Methylprednisolone | |
| Mylocel | |
| Letrozole | |

In certain embodiments, interferons (IFNs) can be used in combinations with the compounds of the present invention. Suitable intereferons include: interferon alpha-2a, interferon alpha-2b, pegylated interferon alpha, including interferon alpha-2a and interferon alpha 2b, interferon beta, interferon gamma, interferon tau, interferon omega, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and/or interferon gamma-1☐ by InterMune.

In one embodiment TCN, TCN-P or a related compound and an erlotinib-like compound, for example, gefitinib, erlotinib or a salt thereof as disclosed herein can be used in combination or alternation with additional chemotherapeutic agents, such as those described herein or in Table 3, for the treatment of drug resistant cancer, for example multiple drug resistant cancer. Drug resistant cancers can include cancers of the colon, bone, kidney, adrenal, pancreas, liver and/or any other cancer known in the art or described herein. In one embodiment, the additional chemotherapeutic agent can be a P-glycoprotein inhibitor. In certain non-limiting embodiments, the P-glycoprotein inhibitor can be selected from the following drugs: verapamil, cyclosporin (such as cyclosporin A), tamoxifen, calmodulin antagonists, dexverapamil, dexniguldipine, valspodar (PSC 833), biricodar (VX-710), tariquidar (XR9576), zosuquidar (LY335979), laniquidar (R101933), and/or ONT-093.

7. Pharmaceutical Compositions

The compositions including triciribine compounds and an erlotinib-like compound, for example, gefitinib, erlotinib or a salt thereof can optionally be administered with a pharmaceutical carrier or excipient. Pharmaceutical carriers suitable for administration of the compounds provided herein include any such carriers known to those skilled in the art to be suitable for the particular mode of administration. The triciribine compounds and in combination with an erlotinib-like compound, for example, gefitinib, erlotinib or a salt thereof may be formulated as the sole pharmaceutically active ingredients in the composition or may be combined.

Compositions including the triciribine compounds and an erlotinib-like compound, for example, gefitinib, erlotinib or a salt thereof may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration. Preferably the compositions are administered intravenously.

The compositions may conveniently be presented in unit dosage form and may be prepared by conventional pharmaceutical techniques. Such techniques include the step of bringing into association one or more compositions of the present invention and one or more pharmaceutical carriers or excipients.

The triciribine compounds and an erlotinib-like compound, for example, gefitinib, erlotinib or a salt thereof and compositions thereof can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the triciribine compounds described above are formulated into pharmaceutical compositions using techniques and procedures well known in the art (see, e.g., Ansel, Introduction to Pharmaceutical Dosage Forms, Fourth Ed., 1985, p. 126).

In the compositions, effective concentrations of one or more compounds or pharmaceutically acceptable derivatives thereof may be mixed with one or more suitable pharmaceutical carriers. The compounds of the invention may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing a triciribine compound and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa.

Compositions of the present invention suitable for topical administration in the mouth include for example, lozenges, having the ingredients in a flavored basis, usually sucrose and acacia or tragacanth; pastilles, having one or more triciribine compounds and an erlotinib-like compound, for example, gefitinib, erlotinib or a salt thereof of the present invention in an inert basis such as gelatin and glycerin, or sucrose and acacia; and mouthwashes, having one or more of the compositions of the present invention administered in a suitable liquid carrie The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base including, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions including triciribine compounds and an erlotinib-like compound, for example, gefitinib, erlotinib or a salt thereof may be used in combination with one or more pharmaceutically acceptable carrier mediums and/or excipients. As used herein, "pharmaceutically acceptable carrier medium" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions including triciribine compounds and an erlotinib-like compound, for example, gefitinib, erlotinib or a salt thereof may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; the triciribine compound and/or the an erlotinib-like compound, for example, gefitinib, erlotinib or a salt thereof used in combination or coincidential with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions including triciribine compounds and an erlotinib-like compound, for example, gefitinib, erlotinib or a salt thereof are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered ingredient. For example, approximately 1-5 mg per day of a compound disclosed herein can reduce the volume of a solid tumor in mice.

The dosage will depend on host factors such as weight, age, surface area, metabolism, tissue distribution, absorption rate and excretion rate. In one embodiment, approximately 0.5 to 7 grams per day of a triciribine compound disclosed herein may be administered to humans. Optionally, approximately 1 to 4 grams per day of the compound can be administered to humans. In certain embodiments 0.001-5 mg/day is administered to a human. The therapeutically effective dose level will depend on many factors as noted above. In addition, it is well within the skill of the art to start doses of the composition at relatively low levels, and increase the dosage until the desired effect is achieved.

Compositions including triciribine compounds and an erlotinib-like compound, for example, gefitinib, erlotinib or a salt thereof may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The triciribine compounds and an erlotinib-like compound, for example, gefitinib, erlotinib or a salt thereof may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The triciribine compounds and an erlotinib-like compound, for example, gefitinib, erlotinib or a salt thereof may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

Compositions including the triciribine compounds and an erlotinib-like compound, for example, gefitinib, erlotinib or a salt thereof may be used in combination with other compositions and/or procedures for the treatment of the conditions described above. For example, a tumor may be treated conventionally with surgery, radiation, or chemotherapy combined with one or more compositions of the present invention and then one or more compositions of the present invention may be subsequently administered to the patient to extend the dormancy of micrometastases and to stabilize, inhibit, or reduce the growth of any residual primary tumor.

7.1. Additional Embodiments

The pharmaceutical compositions including triciribine compounds and an erlotinib-like compound, for example, gefitinib, erlotinib or a salt thereof can be formulated according to known methods for preparing pharmaceutically useful compositions. Formulations are described in a number of sources which are well known and readily available to those skilled in the art. For example, Remington's Pharmaceutical Sciences, Mack Publishing Company, Easton, Pa. describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The methods of the present invention, for example, for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer, such as administration of an anti-cancer agent.

Administration of API-2 (triciribine) as a salt may be carried out. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The triciribine compounds and an erlotinib-like compound, for example, gefitinib, erlotinib or a salt thereof can be formulated as pharmaceutical compositions and administered to a subject, such as a human or veterinary patient, in a variety of forms adapted to the chosen route of administration, i.e., orally or parenterally, by intravenous, intramuscular, topical or subcutaneous routes.

Thus, the triciribine compounds and an erlotinib-like compound, for example, gefitinib, erlotinib or a salt thereof of the present invention may be systemically administered, e.g., orally, in combination with a pharmaceutically acceptable vehicle (i.e., carrier) such as an inert diluent or an assimilable edible carrier. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of the active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compounds of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds of the invention may be incorporated into sustained-release preparations and devices.

The triciribine compounds and an erlotinib-like compound, for example, gefitinib, erlotinib or a salt thereof may also be administered intravenously or intraperitoneally by infusion or injection. Solutions of the active agents or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders including the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the triciribine compounds and an erlotinib-like compound, for example, gefitinib, erlotinib or a salt thereof may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one non-limiting embodiment, the concentration of the active agent in a liquid composition, such as a lotion, can be from about 0.1-25 wt.-%, or from about 0.5-10 wt.-%. In one embodiment, the concentration in a semi-solid or solid composition such as a gel or a powder can be about 0.1-5 wt.-%, preferably about 0.5-2.5 wt.-%. In one embodiment, single dosages for injection, infusion or ingestion will generally vary between 5-1500 mg, and may be administered, i.e., 1-3 times daily, to yield levels of about 0.1-50 mg/kg, for adults. A non-limiting dosage of the present invention can be between 7.5 to 45 mg per clay, administered orally, with appropriate adjustment for the body weight of an individual.

Accordingly, the present invention includes a pharmaceutical composition including triciribine compounds and an erlotinib-like compound, for example, gefitinib, erlotinib or a salt thereof in combination with a pharmaceutically acceptable carrier. Pharmaceutical compositions adapted for oral, topical or parenteral administration, including an amount of triciribine compounds and an erlotinib-like compound, for example, gefitinib, erlotinib or a salt thereof, constitute a preferred embodiment of the invention. The dose administered to a subject, particularly a human, in the context of the present invention should be sufficient to affect a therapeutic response in the patient over a reasonable time frame. One skilled in the art will recognize that dosage will depend upon a variety of factors including the condition of the animal, the body weight of the animal, as well as the severity and stage of the cancer.

A suitable dose is that which will result in a concentration of the triciribine compounds and an erlotinib-like compound, for example, gefitinib, erlotinib or a salt thereof in tumor tissue which is known to affect the desired response. The preferred dosage is the amount which results in maximum inhibition of cancer cell growth, without unmanageable side effects. Administration of API-2 (or a pharmaceutically acceptable salt thereof) can be continuous or at distinct intervals, as can be determined by a person of ordinary skill in the art.

Mammalian species which benefit from the disclosed methods for the inhibition of cancer cell growth, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used herein interchangeably and are intended to include such human and non-human mammalian species. Likewise, in vitro methods of the present invention can be earned out on cells of such mammalian species.

Patients in need of treatment using the methods of the present invention can be identified using standard techniques known to those in the medical profession.

The following examples are offered by way of illustration and not by way of limitation.

8. EXAMPLES

Example 1: In Vitro Screening

Cell Lines and NCI Diversity Set. All cell lines can be purchased from ATCC or described previously (Cheng J. Q. et al., Oncogene, 1997. 14: p. 2793-2801; West, K. A. et al., Drug Resist Updat, 2002. 5: p. 234-248; Satyamoorthy K. et al., Cancer Res, 2001. 61: p. 7318-7324). The NCI Structural Diversity Set is a library of 1,992 compounds selected from the approximately 140,000-compound NCI drug depository. In-depth data on the selection, structures, and activities of these diversity set compounds can be found on the NCI Developmental Therapeutics Program web site.

Screening for Inhibition of Akt-transformed Cell Growth.

AKT2 transformed NIH3T3 cells or LXSN vector-transfected NIH3T3 control cells (Cheng J. Q. et al., Oncogene, 1997. 14: p. 2793-2801) are plated into 96-well tissue culture plate. Following treatment with 5 μM of NCI Diversity Set compound, cell growth can be detected with CellTier 96 One Solution Cell Proliferation kit (Promega). Compounds that inhibit growth in AKT2-transformed but not LXSN-transfected NIH3T3 cells are considered as candidates of Akt inhibitor and subjected to further analysis.

In vitro Protein Kinase, Cell Survival and Apoptosis Assays.

In vitro kinase is performed as previously described (see, for example, Jiang K. et al., Mol Cell Biol, 2000. 20: p. 139-148). Cell survival is assayed with MTS (Promega). Apoptosis was detected with annexin V, which is performed as previously described (Jiang K. et al., Mol Cell Biol, 2000. 20: p. 139-148). Recombinant Akt and PDK1 are purchased from Upstate Biotechnology Inc.

Results

Identification of Small Molecule Inhibitor of Akt Signaling Pathway, API-2.

Frequent alterations of Akt has been detected in human cancer and disruption of Akt pathway induces apoptosis and inhibits tumor growth (Jetzt A. et al., Cancer Res, 2003. 63: p. 697-706, 2003). Thus, Akt is considered as an attractive molecular target for development of novel cancer therapeutics. To identify small molecule inhibitor(s) of Akt, a chemical library of 1,992-compounds from the NCI (the NCI Diversity Set) is evaluated for agents capable of inhibition of growth in AKT2-transformed but not empty vector LXSN-transfected NIH3T3 cells. Repeated experiments showed that 32 compounds inhibited growth only in AKT2-transformaed cells. The most potent of these compounds, API-2 (NCI identifier: NSC 154020), can suppress cell growth at a concentration of 50 nM. FIG. 1A shows the chemical structure of API-2, which is also known as triciribine (Schweinsberg P. D. et al., Biochem Pharmacol, 1981. 30: p. 2521-2526). The fact that API-2 inhibits selectively AKT-2 transformed cells over untransformed parental cells prompted us to determine whether API-2 is an inhibitor of AKT2 kinase. To this end, AKT2 is immunoprecipitated with anti-AKT2 antibody from AKT-2 transformed NIH3T3 cells following treatment with API-2. AKT2 immunoprecipitates were immunoblotted with anti-phospho-Akt antibodies. As shown in FIG. 1B, API-2 significantly inhibited AKT2 phosphorylation at both threonine-309 and serine-474, which are required for full activation of AKT2 (Datta S. R. et al., Genes Dev, 1999. 13: p. 2905-2927). As three isoforms of Akt share high homology and similar structure, the effect of API-2 on their kinase activities is evaluated. HEK293 cells are transfected with HA-Akt1, -AKT2 and -AKT3, serum-starved overnight and treated with API-2 for 60 min prior to EGF (50 ng/ml) stimulation. Triple experiments showed that API-2 suppressed EGF-induced kinase activity and phosphorylation of Akt1, AKT2 and AKT3 (FIG. 1C). However, kinase activity of recombinant constitutively active AKT2 (Myr-AKT2) is not inhibited by API-2 in an in vitro kinase reaction (FIG. 1D), suggesting that API-2 does not directly inhibit Akt in vitro and that API-2 neither functions as ATP competitor nor as the substrate competitor that binds to active site of Akt.

API-2 Does Not Inhibit Known Upstream Activators of Akt.

It has been well documented that Akt is activated by extracellular stimuli and intracellular signal molecules, such as active Ras and Src, through a PI3K-dependent manner. Therefore, API-2 inhibition of Akt could result from targeting upstream molecule(s) of Akt. As PI3K and PDK1 are direct upstream regulators of Akt (Datta S. R. et al., Genes Dev, 1999. 13: p. 2905-2927), whether API-2 inhibits PI3K and/or PDK1 is examined. HEK293 cells are serum-starved and then can be treated with API-2 or PI3K inhibitor, wortmannin, for 30 min prior to EGF stimulation. PI3K is immunoprecipitated with anti-p110□□□ antibody. The immunoprecipitates are subjected to in vitro PI3K kinase assay using PI-4-P as a substrate. As shown in FIG. 2A, the EGF-induced PI3K activity is inhibited by wortmannin but not by API-2. To evaluate the effect of API-2 on PDK1, an assay in which recombinant PDK1 promotes the threonine-309 phosphorylation of AKT2 peptides is used in the presence of lipid vesicles containing phosphotidylinositol. As shown in FIG. 2B, the assay is potently inhibited by the control PDK1 inhibitor staurosporine (IC50=5 nM). In contrast, API-2 displayed only 21% inhibition of the assay at the highest concentration tested (5.1 μM). To further evaluate the effect of API-2 on PDK1 activation, the autophosphorylation level of PDK1 at serine-241, a residue that is phosphorylated by itself and is critical for its activity is examined (Datta S. R. et al., Genes Dev, 1999. 13: p. 2905-2927), following API-2 treatment of HEK293 cells. Triplicate experiments show that phosphorylation levels of PDK1 are not inhibited by API-2 (FIG. 2B). However, PI3K inhibitor wortmannin can inhibit EGF-stimulated PDK1 (FIG. 2B).

API-2 is Highly Selective for the Akt over PKC, PKA, SGK, STAT, JNK, p38, and ERK Signaling Pathways.

Akt belongs to AGC (PKA/PKG/PKC) kinase family, which also include PKA, PKC, serum- and glucocorticoid-inducible kinase (SGK), p90 ribosomal S6 kinase, $p70^{S6K}$, mitogen- and stress-activated protein kinase and PKC-related kinase. Among AGC kinase family, protein structures of PKA, PKC and SGK are more close to Akt kinase than other members. Therefore, next examined are the effects of API-2 on the enzymatic activities of these 3 kinases. HEK293 cells are transfected with HA-tagged PKA, PKCα, □ or SGK. In vitro kinase assay and immunoblotting analysis show that the kinase activities of PKA and PKC□□ are inhibited by PKAI and Ro 31-8220, a PKC inhibitor, respectively, whereas API-2 exhibits no effect on their activities (FIGS. 2C and 2E). Further, serum-induced SGK kinase activity is attenuated by wortmannin but not by API-2 (FIG. 2D). In addition, it is determined whether API-2 has effect on other oncogenic survival pathways. Western blotting analyses with commercially available anti-phospho-antibodies reveals that phosphorylation levels of Stat3, JNK, p38 and Erk1/2 were not affected by API-2 treatment (FIG. 2F). These data indicate that API-2 specifically inhibits Akt signaling pathway.

API-2 Suppresses Cell Growth and Induces Apoptosis in Akt-Overexpressing/Activating Human Cancer Cell Lines.

The ability of API-2 to selectively inhibit the Akt pathway suggests that it should inhibit proliferation and/or induces apoptosis preferentially in those tumor cells with aberrant expression/activation of Akt. As activation of Akt in human malignancies commonly results from overexpression of Akt or PTEN mutations, API-2 is used to treat the cells that express constitutively active Akt, caused by overexpression of AKT2 (OVCAR3, OVCAR8, PANC1 and AKT2-transformed NIH3T3) or mutations of the PTEN gene (PC-3, LNCaP, MDA-MB-468), and cells that do not (OVCAR5, DU-145, T47D, COLO357 and LXSN-NIH3T3) as well as melanoma cells that are activated by IGF-1 to activate Akt or do not respond to growth stimulation by IGF-1 (Satyamoorthy K. et al., Cancer Res, 2001. 61: p. 7318-7324). Immunoblotting analysis showed that phosphorylation levels of Akt are inhibited by API-2 only in the cells expressing elevated Akt or responding to IGF-1 simulation (FIG. 3A). Accordingly, API-2 inhibited cell growth to a much higher degree in Akt-overexpressing/activating cells as compared to those with low levels of Akt. As shown in FIG. 3B, API-2 treatment inhibited cell proliferation by approximately 50-60% in Akt-overexpressing/activating cell lines, LNCaP, PC-3, OVCAR3, OVCA8, PANC1, MDA-MB-468, and WM35, whereas only by about 10-20% in DU145, OVCAR5, COL0357, T47D and WM852 cells, which exhibit low levels of Akt or do not respond to growth stimulation by IGF-1. Moreover, API-2 induces apoptosis by 8-fold (OVCAR3), 6-fold (OVCAR8), 6-fold (PANC1), and 3-fold (AKT2-NIH3T3). No significant difference of apoptosis is observed between API-2 and vehicle (DMSO) treatment in OVCAR5, COLO357 and LXSN-NIH3T3 cells. Thus, API-2 inhibits cell growth and induces apoptosis preferentially in cells that express aberrant Akt.

API-2 Inhibits Downstream Targets of Akt.

It has been shown that Akt exerts its cellular effects through phosphorylation of a number of proteins (Datta S. R. et al., Genes Dev, 1999. 13: p. 2905-2927). More than 20 proteins have been identified as Akt substrates, including the members of Forkhead protein family (FKHR, AFX and FKHRL1), tuberlin/TSC2, p70$^{S6K}$, GSK-3☐, p21$^{WAF1/CiP1}$, p27$^{kip1}$, MDM2, Bad, ASK1 and IKK☐☐ etc. It is next examined whether API-2 inhibits downstream targets of Akt. As anti-phospho-tuberlin, -Bad, -AFX, and -GSK-3β antibodies are commercially available, therefore, the effect of API-2 on their phosphorylation induced by Akt was determined. Following API-2 (1 μM) treatment, OVCAR3 cells was lysed and immunoblotted with the individual anti-phospho-antibody. FIG. 4A shows that API-2 considerably inhibited the phosphorylation levels of tuberlin leading to stabilization and upregulation of tuberin (Dan, H. C., et al., J Biol Chem, 2002. 277: p. 35364-35370). The phosphorylation levels of Bad, GSK-3β, and AFX are partially attenuated by API-2. These data suggest that API-2 induces cell death and cell growth arrest by inhibiting phosphorylation of its downstream targets. API-2 inhibition of Akt downstream targets at different degrees could be due to the fact that phosphorylation sites of these targets are also regulated by other kinase(s), for instance, Bad serine-136 is phosphorylated by PAK1 in addition to Akt (Schurmann, A., et al. Mol Cell Biol, 2000. 20: p. 453-461).

Example 2: Antitumor Activity in the Nude Mouse Tumor Xenograft Model

Tumor cells can be harvested, suspended in PBS, and can be injected s.c. into the right and left flanks (2×10$^6$ cells/flank) of 8-week-old female nude mice as reported previously (Sun, J. et al., Cancer Res, 1999. 59: p. 4919-4926, 1999). When tumors reach about 100-150 mm$^3$, animals are randomized and dosed i.p. with 0.2 ml vehicle of the triciribine compound and/or an erlotinib-like compound, for example, gefitinib, erlotinib or a salt thereof, daily. Control animals receive DMSO (20%) vehicle, whereas treated animals can be injected with API-2 (1 mg/kg/day) in 20% DMSO.

API-2 Inhibits the Growth of Tumors in Nude Mice that Overexpress Akt.

Frequent overexpression/activation and/or amplification of AKT1 and AKT2 in human ovarian and pancreatic cancer was shown (Cheng J. Q. and Nicosia S. V., in *Encyclopedic Reference of Cancer*, 2001, Schwab D, Ed. Springer, Berlin Heidelberg and New York, p. 35-7). Inhibition of Akt pathway by inhibitors of PI3K, HSP70, Src and farnesyltransferase resulted in cell growth arrest and induction of apoptosis (Solit D. B. et al., Cancer Res, 2003. 63: p. 2139-2144; Xu, W., et al. Cancer Res, 2003.63: p. 7777-7784). A recent study showed that the tumor growth of xenografts with elevated Akt was also significantly inhibited by intratumoral injection of adenovirus of dominant negative Akt (Jetzt A. et al., Cancer Res, 2003. 63: p. 697-706, 2003). Because API-2 inhibits Akt signaling and induces apoptosis and cell growth arrest only in cancer cells with elevated levels of Akt (FIG. 3), the growth of tumors with elevated levels of Akt should be more sensitive to API-2 than that of tumors with low levels of Akt in nude mice. To this end, s.c. Akt-overexpressing cells (OVCAR3, OVCAR8 and PANC-1) are s.c. implanted into the right flank, and those cell lines that express low levels of Akt (OVCAR5 and COL0357) into the left flank of mice. When the tumors reach an average size of about 100-150 mm$^3$, the animals are randomized and treated i.p. with either vehicle or API-2 (1 mg/kg/day). As illustrated in FIG. 4B, OVCAR-5 and COL0357 tumors treated with vehicle grew to about 800-1,000 mm$^3$ 49 days after tumor implantation. OVCAR3, OVCAR8 and PANC1 tumors treated with vehicle control grew to about 700-900 mm$^3$ 49 days after tumor implantation. API-2 inhibited OVCAR3, OVCAR8 and PANC1 tumor growth by 90%, 88% and 80%, respectively. In contrast, API-2 has little effect on the growth of OVCAR5 and COL0357 cells in nude mice (FIGS. 4B-4D and data not shown). At dose 1 mg/kg/day, API-2 had no effects on blood glucose level, body weight, activity and food intake of mice. In treated tumor samples, Akt activity was inhibited by API-2 without change of total Akt content (FIG. 4E). Taken together, these results indicate that API-2 selectively inhibits the growth of tumors with elevated levels of Akt.

Example 3: TCN Directly Inhibits Wild Type Akt Kinase Activity

API-2 (TCN) can directly inhibit wild type Akt kinase activity induced by PDK1 in vitro (FIG. 1). This result supports that API-2 is a direct Akt inhibitor and that the underlying mechanism may be API-2 binding to PH domain and/or threonine-308 of Akt. An in vitro kinase assay is performed with recombinant of PDK1 and Akt in a kinase buffer containing phosphatidylinositol-3,4,5-P3 (PIP3), API-2 and histone H2B as substrate. After incubation of 30 min, the reactions were separated by SDS-PAGE and exposed in a film.

Example 4: TCN is Effective in Cancer Resistant Cells

The effects of TCN (API-2) are tested in cisplatin, paclitaxel, and tamoxifen resistant A270CP, C-13, OVCAR433 and MCF7/TAM cells. API-2 overcame cisplatin, paclitaxel, and tamoxifen resistance in these cells.

Example 5: TCN Potentiates Growth Inhibition by Trastuzumab and Induces Apoptosis Materials and Methods
Cell Lines and Cell Cultures.
The tumorigenic BT474.ml subline maintained in Dulbecco's modified Eagle's medium: Ham's F-12 medium (1:1) with 8-10% FBS.

Antibodies and Reagents.
Trastuzumab was a gift from Genentech (San Francisco, Calif.). RAD001 (everolimus) was a gift from Novartis (East Hanover, N.J.). QLT0267 and KP 372-1 were gifts from QLT Inc. (Vancouver, BC). Triciribine (6-Amino4-methyl-8-((3-D-ribofuranosyl)-4H,8H-pyrrolo[4,3,2-de]pyrimido[4,5-c]pyridazine) was purchased from Berry & Associates, Inc. (Ann Arbor, Mich.). Edelfosine was purchased from Calbiochem (San Diego, Calif.). A selective Akt inhibitor, 4ADPIB (4-amino-2(3,4-dichloro-phenyl)-N-(1H-indazol-5-yl)-butyramide) (U.S. Pat. No. 6,919,340), was synthesized. PTEN antibodies were from Santa Cruz Biotechnology (Santa Cruz, Calif.). 3-actin antibodies were from Sigma (St. Louis, Mo.). All other antibodies were purchased from Cell Signaling Technology (Danvers, Mass.).

PTEN Antisense and Non-Specific Oligonucleotide Transient Transfection.
Antisense (AS) oligonucleotides specific for PTEN, control non-specific (NS) oligonucleotides and procedures for transfection were followed according to Nagata Y. et al., Cancer Cell, 2004. 6(2): p. 117-27.

Cell Proliferation Assay.
PTEN AS/NS transfected BT474.ml cells were plated 2500 cells/0.32 $cm^2$ well. Cells were treated with inhibitors of the Akt/mTOR pathway alone or in combination with trastuzumab as described for 5 days and viable cells were measured by MTS assay using the CellTiter 96 AQ nonradioactive cell proliferation assay kits according to the manufacturer's protocol (Promega, Madison, Wis.). Treated cells were compared to control DMSO treated BT474.ml cells to calculate percentage of growth inhibition.

APO-BRDU TUNEL Assay.
The PTEN AS and NS transfected BT474.ml cells were plated in 6-well plates (4-6×$10^5$ cells/well). Twenty-four hours after plating, the cells were treated as indicated for 72 hours with trastuzumab, TCN and/or RAD001. The floating and adherent cells were collected, labeled and stained using the APO-BRDU™ TUNEL assay kit (Phoenix Flow Systems, San Diego, Calif.) according to the manufacturer's protocol. Data was collected and analyzed using a FACScan flow cytometer and CellQuest Pro 4.02 software (Becton Dickinson, Franklin Lakes, N.J.). At least 10,000 events were examined.

SDS-PAGE and Immunoblot Analysis.
Cells transfected with PTEN AS/NS oligonucleotides were treated as indicated. Immunoblotting was performed as described by Nagata Y. et al., Cancer Cell, 2004. 6(2): p. 117-27.

Results
Triciribine and RAD001 Potentiate Growth Inhibition by Trastuzumab in PTEN-Deficient Cells.
To find a strategy to overcome trastuzumab resistance, particularly resistance caused by PTEN loss, 6 different small molecule inhibitors were tested, which directly or indirectly targeted the PI3K/Akt/mTOR signal transduction pathway, a major pathway activated by overexpression of ErbB2 and the loss of PTEN. The goal was to identify compounds that would exhibit synergistic effects with trastuzumab, preferably at a low dose of the compound in order to minimize toxicity. The drugs chosen targeted Akt, mTOR and integrin-linked kinase (ILK) (FIG. 9A). BT474.ml cells are a tumorigenic subline of the BT474 breast cancer cell line and express high levels of ErbB2. When PTEN levels are decreased by transfection with PTEN antisense oligonucleotides (PTEN AS), BT474.ml breast cancer cells become more resistant to the anti-proliferative effects of trastuzumab than cells with normal levels of PTEN and provide a good experimental model for breast cancers in which trastuzumab resistance is caused by PTEN loss (Nagata Y. et al., Cancer Cell, 2004. 6(2): p. 117-27 and FIGS. 9B and 9C). Nonspecific oligonucleotides (NS) were transfected as controls. Treatment with PTEN AS oligonucleotides effectively lowered PTEN levels (FIGS. 11A and 11B). Neither PTEN AS nor NS control oligonucleotides altered ErbB2 levels in the cells.

PTEN AS and NS-transfected BT474.ml cells were treated with each of the 6 compounds or trastuzumab alone and in combination for 5 days and evaluated cell proliferation as compared to DMSO-treated control. Using growth inhibition as a biological endpoint, we compared the ability of each drug to exhibit cooperative effects with trastuzumab using doses of drug that resulted in −20-40% growth inhibition when administered alone (FIG. 9A).

Almost all of the compounds displayed growth inhibitory effects, particularly at high concentrations and in cells with intact PTEN (FIG. 9A). However, two of the compounds, triciribine and RAD001, markedly enhanced growth inhibition in the PTEN AS cells when combined with trastuzumab as compared to trastuzumab or either compound alone (FIG. 9A). Triciribine (also called API-2), a compound that inhibits Akt activation, potentiated growth inhibition by trastuzumab over a 20-fold concentration range (FIG. 9B). The mTOR inhibitor RAD001 (everolimus) increased growth inhibition by trastuzumab when RAD001 was administered at low doses (<1 nM) (FIG. 9C). Strikingly, triciribine and RAD001 were able to cooperate with trastuzumab to inhibit cell growth at similar levels in the PTEN AS and NS cells (FIGS. 9B and 9C). In essence, triciribine and RAD001 were able to restore trastuzumab sensitivity to PTEN-deficient cells. Triciribine and RAD001 were also effective as single agents, both in PTEN AS and NS cells, at doses greater than 5 mM and 1.5 nM for triciribine and RAD001, respectively (FIGS. 9B and 9C).

A third compound, the ILK inhibitor QLT0267, potentiated growth inhibition by trastuzumab within a narrow dose range (~5-15 pM)(FIG. 9A). Because the dose range in which QLT0267 exhibited cooperative effects with trastuzumab was narrow, this compound further was not investigated further. At concentrations greater than 20 pM, QLT0267 had no cooperative effect with trastuzumab but significantly inhibited cell growth as a single agent.

Induction of Apoptosis Following Combination Treatment.
To assess if growth inhibition was accompanied by apoptosis, we treated PTEN AS and NS transfected BT474.ml cells with triciribine, RAD001 and trastuzumab, alone or combined, and quantified the levels of apoptosis (FIG. 10). RAD001 did not significantly induce apoptosis alone or in combination with trastuzumab. Although the number of TUNEL-positive, apoptotic cells increased slightly following treatment with trastuzumab or triciribine alone, this increase was not statistically significant. However, the combination of triciribine and trastuzumab, significantly induced apoptosis as compared with all other treatments in both PTEN AS and NS transfected cells (FIG. 10).

Example 6: TCN Inhibits Activation of Akt and mTOR Inhibition of Downstream Signaling Molecules Immunoblot analysis verified that triciribine and RAD001 blocked activation of Akt and mTOR, important signaling molecules activated by ErbB2 and the targets of triciribine and RAD001 respectively. Phosphorylation of Akt on Thr308 and Ser473 was analyzed as an indicator of Akt activity and mTOR activity was assessed by the phosphorylation of p70S6K (70-kDa ribosomal protein S6 kinase), an mTOR target. After triciribine treatment, phosphorylation of Akt on both sites was substantially decreased (FIG. 11A). In PTEN-deficient cells, the levels of Akt phosphorylation following triciribine and trastuzumab combination treatment were similar to those seen in cells with intact PTEN (FIG. 11A, lanes 4&8). Thus, triciribine overcame the adverse effects of PTEN loss by effectively blocking Akt activation. RAD001 dramatically blocked phosphorylation of p70S6K (FIG. 11B). However, RAD001 combined with trastuzumab did not lower p70S6K phosphorylation beyond that seen with RAD001 alone (FIG. 11B). A feedback loop has been recently identified which results in Akt phosphorylation and activation following treatment with mTOR inhibitors, such as RAD001 (O'Reilly K. E. et al., Cancer Res, 2006. 66(3): p. 1500-8). It was also observed that feedback activation of Akt by RAD001 and combination therapy with trastuzumab and RAD001 eliminated Akt phosphorylation by this feedback loop (FIG. 11B, lanes 3 vs. 4), consistent with the notion that Akt activation following mTOR inhibition is dependent on upstream receptor tyrosine kinases (O'Reilly K. E. et al., Cancer Res, 2006. 66(3): p. 1500-8). In summary, both drugs inhibited their predicted target kinases and combination treatment had a larger inhibitory effect on the Akt/mTOR signaling pathway than any single agent, even in PTEN-deficient cells.

Example 7: TCN and Trastuzumab Inhibit Tumor Growth in PTEN-Deficient Tumors

Materials and Methods
Xenograft Human Tumor Model in SCID Mice.
Female, 6-week-old, severe combined immunodeficiency (SCID) mice were from Taconic Farms (Hudson, N.Y.). Tumor xenografts were performed as described in Nagata Y. et al., Cancer Cell, 2004. 6(2): p. 117-27. When the xenograft tumors reached the average size of 100-150 mm$^3$, the mice were divided into 6 groups, each with 7 mice and an even distribution of tumor sizes, and treated as follows. PTEN antisense (30 pg) oligonucleotides were administered to each mouse weekly via intratumor injection. One week after PTEN AS oligonucleotide administration was initiated, drug treatment began. Trastuzumab was given at a dose of 0.5 mg/kg twice a week in 200 pL saline through intratumor injection at multiple sites. Triciribine was given at a dose of 0.5 mg/kg/day in 200 pL 20% DMSO saline solution through intraperitoneal (I.P.) injection. RAD001 was given via gavage at a dose of 1 pg/kg in 500 pL 5% glucose water twice a week. 20% DMSO saline solution (200 pL/day) was given through I.P. injection. The tumors were measured twice weekly with calipers and the volume of the tumors was calculated as: volume=length×width$^2$/2.

Statistical Analysis.
One-way ANOVA was performed using GraphPad Prism 3.0 for Windows (Graph Pad Software, San Diego, Calif.).

Results
The earlier biological and molecular data were very promising, however, in vivo studies provide the most stringent test for therapeutic efficacy. Therefore, triciribine and RAD001 were tested in vivo. BT474.ml cell xenografts were injected into the mammary fat pad of 6-week-old SCID mice. After tumors formed, the mice received PTEN AS weekly via intratumor injection. This protocol effectively models PTEN-deficient tumors in vivo (Nagata Y. et al., Cancer Cell, 2004. 6(2): p. 117-27). The mice were randomized into treatment groups receiving triciribine, RAD001, trastuzumab or DMSO alone or in combination. After treatment, the growth patterns of the tumors treated with DMSO, trastuzumab, RAD001, or triciribine alone were similar (FIGS. 12A and 12B). Growth of the tumors was not inhibited and the mice were euthanized after 3 weeks due to large tumor burdens. In contrast, combination treatment with triciribine and trastuzumab dramatically and significantly inhibited tumor growth (FIG. 12A). Many of the tumors actually decreased in size and four of 7 mice had no palpable tumors after 5 weeks of treatment. Following treatment with RAD001 and trastuzumab, tumor growth was relatively slower compared to RAD001 or trastuzumab alone (FIG. 12B). Thus combining trastuzumab with triciribine or RAD001 effectively inhibited ErbB2-overexpressing, PTEN-deficient human breast cancer xenografts in vivo.

This invention has been described with reference to its preferred embodiments. Variations and modifications of the invention will be obvious to those skilled in the art from the foregoing detailed description of the invention. It is intended that all of these variations and modifications be included within the scope of this invention.

What is claimed is:

1. A method for identifying and treating leukemia with enhanced sensitivity to triciribine (TCN) in a patient in need thereof comprising:
   (a) obtaining a biological sample of a leukemia tumor or cancer from the patient;
   (b) determining whether the leukemia tumor or cancer overexpresses AKT kinase and/or has hyper-phosphorylated AKT and/or hyper-activated AKT; and
   (c) if the leukemia tumor or cancer has hyper-phosphorylated AKT and/or hyper-activated AKT, administering to said patient a therapeutically effective amount of triciribine (TCN) or triciribine-phosphate (TCN P) in a range of 0.5 to 350 mg per m$^2$ in combination or alternation with at least one additional chemotherapeutic agent selected from the group consisting of an antimetabolite drug, 5-fluorouracil, gemcitabine, purine analogues, and cytarabine.

2. The method of claim 1, wherein the overexpressed AKT kinase is a hyperactivated and phosphorylated AKT kinase.

3. The method of claim 1, wherein the leukemia includes a tumor or cancer cell having hyper-phosphorylated AKT.

4. The method of claim 1, wherein the leukemia includes a tumor or cancer cell having hyper-activated AKT.

5. The method of claim 1, wherein the leukemia is selected from acute myeloid leukemia, chronic myelogenous leukemia and acute lympoblastic leukemia.

6. The method of claim 1, wherein the leukemia is acute myeloid leukemia.

7. The method of claim 1, wherein the additional chemotherapeutic agent is an antimetabolite drug.

8. The method of claim 1, wherein the additional chemotherapeutic agent antimetabolite drug is selected from the group consisting of 5-fluorouracil, cytarabine, gemcitabine and purine analogues.

9. The method of claim 1, wherein the additional chemotherapeutic agent is cytarabine.

10. The method of claim 1, wherein at least 2, 5, 10, 15, 20, 25, 30, 35, 40, 45, or 50 mg/m$^2$ of TCN or TCN-P is administered to the patient.

11. The method of claim 1, wherein the TCN or TCN-P is administered as a dosing regimen.

12. The method of claim 11, wherein the dosing regimen includes administering TCN or TCN-P one time per week for three weeks followed by a one week period wherein the TCN or TCN-P is not administered.

13. The method of claim 11, wherein the dosing regimen includes a 28-day cycle.

14. The method of claim 11, wherein the dosing regimen includes administering TCN or TCN-P on days 1, 8 and 15 of the 28-day cycle.

15. The method of claim 11, wherein the dosing regimen is repeated at least 2, 3, 4 or 5 times or until regression of the tumor is evident.

16. The method of claim 1, wherein the TCN or TCN-P is administered intravenously.

17. The method of claim 1, wherein the TCN or TCN-P is administered as a single dose between 5-1,500 mg to yield levels of TCN or TCN-P in the patient of about 0.1-50 mg/kg.

18. The method of claim 1, comprising prior to administration: (b) determining whether the leukemia tumor or cancer overexpresses AKT kinase and/or has hyper-phosphorylated AKT and/or hyper-activated AKT kinase by at least 1.5 fold greater amounts of AKT kinase than contained in a control tissue.

19. The method of claim 1, wherein at least 10 to 65 mg/m$^2$ of TCN or TCN-P is administered to the patient.

20. The method of claim 1, wherein at least 25 to 65 mg/m$^2$ of TCN or TCN-P is administered to the patient.

21. A method for identifying and treating a patient having a leukemia tumor or a cancer cell with enhanced sensitivity to triciribine (TCN) comprising the steps of:
(a) determining whether the patient has a tumor or a cancer cell with enhanced sensitivity to TCN by:
(i) obtaining a biological sample of the leukemia tumor or cancer cell from the patient;
(ii) measuring the expression level of AKT kinase of the sample;
(iii) comparing the expression level of AKT kinase of the sample to the expression level in a control tissue wherein a 1.5 greater fold expression of AKT kinase in the sample compared to the control tissue is indicative of a patient having a tumor or cancer cell with enhanced sensitivity to TCN; and
(b) if the sample has enhanced sensitivity to TCN, administering to the patient TCN or TCN-P in a range of 0.5 to 350 mg per m$^2$.

22. A method for identifying and treating leukemia with enhanced sensitivity to triciribine (TCN) in a patient in need thereof comprising:
(a) obtaining a biological sample of a leukemia tumor or cancer from the patient;
(b) determining whether the leukemia tumor or cancer overexpresses AKT kinase and/or has hyper-phosphorylated AKT and/or hyper-activated AKT; and
(c) if the leukemia tumor or cancer has hyper-phosphorylated AKT and/or hyper-activated AKT, administering to said patient a therapeutically effective amount of triciribine (TCN) or triciribine-phosphate (TCN P) in a range of 0.5 to 350 mg per m$^2$.

* * * * *

SEQUENCE LISTING

<160> NUMBER OF SEQ ID NOS: 6

<210> SEQ ID NO 1
<211> LENGTH: 1443
<212> TYPE: DNA
<213> ORGANISM: Homo sapiens
<220> FEATURE:
<221> NAME/KEY: CDS
<222> LOCATION: (1)..(1443)

<400> SEQUENCE: 1

| | | | | | | | | | | | | | | | | |
|---|---|---|---|---|---|---|---|---|---|---|---|---|---|---|---|---|
| atg | aac | gac | gta | gcc | att | gtg | aag | gag | ggc | tgg | ctg | cac | aaa | cga | ggg | 48 |
| Met | Asn | Asp | Val | Ala | Ile | Val | Lys | Glu | Gly | Trp | Leu | His | Lys | Arg | Gly | |
| 1 | | | | 5 | | | | | 10 | | | | | 15 | | |
| gaa | tat | att | aaa | acc | tgg | cgg | cca | cgc | tac | ttc | ctc | ctc | aag | aac | gat | 96 |
| Glu | Tyr | Ile | Lys | Thr | Trp | Arg | Pro | Arg | Tyr | Phe | Leu | Leu | Lys | Asn | Asp | |
| | | | 20 | | | | | 25 | | | | | 30 | | | |
| ggc | acc | ttt | att | ggc | tac | aag | gaa | cgg | cct | cag | gat | gtg | gat | cag | cga | 144 |
| Gly | Thr | Phe | Ile | Gly | Tyr | Lys | Glu | Arg | Pro | Gln | Asp | Val | Asp | Gln | Arg | |
| | | 35 | | | | | 40 | | | | | 45 | | | | |
| gag | tcc | cca | ctc | aac | aac | ttc | tca | gtg | gca | caa | tgc | cag | ctg | atg | aag | 192 |
| Glu | Ser | Pro | Leu | Asn | Asn | Phe | Ser | Val | Ala | Gln | Cys | Gln | Leu | Met | Lys | |
| | 50 | | | | | 55 | | | | | 60 | | | | | |
| aca | gag | cgg | cca | agg | ccc | aac | acc | ttt | atc | atc | cgc | tgc | ctg | cag | tgg | 240 |
| Thr | Glu | Arg | Pro | Arg | Pro | Asn | Thr | Phe | Ile | Ile | Arg | Cys | Leu | Gln | Trp | |
| 65 | | | | | 70 | | | | | 75 | | | | | 80 | |
| acc | aca | gtc | att | gag | cgc | acc | ttc | cat | gta | gaa | acg | cct | gag | gag | cgg | 288 |
| Thr | Thr | Val | Ile | Glu | Arg | Thr | Phe | His | Val | Glu | Thr | Pro | Glu | Glu | Arg | |
| | | | | 85 | | | | | 90 | | | | | 95 | | |
| gaa | gaa | tgg | gcc | acc | gcc | att | cag | act | gtg | gcc | gat | gga | ctc | aag | agg | 336 |
| Glu | Glu | Trp | Ala | Thr | Ala | Ile | Gln | Thr | Val | Ala | Asp | Gly | Leu | Lys | Arg | |
| | | | 100 | | | | | 105 | | | | | 110 | | | |
| cag | gaa | gaa | gag | acg | atg | gac | ttc | cga | tca | ggc | tca | ccc | agt | gac | aac | 384 |
| Gln | Glu | Glu | Glu | Thr | Met | Asp | Phe | Arg | Ser | Gly | Ser | Pro | Ser | Asp | Asn | |
| | | 115 | | | | | 120 | | | | | 125 | | | | |
| tca | ggg | gct | gaa | gag | atg | gag | gtg | tcc | ctg | gcc | aag | ccc | aag | cac | cgt | 432 |
| Ser | Gly | Ala | Glu | Glu | Met | Glu | Val | Ser | Leu | Ala | Lys | Pro | Lys | His | Arg | |
| | 130 | | | | | 135 | | | | | 140 | | | | | |
| gtg | acc | atg | aac | gag | ttt | gag | tac | ctg | aaa | cta | ctg | ggc | aag | ggc | acc | 480 |
| Val | Thr | Met | Asn | Glu | Phe | Glu | Tyr | Leu | Lys | Leu | Leu | Gly | Lys | Gly | Thr | |
| 145 | | | | | 150 | | | | | 155 | | | | | 160 | |
| ttt | ggg | aaa | gtg | att | ctg | gta | aaa | gag | aag | gcc | aca | ggc | cgc | tac | tat | 528 |
| Phe | Gly | Lys | Val | Ile | Leu | Val | Lys | Glu | Lys | Ala | Thr | Gly | Arg | Tyr | Tyr | |
| | | | | 165 | | | | | 170 | | | | | 175 | | |
| gcc | atg | aag | atc | ctc | aag | aag | gag | gtc | atc | gtc | gcc | aag | gat | gag | gtt | 576 |
| Ala | Met | Lys | Ile | Leu | Lys | Lys | Glu | Val | Ile | Val | Ala | Lys | Asp | Glu | Val | |
| | | | 180 | | | | | 185 | | | | | 190 | | | |
| gcc | cac | acg | ctt | act | gaa | aac | cgt | gtc | ctg | cag | aac | tct | agg | cat | ccc | 624 |
| Ala | His | Thr | Leu | Thr | Glu | Asn | Arg | Val | Leu | Gln | Asn | Ser | Arg | His | Pro | |
| | | 195 | | | | | 200 | | | | | 205 | | | | |
| ttc | ctt | acg | gcc | ctc | aag | tac | tca | ttc | cag | acc | cac | gac | cgc | ctc | tgc | 672 |
| Phe | Leu | Thr | Ala | Leu | Lys | Tyr | Ser | Phe | Gln | Thr | His | Asp | Arg | Leu | Cys | |
| | 210 | | | | | 215 | | | | | 220 | | | | | |
| ttt | gtc | atg | gag | tat | gcc | aac | ggg | ggc | gag | ctc | ttc | ttc | cac | ctg | tct | 720 |
| Phe | Val | Met | Glu | Tyr | Ala | Asn | Gly | Gly | Glu | Leu | Phe | Phe | His | Leu | Ser | |
| 225 | | | | | 230 | | | | | 235 | | | | | 240 | |
| cga | gag | cgc | gtg | ttc | tcc | gag | gac | cgg | gcc | cgc | ttc | tat | ggt | gcg | gag | 768 |
| Arg | Glu | Arg | Val | Phe | Ser | Glu | Asp | Arg | Ala | Arg | Phe | Tyr | Gly | Ala | Glu | |
| | | | | 245 | | | | | 250 | | | | | 255 | | |
| att | gtg | tct | gcc | ctg | gac | tac | ttg | cac | tcg | gag | aag | aac | gtg | gtg | tac | 816 |
| Ile | Val | Ser | Ala | Leu | Asp | Tyr | Leu | His | Ser | Glu | Lys | Asn | Val | Val | Tyr | |
| | | | 260 | | | | | 265 | | | | | 270 | | | |
| cgg | gac | ctg | aag | cta | gag | aac | ctc | atg | ctg | gac | aag | gac | ggg | cac | atc | 864 |
| Arg | Asp | Leu | Lys | Leu | Glu | Asn | Leu | Met | Leu | Asp | Lys | Asp | Gly | His | Ile | |
| | | 275 | | | | | 280 | | | | | 285 | | | | |
| aag | ata | acg | gac | ttc | ggg | ctg | tgc | aag | gag | ggg | atc | aag | gat | ggt | gcc | 912 |
| Lys | Ile | Thr | Asp | Phe | Gly | Leu | Cys | Lys | Glu | Gly | Ile | Lys | Asp | Gly | Ala | |
| | 290 | | | | | 295 | | | | | 300 | | | | | |

| | | | | | | | | | | | | | | | | |
|---|---|---|---|---|---|---|---|---|---|---|---|---|---|---|---|---|
| act | atg | aag | aca | ttc | tgc | gga | acg | ccg | gag | tac | ctg | gcc | cct | gag | gtg | 960 |
| Thr | Met | Lys | Thr | Phe | Cys | Gly | Thr | Pro | Glu | Tyr | Leu | Ala | Pro | Glu | Val | |
| 305 | | | | 310 | | | | | 315 | | | | | 320 | | |
| ctg | gaa | gac | aac | gac | tac | ggc | cgt | gca | gtg | gac | tgg | tgg | ggg | ctg | ggc | 1008 |
| Leu | Glu | Asp | Asn | Asp | Tyr | Gly | Arg | Ala | Val | Asp | Trp | Trp | Gly | Leu | Gly | |
| | | | | 325 | | | | | 330 | | | | | 335 | | |
| gtg | gtc | atg | tat | gag | atg | atg | tgt | ggc | cgc | ctg | ccc | ttc | tac | aac | cag | 1056 |
| Val | Val | Met | Tyr | Glu | Met | Met | Cys | Gly | Arg | Leu | Pro | Phe | Tyr | Asn | Gln | |
| | | | 340 | | | | | 345 | | | | | 350 | | | |
| gac | cac | gag | aag | ctg | ttc | gag | ctg | atc | ctc | atg | gag | gag | atc | cgc | ttc | 1104 |
| Asp | His | Glu | Lys | Leu | Phe | Glu | Leu | Ile | Leu | Met | Glu | Glu | Ile | Arg | Phe | |
| | | | 355 | | | | | 360 | | | | | 365 | | | |
| ccg | cgc | aca | ctc | ggc | cct | gag | gcc | aag | tcc | ctg | ctc | tcc | ggg | ctg | ctc | 1152 |
| Pro | Arg | Thr | Leu | Gly | Pro | Glu | Ala | Lys | Ser | Leu | Leu | Ser | Gly | Leu | Leu | |
| | 370 | | | | | 375 | | | | | 380 | | | | | |
| aag | aag | gac | cct | aca | cag | agg | ctc | ggt | ggg | ggc | tct | gag | gat | gcc | aag | 1200 |
| Lys | Lys | Asp | Pro | Thr | Gln | Arg | Leu | Gly | Gly | Gly | Ser | Glu | Asp | Ala | Lys | |
| 385 | | | | | 390 | | | | | 395 | | | | | 400 | |
| gag | atc | atg | cag | cac | cgg | ttc | ttt | gcc | aac | atc | gtg | tgg | cag | gat | gtg | 1248 |
| Glu | Ile | Met | Gln | His | Arg | Phe | Phe | Ala | Asn | Ile | Val | Trp | Gln | Asp | Val | |
| | | | | 405 | | | | | 410 | | | | | 415 | | |
| tat | gag | aag | aag | ctg | agc | cca | cct | ttc | aag | ccc | cag | gtc | acc | tct | gag | 1296 |
| Tyr | Glu | Lys | Lys | Leu | Ser | Pro | Pro | Phe | Lys | Pro | Gln | Val | Thr | Ser | Glu | |
| | | | 420 | | | | | 425 | | | | | 430 | | | |
| act | gac | acc | agg | tat | ttc | gat | gag | gag | ttc | aca | gct | cag | atg | atc | acc | 1344 |
| Thr | Asp | Thr | Arg | Tyr | Phe | Asp | Glu | Glu | Phe | Thr | Ala | Gln | Met | Ile | Thr | |
| | | | 435 | | | | | 440 | | | | | 445 | | | |
| atc | acg | ccg | cct | gat | caa | gat | gac | agc | atg | gag | tgt | gtg | gac | agt | gag | 1392 |
| Ile | Thr | Pro | Pro | Asp | Gln | Asp | Asp | Ser | Met | Glu | Cys | Val | Asp | Ser | Glu | |
| | 450 | | | | | 455 | | | | | 460 | | | | | |
| cgg | agg | ccg | cac | ttc | ccc | cag | ttc | tcc | tac | tca | gcc | agt | ggc | aca | gcc | 1440 |
| Arg | Arg | Pro | His | Phe | Pro | Gln | Phe | Ser | Tyr | Ser | Ala | Ser | Gly | Thr | Ala | |
| 465 | | | | 470 | | | | | 475 | | | | | 480 | | |
| tga | | | | | | | | | | | | | | | | 1443 |

<210> SEQ ID NO 2
<211> LENGTH: 480
<212> TYPE: PRT
<213> ORGANISM: Homo sapiens

<400> SEQUENCE: 2

Met Asn Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ser Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
            85                  90                  95

Glu Glu Trp Ala Thr Ala Ile Gln Thr Val Ala Asp Gly Leu Lys Arg
        100                 105                 110

Gln Glu Glu Glu Thr Met Asp Phe Arg Ser Gly Ser Pro Ser Asp Asn
    115                 120                 125

Ser Gly Ala Glu Glu Met Glu Val Ser Leu Ala Lys Pro Lys His Arg

```
                130                 135                 140
Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Thr Gln Arg Leu Gly Gly Gly Ser Glu Asp Ala Lys
385                 390                 395                 400

Glu Ile Met Gln His Arg Phe Phe Ala Asn Ile Val Trp Gln Asp Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 3
<211> LENGTH: 1515
<212> TYPE: DNA
<213> ORGANISM: Homo sapiens
<220> FEATURE:
<221> NAME/KEY: CDS
<222> LOCATION: (1)..(1446)

<400> SEQUENCE: 3 atg aat gag gtg tct gtc atc aaa gaa ggc tgg ctc cac aag cgt ggt    48
Met Asn Glu Val Ser Val Ile Lys Glu Gly Trp Leu His Lys Arg Gly
1               5                  10                  15
```

-continued

| | | |
|---|---|---|
| gaa tac atc aag acc tgg agg cca cgg tac ttc ctg ctg aag agc gac<br>Glu Tyr Ile Lys Thr Trp Arg Pro Arg Tyr Phe Leu Leu Lys Ser Asp<br>20                        25                    30 | 96 |
| ggc tcc ttc att ggg tac aag gag agg ccc gag gcc cct gat cag act<br>Gly Ser Phe Ile Gly Tyr Lys Glu Arg Pro Glu Ala Pro Asp Gln Thr<br>35                       40                      45 | 144 |
| cta ccc ccc tta aac aac ttc tcc gta gca gaa tgc cag ctg atg aag<br>Leu Pro Pro Leu Asn Asn Phe Ser Val Ala Glu Cys Gln Leu Met Lys<br>50                       55                     60 | 192 |
| acc gag agg ccg cga ccc aac acc ttt gtc ata cgc tgc ctg cag tgg<br>Thr Glu Arg Pro Arg Pro Asn Thr Phe Val Ile Arg Cys Leu Gln Trp<br>65                       70                      75                     80 | 240 |
| acc aca gtc atc gag agg acc ttc cac gtg gat tct cca gac gag agg<br>Thr Thr Val Ile Glu Arg Thr Phe His Val Asp Ser Pro Asp Glu Arg<br>                     85                     90                       95 | 288 |
| gag gag tgg atg cgg gcc atc cag atg gtc gcc aac agc ctc aag cag<br>Glu Glu Trp Met Arg Ala Ile Gln Met Val Ala Asn Ser Leu Lys Gln<br>                    100                   105                  110 | 336 |
| cgg gcc cca ggc gag gac ccc atg gac tac aag tgt ggc tcc ccc agt<br>Arg Ala Pro Gly Glu Asp Pro Met Asp Tyr Lys Cys Gly Ser Pro Ser<br>115                    120                   125 | 384 |
| gac tcc tcc acg act gag gag atg gaa gtg gcg gtc agc aag gca cgg<br>Asp Ser Ser Thr Thr Glu Glu Met Glu Val Ala Val Ser Lys Ala Arg<br>130                    135                   140 | 432 |
| gct aaa gtg acc atg aat gac ttc gac tat ctc aaa ctc ctt ggc aag<br>Ala Lys Val Thr Met Asn Asp Phe Asp Tyr Leu Lys Leu Leu Gly Lys<br>145                    150                   155                  160 | 480 |
| gga acc ttt ggc aaa gtc atc ctg gtg cgg gag aag gcc act ggc cgc<br>Gly Thr Phe Gly Lys Val Ile Leu Val Arg Glu Lys Ala Thr Gly Arg<br>                    165                   170                  175 | 528 |
| tac tac gcc atg aag atc ctg cga aag gaa gtc atc att gcc aag gat<br>Tyr Tyr Ala Met Lys Ile Leu Arg Lys Glu Val Ile Ile Ala Lys Asp<br>                    180                   185                  190 | 576 |
| gaa gtc gct cac aca gtc acc gag agc cgg gtc ctc cag aac acc agg<br>Glu Val Ala His Thr Val Thr Glu Ser Arg Val Leu Gln Asn Thr Arg<br>                    195                   200                  205 | 624 |
| cac ccg ttc ctc act gcg ctg aag tat gcc ttc cag acc cac gac cgc<br>His Pro Phe Leu Thr Ala Leu Lys Tyr Ala Phe Gln Thr His Asp Arg<br>210                      215                   220 | 672 |
| ctg tgc ttt gtg atg gag tat gcc aac ggg ggt gag ctg ttc ttc cac<br>Leu Cys Phe Val Met Glu Tyr Ala Asn Gly Gly Glu Leu Phe Phe His<br>225                    230                   235                  240 | 720 |
| ctg tcc cgg gag cgt gtc ttc aca gag gag cgg gcc cgg ttt tat ggt<br>Leu Ser Arg Glu Arg Val Phe Thr Glu Glu Arg Ala Arg Phe Tyr Gly<br>                    245                   250                  255 | 768 |
| gca gag att gtc tcg gct ctt gag tac ttg cac tcg cgg gac gtg gta<br>Ala Glu Ile Val Ser Ala Leu Glu Tyr Leu His Ser Arg Asp Val Val<br>                    260                   265                  270 | 816 |
| tac cgc gac atc aag ctg gaa aac ctc atg ctg gac aaa gat ggc cac<br>Tyr Arg Asp Ile Lys Leu Glu Asn Leu Met Leu Asp Lys Asp Gly His<br>275                    280                   285 | 864 |
| atc aag atc act gac ttt ggc ctc tgc aaa gag ggc atc agt gac ggg<br>Ile Lys Ile Thr Asp Phe Gly Leu Cys Lys Glu Gly Ile Ser Asp Gly<br>290                    295                   300 | 912 |
| gcc acc atg aaa acc ttc tgt ggg acc ccg gag tac ctg gcg cct gag<br>Ala Thr Met Lys Thr Phe Cys Gly Thr Pro Glu Tyr Leu Ala Pro Glu<br>305                    310                   315                  320 | 960 |
| gtg ctg gag gac aat gac tat ggc cgg gcc gtg gac tgg tgg ggg ctg<br>Val Leu Glu Asp Asn Asp Tyr Gly Arg Ala Val Asp Trp Trp Gly Leu | 1008 |

```
                    325                    330                    335
ggt gtg gtc atg tac gag atg atg tgc ggc cgc ctg ccc ttc tac aac    1056
Gly Val Val Met Tyr Glu Met Met Cys Gly Arg Leu Pro Phe Tyr Asn
            340                    345                    350 cag gac cac gag cgc ctc ttc gag ctc atc ctc atg gaa gag atc cgc    1104
Gln Asp His Glu Arg Leu Phe Glu Leu Ile Leu Met Glu Glu Ile Arg
                355                    360                    365 ttc ccg cgc acg ctc agc ccc gag gcc aag tcc ctg ctt gct ggg ctg    1152
Phe Pro Arg Thr Leu Ser Pro Glu Ala Lys Ser Leu Leu Ala Gly Leu
        370                    375                    380 ctt aag aag gac ccc aag cag agg ctt ggt ggg ggg ccc agc gat gcc    1200
Leu Lys Lys Asp Pro Lys Gln Arg Leu Gly Gly Gly Pro Ser Asp Ala
385                    390                    395                    400 aag gag gtc atg gag cac agg ttc ttc ctc agc atc aac tgg cag gac    1248
Lys Glu Val Met Glu His Arg Phe Phe Leu Ser Ile Asn Trp Gln Asp
                405                    410                    415 gtg gtc cag aag aag ctc ctg cca ccc ttc aaa cct cag gtc acg tcc    1296
Val Val Gln Lys Lys Leu Leu Pro Pro Phe Lys Pro Gln Val Thr Ser
            420                    425                    430 gag gtc gac aca agg tac ttc gat gat gaa ttt acc gcc cag tcc atc    1344
Glu Val Asp Thr Arg Tyr Phe Asp Asp Glu Phe Thr Ala Gln Ser Ile
                435                    440                    445 aca atc aca ccc cct gac cgc tat gac agc ctg ggc tta ctg gag ctg    1392
Thr Ile Thr Pro Pro Asp Arg Tyr Asp Ser Leu Gly Leu Leu Glu Leu
        450                    455                    460 gac cag cgg acc cac ttc ccc cag ttc tcc tac tcg gcc agc atc cgc    1440
Asp Gln Arg Thr His Phe Pro Gln Phe Ser Tyr Ser Ala Ser Ile Arg
465                    470                    475                    480 gag tga gcagtctgcc cacgcagagg acgcacgctc gctgccatca ccgctgggtg    1496
Glu
gttttttacc cctgcccgg                                              1515

<210> SEQ ID NO 4
<211> LENGTH: 481
<212> TYPE: PRT
<213> ORGANISM: Homo sapiens

<400> SEQUENCE: 4

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160
```

```
Gly Thr Phe Gly Lys Val Ile Leu Val Arg Glu Lys Ala Thr Gly Arg
            165                 170                 175
Tyr Tyr Ala Met Lys Ile Leu Arg Lys Glu Val Ile Ile Ala Lys Asp
            180                 185                 190
Glu Val Ala His Thr Val Thr Glu Ser Arg Val Leu Gln Asn Thr Arg
            195                 200                 205
His Pro Phe Leu Thr Ala Leu Lys Tyr Ala Phe Gln Thr His Asp Arg
            210                 215                 220
Leu Cys Phe Val Met Glu Tyr Ala Asn Gly Gly Glu Leu Phe Phe His
225                 230                 235                 240
Leu Ser Arg Glu Arg Val Phe Thr Glu Glu Arg Ala Arg Phe Tyr Gly
            245                 250                 255
Ala Glu Ile Val Ser Ala Leu Glu Tyr Leu His Ser Arg Asp Val Val
            260                 265                 270
Tyr Arg Asp Ile Lys Leu Glu Asn Leu Met Leu Asp Lys Asp Gly His
            275                 280                 285
Ile Lys Ile Thr Asp Phe Gly Leu Cys Lys Glu Gly Ile Ser Asp Gly
            290                 295                 300
Ala Thr Met Lys Thr Phe Cys Gly Thr Pro Glu Tyr Leu Ala Pro Glu
305                 310                 315                 320
Val Leu Glu Asp Asn Asp Tyr Gly Arg Ala Val Asp Trp Trp Gly Leu
            325                 330                 335
Gly Val Val Met Tyr Glu Met Met Cys Gly Arg Leu Pro Phe Tyr Asn
            340                 345                 350
Gln Asp His Glu Arg Leu Phe Glu Leu Ile Leu Met Glu Glu Ile Arg
            355                 360                 365
Phe Pro Arg Thr Leu Ser Pro Glu Ala Lys Ser Leu Leu Ala Gly Leu
            370                 375                 380
Leu Lys Lys Asp Pro Lys Gln Arg Leu Gly Gly Gly Pro Ser Asp Ala
385                 390                 395                 400
Lys Glu Val Met Glu His Arg Phe Phe Leu Ser Ile Asn Trp Gln Asp
            405                 410                 415
Val Val Gln Lys Lys Leu Leu Pro Pro Phe Lys Pro Gln Val Thr Ser
            420                 425                 430
Glu Val Asp Thr Arg Tyr Phe Asp Asp Glu Phe Thr Ala Gln Ser Ile
            435                 440                 445
Thr Ile Thr Pro Pro Asp Arg Tyr Asp Ser Leu Gly Leu Leu Glu Leu
            450                 455                 460
Asp Gln Arg Thr His Phe Pro Gln Phe Ser Tyr Ser Ala Ser Ile Arg
465                 470                 475                 480
Glu

<210> SEQ ID NO 5
<211> LENGTH: 1510
<212> TYPE: DNA
<213> ORGANISM: Homo sapiens
<220> FEATURE:
<221> NAME/KEY: CDS
<222> LOCATION: (3)..(1460)

<400> SEQUENCE: 5 gg gct cag agg gga gtc atc atg agc gat gtt acc att gtg aaa gaa        47
   Ala Gln Arg Gly Val Ile Met Ser Asp Val Thr Ile Val Lys Glu
   1               5                   10                  15 ggt tgg gtt cag aag agg gga gaa tat ata aaa aac tgg agg cca aga       95
```

| | | | | | | | | | | | | | |
|---|---|---|---|---|---|---|---|---|---|---|---|---|---|
| Gly | Trp | Val | Gln | Lys | Arg | Gly | Glu | Tyr | Ile | Lys | Asn | Trp | Arg | Pro | Arg |
| | | | 20 | | | | | 25 | | | | | 30 | | |

| tac | ttc | ctt | ttg | aag | aca | gat | ggc | tca | ttc | ata | gga | tat | aaa | gag | aaa | 143 |
|---|---|---|---|---|---|---|---|---|---|---|---|---|---|---|---|---|
| Tyr | Phe | Leu | Leu | Lys | Thr | Asp | Gly | Ser | Phe | Ile | Gly | Tyr | Lys | Glu | Lys | |
| | | | 35 | | | | | 40 | | | | | 45 | | | |

| cct | caa | gat | gtg | gat | tta | cct | tat | ccc | ctc | aac | aac | ttt | tca | gtg | gca | 191 |
|---|---|---|---|---|---|---|---|---|---|---|---|---|---|---|---|---|
| Pro | Gln | Asp | Val | Asp | Leu | Pro | Tyr | Pro | Leu | Asn | Asn | Phe | Ser | Val | Ala | |
| | | 50 | | | | | 55 | | | | | 60 | | | | |

| aaa | tgc | cag | tta | atg | aaa | aca | gaa | cga | cca | aag | cca | aac | aca | ttt | ata | 239 |
|---|---|---|---|---|---|---|---|---|---|---|---|---|---|---|---|---|
| Lys | Cys | Gln | Leu | Met | Lys | Thr | Glu | Arg | Pro | Lys | Pro | Asn | Thr | Phe | Ile | |
| | 65 | | | | | 70 | | | | | 75 | | | | | |

| atc | aga | tgt | ctc | cag | tgg | act | act | gtt | ata | gag | aga | aca | ttt | cat | gta | 287 |
|---|---|---|---|---|---|---|---|---|---|---|---|---|---|---|---|---|
| Ile | Arg | Cys | Leu | Gln | Trp | Thr | Thr | Val | Ile | Glu | Arg | Thr | Phe | His | Val | |
| 80 | | | | | 85 | | | | | 90 | | | | | 95 | |

| gat | act | cca | gag | gaa | agg | gaa | gaa | tgg | aca | gaa | gct | atc | cag | gct | gta | 335 |
|---|---|---|---|---|---|---|---|---|---|---|---|---|---|---|---|---|
| Asp | Thr | Pro | Glu | Glu | Arg | Glu | Glu | Trp | Thr | Glu | Ala | Ile | Gln | Ala | Val | |
| | | | | 100 | | | | | 105 | | | | | 110 | | |

| gca | gac | aga | ctg | cag | agg | caa | gaa | gag | gag | aga | atg | aat | tgt | agt | cca | 383 |
|---|---|---|---|---|---|---|---|---|---|---|---|---|---|---|---|---|
| Ala | Asp | Arg | Leu | Gln | Arg | Gln | Glu | Glu | Glu | Arg | Met | Asn | Cys | Ser | Pro | |
| | | | 115 | | | | | 120 | | | | | 125 | | | |

| act | tca | caa | att | gat | aat | ata | gga | gag | gaa | gag | atg | gat | gcc | tct | aca | 431 |
|---|---|---|---|---|---|---|---|---|---|---|---|---|---|---|---|---|
| Thr | Ser | Gln | Ile | Asp | Asn | Ile | Gly | Glu | Glu | Glu | Met | Asp | Ala | Ser | Thr | |
| | | 130 | | | | | 135 | | | | | 140 | | | | |

| acc | cat | cat | aaa | aga | aag | aca | atg | aat | gat | ttt | gac | tat | ttg | aaa | cta | 479 |
|---|---|---|---|---|---|---|---|---|---|---|---|---|---|---|---|---|
| Thr | His | His | Lys | Arg | Lys | Thr | Met | Asn | Asp | Phe | Asp | Tyr | Leu | Lys | Leu | |
| 145 | | | | | 150 | | | | | 155 | | | | | | |

| cta | ggt | aaa | ggc | act | ttt | ggg | aaa | gtt | att | ttg | gtt | cga | gag | aag | gca | 527 |
|---|---|---|---|---|---|---|---|---|---|---|---|---|---|---|---|---|
| Leu | Gly | Lys | Gly | Thr | Phe | Gly | Lys | Val | Ile | Leu | Val | Arg | Glu | Lys | Ala | |
| 160 | | | | | 165 | | | | | 170 | | | | | 175 | |

| agt | gga | aaa | tac | tat | gct | atg | aag | att | ctg | aag | aaa | gaa | gtc | att | att | 575 |
|---|---|---|---|---|---|---|---|---|---|---|---|---|---|---|---|---|
| Ser | Gly | Lys | Tyr | Tyr | Ala | Met | Lys | Ile | Leu | Lys | Lys | Glu | Val | Ile | Ile | |
| | | | 180 | | | | | 185 | | | | | 190 | | | |

| gca | aag | gat | gaa | gtg | gca | cac | act | cta | act | gaa | agc | aga | gta | tta | aag | 623 |
|---|---|---|---|---|---|---|---|---|---|---|---|---|---|---|---|---|
| Ala | Lys | Asp | Glu | Val | Ala | His | Thr | Leu | Thr | Glu | Ser | Arg | Val | Leu | Lys | |
| | | | 195 | | | | | 200 | | | | | 205 | | | |

| aac | act | aga | cat | ccc | ttt | tta | aca | tcc | ttg | aaa | tat | tcc | ttc | cag | aca | 671 |
|---|---|---|---|---|---|---|---|---|---|---|---|---|---|---|---|---|
| Asn | Thr | Arg | His | Pro | Phe | Leu | Thr | Ser | Leu | Lys | Tyr | Ser | Phe | Gln | Thr | |
| | | 210 | | | | | 215 | | | | | 220 | | | | |

| aaa | gac | cgt | ttg | tgt | ttt | gtg | atg | gaa | tat | gtt | aat | ggg | ggc | gag | ctg | 719 |
|---|---|---|---|---|---|---|---|---|---|---|---|---|---|---|---|---|
| Lys | Asp | Arg | Leu | Cys | Phe | Val | Met | Glu | Tyr | Val | Asn | Gly | Gly | Glu | Leu | |
| | 225 | | | | | 230 | | | | | 235 | | | | | |

| ttt | ttc | cat | ttg | tcg | aga | gag | cgg | gtg | ttc | tct | gag | gac | cgc | aca | cgt | 767 |
|---|---|---|---|---|---|---|---|---|---|---|---|---|---|---|---|---|
| Phe | Phe | His | Leu | Ser | Arg | Glu | Arg | Val | Phe | Ser | Glu | Asp | Arg | Thr | Arg | |
| 240 | | | | | 245 | | | | | 250 | | | | | 255 | |

| ttc | tat | ggt | gca | gaa | att | gtc | tct | gcc | ttg | gac | tat | cta | cat | tcc | gga | 815 |
|---|---|---|---|---|---|---|---|---|---|---|---|---|---|---|---|---|
| Phe | Tyr | Gly | Ala | Glu | Ile | Val | Ser | Ala | Leu | Asp | Tyr | Leu | His | Ser | Gly | |
| | | | 260 | | | | | 265 | | | | | 270 | | | |

| aag | att | gtg | tac | cgt | gat | ctc | aag | ttg | gag | aat | cta | atg | ctg | gac | aaa | 863 |
|---|---|---|---|---|---|---|---|---|---|---|---|---|---|---|---|---|
| Lys | Ile | Val | Tyr | Arg | Asp | Leu | Lys | Leu | Glu | Asn | Leu | Met | Leu | Asp | Lys | |
| | | | 275 | | | | | 280 | | | | | 285 | | | |

| gat | ggc | cac | ata | aaa | att | aca | gat | ttt | gga | ctt | tgc | aaa | gaa | ggg | atc | 911 |
|---|---|---|---|---|---|---|---|---|---|---|---|---|---|---|---|---|
| Asp | Gly | His | Ile | Lys | Ile | Thr | Asp | Phe | Gly | Leu | Cys | Lys | Glu | Gly | Ile | |
| | | 290 | | | | | 295 | | | | | 300 | | | | |

| aca | gat | gca | gcc | acc | atg | aag | aca | ttc | tgt | ggc | act | cca | gaa | tat | ctg | 959 |
|---|---|---|---|---|---|---|---|---|---|---|---|---|---|---|---|---|
| Thr | Asp | Ala | Ala | Thr | Met | Lys | Thr | Phe | Cys | Gly | Thr | Pro | Glu | Tyr | Leu | |
| | 305 | | | | | 310 | | | | | 315 | | | | | |

| gca | cca | gag | gtg | tta | gaa | gat | aat | gac | tat | ggc | cga | gca | gta | gac | tgg | 1007 |
|---|---|---|---|---|---|---|---|---|---|---|---|---|---|---|---|---|
| Ala | Pro | Glu | Val | Leu | Glu | Asp | Asn | Asp | Tyr | Gly | Arg | Ala | Val | Asp | Trp | |
| 320 | | | | | 325 | | | | | 330 | | | | | 335 | |

-continued

| | | |
|---|---|---|
| tgg ggc cta ggg gtt gtc atg tat gaa atg atg tgt ggg agg tta cct<br>Trp Gly Leu Gly Val Val Met Tyr Glu Met Met Cys Gly Arg Leu Pro<br>340                          345                       350 | 1055 |
| ttc tac aac cag gac cat gag aaa ctt ttt gaa tta ata tta atg gaa<br>Phe Tyr Asn Gln Asp His Glu Lys Leu Phe Glu Leu Ile Leu Met Glu<br>355                       360                       365 | 1103 |
| gac att aaa ttt cct cga aca ctc tct tca gat gca aaa tca ttg ctt<br>Asp Ile Lys Phe Pro Arg Thr Leu Ser Ser Asp Ala Lys Ser Leu Leu<br>370                       375                       380 | 1151 |
| tca ggg ctc ttg ata aag gat cca aat aaa cgc ctt ggt gga gga cca<br>Ser Gly Leu Leu Ile Lys Asp Pro Asn Lys Arg Leu Gly Gly Gly Pro<br>385                       390                       395 | 1199 |
| gat gat gca aaa gaa att atg aga cac agt ttc ttc tct gga gta aac<br>Asp Asp Ala Lys Glu Ile Met Arg His Ser Phe Phe Ser Gly Val Asn<br>400                       405                     410           415 | 1247 |
| tgg caa gat gta tat gat aaa aag ctt gta cct cct ttt aaa cct caa<br>Trp Gln Asp Val Tyr Asp Lys Lys Leu Val Pro Pro Phe Lys Pro Gln<br>                   420                       425                     430 | 1295 |
| gta aca tct gag aca gat act aga tat ttt gat gaa gaa ttt aca gct<br>Val Thr Ser Glu Thr Asp Thr Arg Tyr Phe Asp Glu Glu Phe Thr Ala<br>               435                       440                     445 | 1343 |
| cag act att aca ata aca cca cct gaa aaa tat gat gag gat ggt atg<br>Gln Thr Ile Thr Ile Thr Pro Pro Glu Lys Tyr Asp Glu Asp Gly Met<br>450                       455                       460 | 1391 |
| gac tgc atg gac aat gag agg cgg ccg cat ttc cct caa ttt tcc tac<br>Asp Cys Met Asp Asn Glu Arg Arg Pro His Phe Pro Gln Phe Ser Tyr<br>465                       470                       475 | 1439 |
| tct gca agt gga cga gaa taa gtctctttca ttctgctact tcactgtcat<br>Ser Ala Ser Gly Arg Glu<br>480                     485 | 1490 |
| cttcaattta ttactgaaaa | 1510 |

<210> SEQ ID NO 6
<211> LENGTH: 485
<212> TYPE: PRT
<213> ORGANISM: Homo sapiens

<400> SEQUENCE: 6

Ala Gln Arg Gly Val Ile Met Ser Asp Val Thr Ile Val Lys Glu Gly
1                   5                   10                15

Trp Val Gln Lys Arg Gly Glu Tyr Ile Lys Asn Trp Arg Pro Arg Tyr
                   20                   25                   30

Phe Leu Leu Lys Thr Asp Gly Ser Phe Ile Gly Tyr Lys Glu Lys Pro
                35                   40                   45

Gln Asp Val Asp Leu Pro Tyr Pro Leu Asn Asn Phe Ser Val Ala Lys
    50                   55                   60

Cys Gln Leu Met Lys Thr Glu Arg Pro Lys Pro Asn Thr Phe Ile Ile
65                  70                   75                   80

Arg Cys Leu Gln Trp Thr Thr Val Ile Glu Arg Thr Phe His Val Asp
                85                   90                   95

Thr Pro Glu Glu Arg Glu Glu Trp Thr Glu Ala Ile Gln Ala Val Ala
                   100                  105                 110

Asp Arg Leu Gln Arg Gln Glu Glu Glu Arg Met Asn Cys Ser Pro Thr
             115                  120                 125

Ser Gln Ile Asp Asn Ile Gly Glu Glu Glu Met Asp Ala Ser Thr Thr
    130                   135                  140

His His Lys Arg Lys Thr Met Asn Asp Phe Asp Tyr Leu Lys Leu Leu
145                  150                  155               160

-continued

```
Gly Lys Gly Thr Phe Gly Lys Val Ile Leu Val Arg Glu Lys Ala Ser
                165                 170                 175
Gly Lys Tyr Tyr Ala Met Lys Ile Leu Lys Lys Glu Val Ile Ile Ala
                180                 185                 190
Lys Asp Glu Val Ala His Thr Leu Thr Glu Ser Arg Val Leu Lys Asn
                195                 200                 205
Thr Arg His Pro Phe Leu Thr Ser Leu Lys Tyr Ser Phe Gln Thr Lys
                210                 215                 220
Asp Arg Leu Cys Phe Val Met Glu Tyr Val Asn Gly Gly Glu Leu Phe
225                 230                 235                 240
Phe His Leu Ser Arg Glu Arg Val Phe Ser Glu Asp Arg Thr Arg Phe
                245                 250                 255
Tyr Gly Ala Glu Ile Val Ser Ala Leu Asp Tyr Leu His Ser Gly Lys
                260                 265                 270
Ile Val Tyr Arg Asp Leu Lys Leu Glu Asn Leu Met Leu Asp Lys Asp
                275                 280                 285
Gly His Ile Lys Ile Thr Asp Phe Gly Leu Cys Lys Glu Gly Ile Thr
                290                 295                 300
Asp Ala Ala Thr Met Lys Thr Phe Cys Gly Thr Pro Glu Tyr Leu Ala
305                 310                 315                 320
Pro Glu Val Leu Glu Asp Asn Asp Tyr Gly Arg Ala Val Asp Trp Trp
                325                 330                 335
Gly Leu Gly Val Val Met Tyr Glu Met Met Cys Gly Arg Leu Pro Phe
                340                 345                 350
Tyr Asn Gln Asp His Glu Lys Leu Phe Glu Leu Ile Leu Met Glu Asp
                355                 360                 365
Ile Lys Phe Pro Arg Thr Leu Ser Ser Asp Ala Lys Ser Leu Leu Ser
                370                 375                 380
Gly Leu Leu Ile Lys Asp Pro Asn Lys Arg Leu Gly Gly Gly Pro Asp
385                 390                 395                 400
Asp Ala Lys Glu Ile Met Arg His Ser Phe Phe Ser Gly Val Asn Trp
                405                 410                 415
Gln Asp Val Tyr Asp Lys Lys Leu Val Pro Pro Phe Lys Pro Gln Val
                420                 425                 430
Thr Ser Glu Thr Asp Thr Arg Tyr Phe Asp Glu Glu Phe Thr Ala Gln
                435                 440                 445
Thr Ile Thr Ile Thr Pro Pro Glu Lys Tyr Asp Glu Asp Gly Met Asp
                450                 455                 460
Cys Met Asp Asn Glu Arg Arg Pro His Phe Pro Gln Phe Ser Tyr Ser
465                 470                 475                 480
Ala Ser Gly Arg Glu
                485
```